(12) United States Patent
Vunjak-Novakovic et al.

(10) Patent No.: US 11,299,714 B2
(45) Date of Patent: Apr. 12, 2022

(54) ENGINEERED ADULT-LIKE HUMAN HEART TISSUE

(71) Applicant: THE TRUSTEES OF COLUMBIA UNIVERSITY IN THE CITY OF NEW YORK, New York, NY (US)

(72) Inventors: Gordana Vunjak-Novakovic, New York, NY (US); Keith Yeager, Jersey City, NJ (US); Kacey Ronaldson, Midlothian, VA (US); Stephen Ma, New York, NY (US); Timothy Chen, New York, NY (US)

(73) Assignee: The Trustees of Columbia University in The City of New York, New York, NY (US)

( * ) Notice: Subject to any disclaimer, the term of this patent is extended or adjusted under 35 U.S.C. 154(b) by 0 days.

(21) Appl. No.: 15/151,751

(22) Filed: May 11, 2016

(65) Prior Publication Data

US 2017/0002330 A1 Jan. 5, 2017

Related U.S. Application Data

(60) Provisional application No. 62/275,385, filed on Jan. 6, 2016, provisional application No. 62/198,502, filed on Jul. 29, 2015, provisional application No. 62/159,953, filed on May 11, 2015.

(51) Int. Cl.
| | | |
|---|---|---|
| *C12N 5/071* | (2010.01) | |
| *C12N 5/077* | (2010.01) | |
| *A61K 35/34* | (2015.01) | |
| *A61K 35/545* | (2015.01) | |
| *A61L 27/38* | (2006.01) | |

(52) U.S. Cl.
CPC ............ *C12N 5/0697* (2013.01); *A61K 35/34* (2013.01); *A61K 35/545* (2013.01); *A61L 27/3826* (2013.01); *A61L 27/3895* (2013.01); *C12N 5/0657* (2013.01); *A61L 2430/20* (2013.01); *C12N 2503/04* (2013.01); *C12N 2506/45* (2013.01); *C12N 2513/00* (2013.01); *C12N 2529/00* (2013.01)

(58) Field of Classification Search
CPC ............ C12N 5/0697; C12N 5/0657; C12N 2513/00; C12N 2503/04; C12N 2529/00; C12N 2506/45; A61K 35/34; A61K 35/545; A61L 27/3826; A61L 27/3895; A61L 2430/20

See application file for complete search history.

(56) References Cited

U.S. PATENT DOCUMENTS

| | | |
|---|---|---|
| 6,218,182 B1 | 4/2001 | Naughton et al. |
| 6,979,308 B1 | 12/2005 | MacDonald et al. |
| 7,198,940 B2 | 4/2007 | Vellinger et al. |
| 7,604,987 B2 | 10/2009 | Hutmacher et al. |
| 8,492,140 B2 | 7/2013 | Smith et al. |
| 2004/0132184 A1* | 7/2004 | Dennis ................ C12N 5/0658 435/366 |
| 2014/0094388 A1 | 4/2014 | Wakatsuki |

FOREIGN PATENT DOCUMENTS

| | | | |
|---|---|---|---|
| WO | 2013184527 A1 | 12/2013 | |
| WO | 2014085933 A1 | 6/2014 | |
| WO | 2014201254 | 12/2014 | |
| WO | WO-2015054383 A1 * | 4/2015 | ............ A61K 35/34 |
| WO | 2015061907 A1 | 5/2015 | |
| WO | 2015084168 A1 | 6/2015 | |

OTHER PUBLICATIONS

Shamir and Ewald "Three-dimensional organotypic culture: experimental models of mammalian biology and disease." Nat Rev Mol Cell Biol. Oct. 2014;15(10):647-64. doi: 10.1038/nrm3873. Epub Sep. 17, 2014. (Year: 2014).*

Liau et al. "Pluripotent stem cell-derived cardiac tissue patch with advanced structure and function." Biomaterials. Dec. 2011;32(35): 9180-7 (Year: 2011).*

Ronaldson et al. "p. 431: Human iPS Cell Based Cardiac Microtissue Platform for Predictive Toxicity Studies" issue Engineering Part A.Dec. 2014. Published in vol. 20 Issue S1: Dec. 3, 2014 (Year: 2014).*

Stevens et al. "Physiological function and transplantation of scaffold-free and vascularized human cardiac muscle tissue." Proc Natl Acad Sci U S A. Sep. 29, 2009; 106(39): 16568-16573. (Year: 2009).*

The International Search Report and Written Opinion dated Sep. 1, 2016 in Application No. PCT/US2016/031768.

Tulloch et al., Growth of engineered human myocardium with mechanical loading and vascular coculture. Circulation Research. 2011, vol. 109, pp. 47-59.

Eschenhagen et al., Cardiac tissue engineering. Transpl Immunol. May 2002, vol. 9, No. 2-4, pp. 315-321.

Masutani et al., Levosimendan restores the positive force-frequency relation in heart failure. Am J Physiol Heart Circ Physiol. Aug. 2011, vol. 301, No. 2, pp. H488-H496.

Yazawa et al., Using induced pluri potent stem cells to investigate cardiac pheno-types in Timothy syndrome. Nature. Mar. 10, 2011, vol. 471, No. 7337, pp. 230-234 (author's manuscript pp. 1-10).

Sebastian Schaaf, Aya Shibamiya, Marco Mewe, Alexandra Eder, Andrea Stöhr, Marc N. Hirt, Thomas Rau, Wolfram-Hubertus Zimmermann, Lenard Conradi, Thomas Eschenhagen, Arne Hansen, Human Engineered Heart Tissue as a Versatile Tool in Basic Research and Preclinical Toxicology, PLoS ONE Oct. 20, 2011 6(10): e26397, https://doi.org/10.1371/journal.pone.0026397.

(Continued)

*Primary Examiner* — Titilayo Moloye
(74) *Attorney, Agent, or Firm* — Reed Smith LLP; Lisa A. Chiarini; Walter M. Egbert, III

(57) ABSTRACT

A cardiac organoid containing 3-D matter of adult human heart tissue.

27 Claims, 81 Drawing Sheets
(61 of 81 Drawing Sheet(s) Filed in Color)
Specification includes a Sequence Listing.

(56) References Cited

OTHER PUBLICATIONS

Caspi O, Lesman A, Basevitch Y, Gepstein A, Arbel G, Habib IH, Gepstein L, Levenberg S., Tissue Engineering of Vascularized Cardiac Muscle from Human Embryonic Stem Cells, Circulation Research Jan. 11, 2007; 100: pp. 263-272.

L. T. Shenje, P. Andersen, M. K. Halushka, C. Lui, L. Fernandez, G. B. Collin, N. Amat-Alarcon, W. Meschino, E. Cutz, K. Chang, R. Yonescu, D. A. S. Batista, Y. Chen, S. Chelko, J. E. Crosson, J. Scheel, L. Vricella, B. D. Craig, B. A. Marosy, D. W. Mohr, K. N. Hetrick, J. M. Romm, L. F. Scott, D. Valle, J. K. Naggert, C. Kwon, K. F. Doheny, D. P. Judge, Mutations in Alström Protein Impair Terminal Differentiation of Cardiomyocytes, Nature Communications, Mar. 4, 2014, vol. 5, Article No. 3416.

Li H, Sun S, Liu H, Chen H, Rong X, Lou J, Yang Y, Yang Y, Liu H, Use of a biological reactor and platelet-rich plasma for the construction of tissue-engineered bone to repair articular cartilage defects, Exp. Ther. Med. Aug. 2016, vol. 12(2) pp. 711-719.

Masuda S, Shimizu T, Three-dimensional cardiac tissue fabrication based on cell sheet technology, Adv. Drug Deliv. Rev. Jan. 2016, vol. 96 pp. 103-109.

Ramachandran SD, Schirmer K, Munst B, Heinz S, Ghafoory S, Wolfl S, Simon-Keller K, Marxa Oie CI, Ebert MP, Walles H, Braspenning J, Breitkopf-Heinlein K, In Vitro Generation of Functional Liver Organoid-Like Structures Using Adult Human Cells, PLoS One, Oct. 2015, vol. 10(10) pp. e0139345.

De Peppo GM, Vunjak-Novakovic G, Marolt D, Cultivation of human bone-like tissue from pluripotent stem cell-derived osteogenic progenitors in perfusion bioreactors, Methods Mol. Biol. 2014 vol. 1202 pp. 173-184.

Bhumiratana S, Bernhard JC, Alfi DM, Yeager K, Eton Re, Bova J, Shah F, Gimble JM, Lopez MJ, Eisig SB, Vunjak-Novakovic G, Tissue-engineered autologous grafts for facial bone reconstruction, Sci. Transl. Med. Jun. 2016, vol. 8(343) pp. 343ra83.

Ding M, Henrikesen SS, Wendt D, Overgaard S, An automated perfusion bioreactor for the streamlined production of engineered osteogenic grafts, J. Biomed. Mater. Res. B Appl. Biomate., Apr. 2016,vol. 104(3) pp. 532-537.

Figallo E, Cannizzaro C, Gerecht S, Burdick JA, Langer R, Elvassore N, Vunjak-Novakovic G, Micro-bioreactor array for controlling cellular environments, Lab Chip, Jun. 2007, vol. 7(6) pp. 710-719.

Hansmann J, Groeber F, Kahlig A, Kleinhans C, Walles H., Bioreactors in tissue engineering—principles, applications and commercial constraints. Biotechnol. J., Mar. 2013, 8(3) pp. 298-307.

Wang Z, Kim K., Organ-on-a-Chip Platforms for Drug Screening and Tissue Engineering, Biomedical Engineering Frontier Research and Converging Technologies, Jan. 2016, pp. 209-233.

The IPRP mailed Sep. 29, 2017 in Application No. PCT/US2017/041996.

Elisa Cimetta, Elisa Figallo, Christopher Cannizzaro, Nicola Elvassore, and Gordana Vunjak-Novakovic, Microbioreactor arrays for controlling cellular environments: design principles for human embryonic stem cell applications Methods. Feb. 2009 ; 47(2): 81-89.

Meyvantsson I, Beebe DJ. Cell culture models in microfluidic systems. Annu Rev Anal Chem (Palo Alto Calif). 2008;1:423-449.

* cited by examiner

High level system components

- Microtissue specific media reservoir array
  - Standard 48, 96 well plate
- Microtissue specific perfusate manifold for routing of a common perfusate
  - Cardiac, Bone, Liver, Skin
- Microtissue specific support structure
  - Cardiac, Bone, Liver, Skin
- Multi-perfusate routing manifold
- Electrodes for cardiac tissue

FIGURE 15A

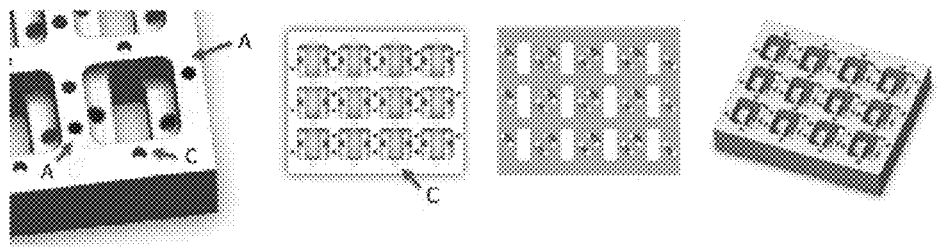

Tissue reservoir array follows standard well plate pattern spacing (e.g. 48 well plate, 96 well)

A) Top-level access to media exchange (in/out ports) for individual wells
B) Two fluidic paths at different heights within each well for constant-volume/height media exchange within an open platform
C) Alignment features for installing modular microtissue manifolds
D) Alternate split design can accommodate carbon electrodes for electrical stimulation
E) Thin window at bottom allows imaging of microtissues

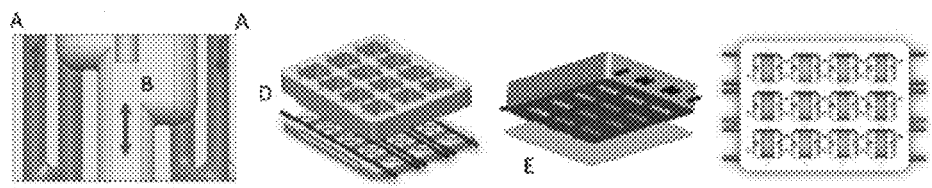

FIGURE 15B

Reservoir approaches

- Three main variants have been proposed with different methods of routing reservoir media
  - Integrated ports (left)
  - Integrated routing manifold (center)
  - Separate ports (right)

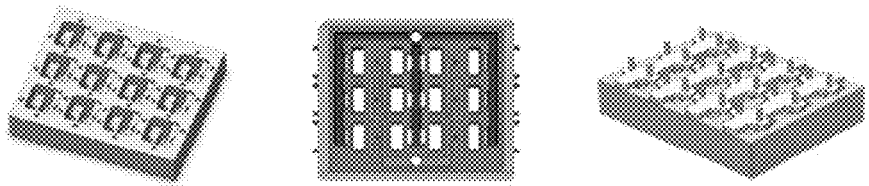

FIGURE 15C

Media flow distribution

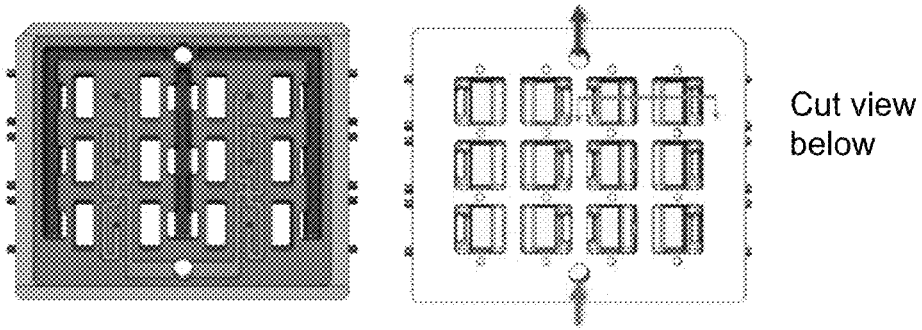

Cut view below

Green: media is distributed and flows into chamber at controlled rate

Red: media overflows from chamber and is withdrawn via vacuum

Blue: adhesive is applied to bond polycarbonate to glass slide

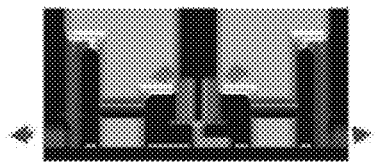

Cut view

FIGURE 15D

- Modular microtissue manifolds
  - Provide an inlet and outlet port to route a common perfusate through a lumen within the microtissue
  - Contains a means to attach to the microtissue and provide a leak free fluidic path into and out from the tissue lumen
- Additional tissue specific components within reservoir
  - Provide additional support to microtissue
  - Provide stimulation to microtissue (e.g. electrodes)

FIGURE 16A

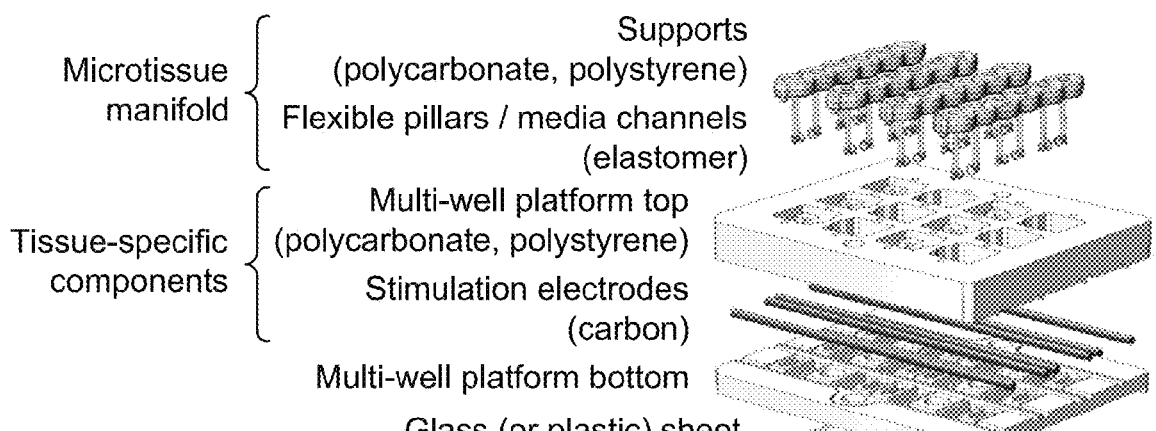

Microtissue manifold
- Supports (polycarbonate, polystyrene)
- Flexible pillars / media channels (elastomer)

Tissue-specific components
- Multi-well platform top (polycarbonate, polystyrene)
- Stimulation electrodes (carbon)

Multi-well platform bottom
Glass (or plastic) sheet

FIGURE 16B

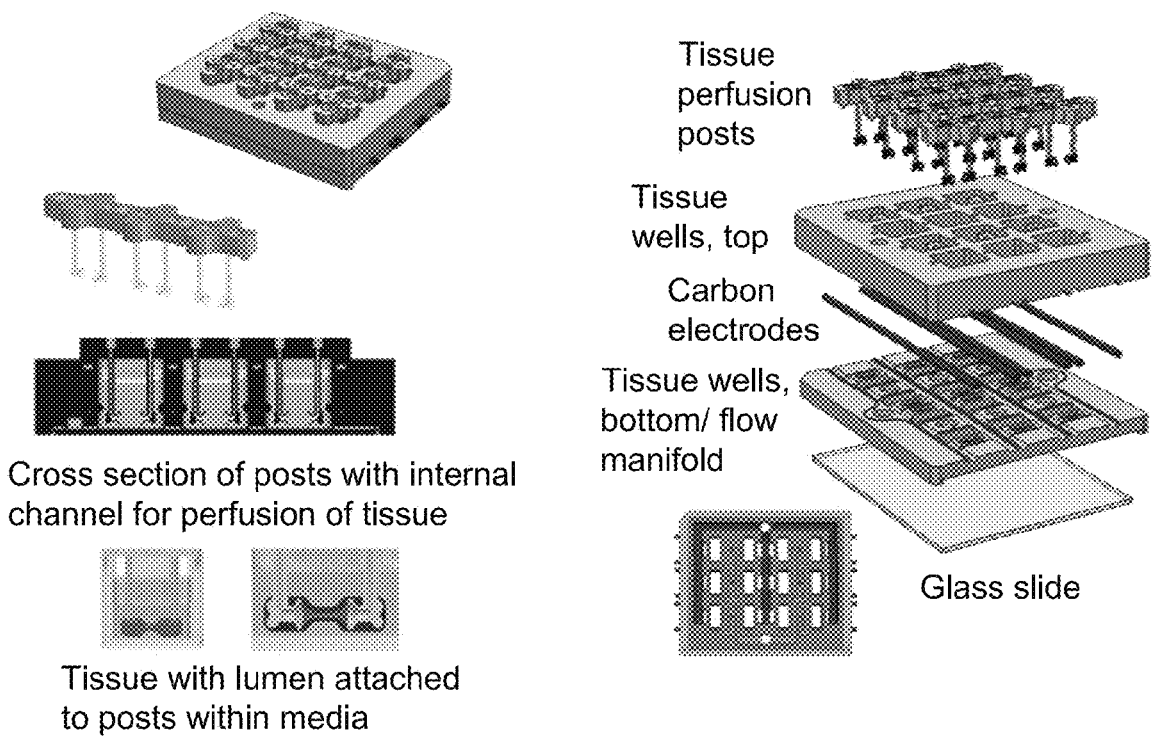

Cross section of posts with internal channel for perfusion of tissue

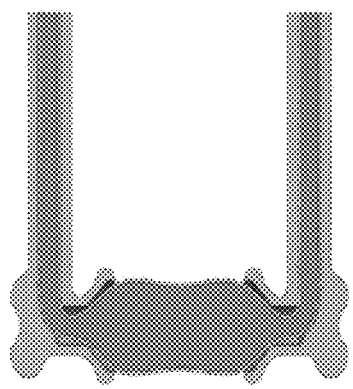

Tissue with lumen attached to posts within media

FIGURE 16E

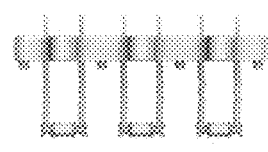

Inset-molded sacrificial material (orange) forms channels within elastomer (grey) posts.

Sacrificial material may also be coated with PDLGA (thin yellow layer) to minimize contact with tissue during initial organoid formation.

Sacrificial material is dissolved and purged from channel after initial formation to provide internal perfusion of media.

FIGURE 16F

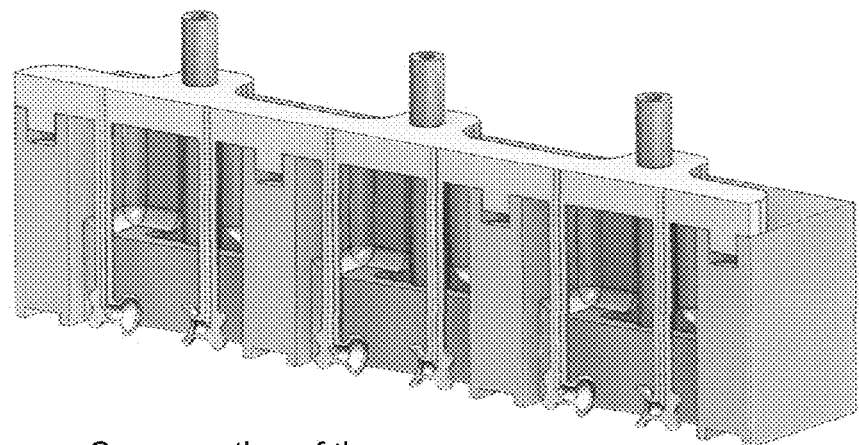
Cross section of tissue perfusion posts shown within wells
FIGURE 16I
Fabrication of cardiac tissue manifolds
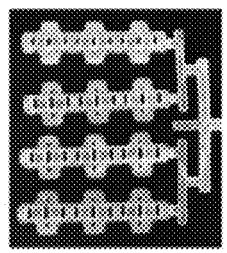
Injection molding of post support structure
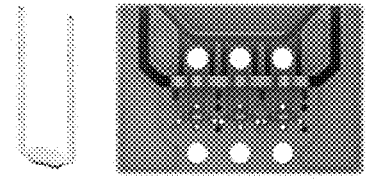
Incorporation of sacrificial inserts
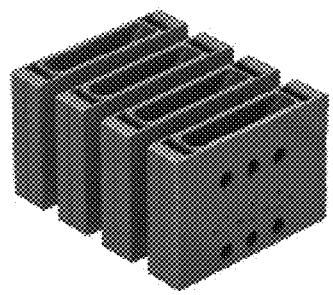
Centrifugal casting of elastomeric posts
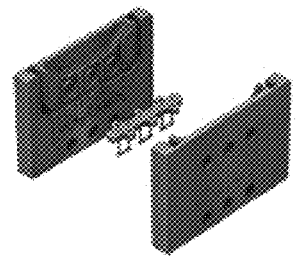
FIGURE 16J Multi-tissue platforms

- Fluid routing manifold
  - Bonded multi-layer microfluidic network
  - Interfaces with in/out ports of modular microtissue manifolds
  - May also interface with in/out ports of tissue reservoir array Cardiac differentiation of hiPS-CMs.

Fig. 20 A to I. Intensity Training Drives BEAM Maturation.
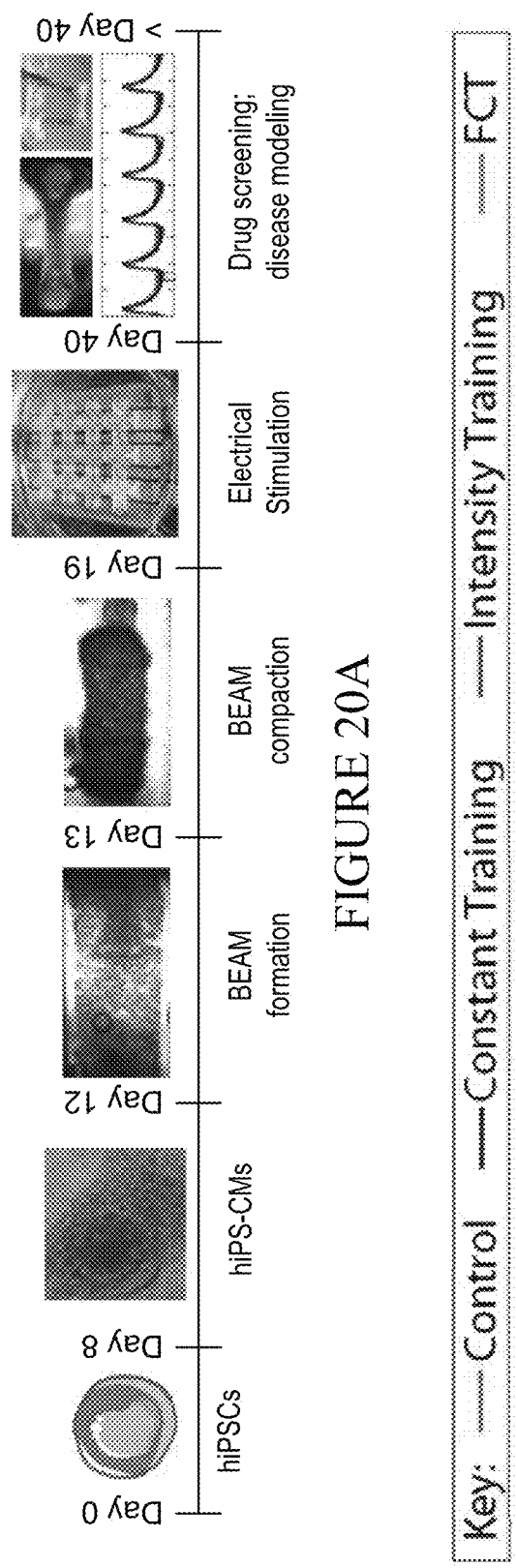
FIGURE 20A
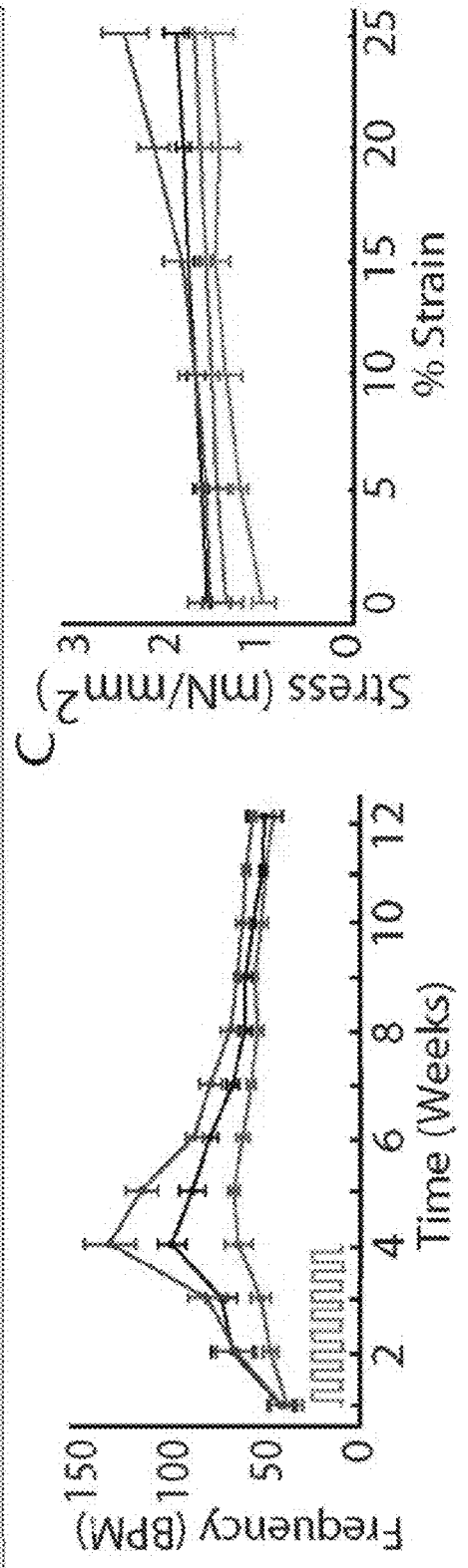
FIGURE 20B
FIGURE 20C

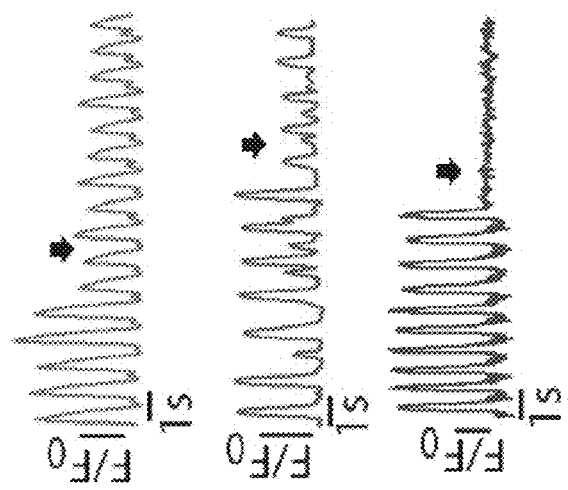
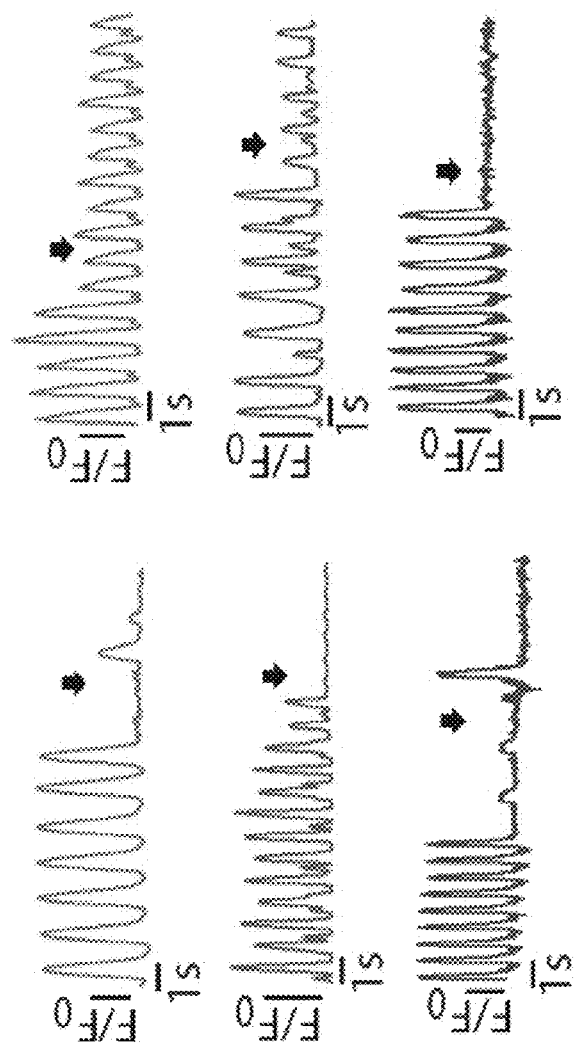
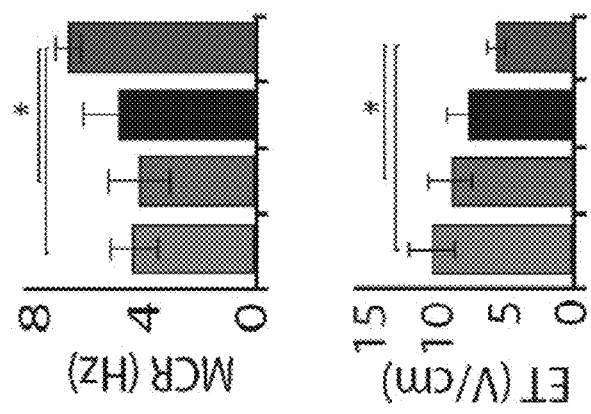

BEAM bioreactor and experimental design.
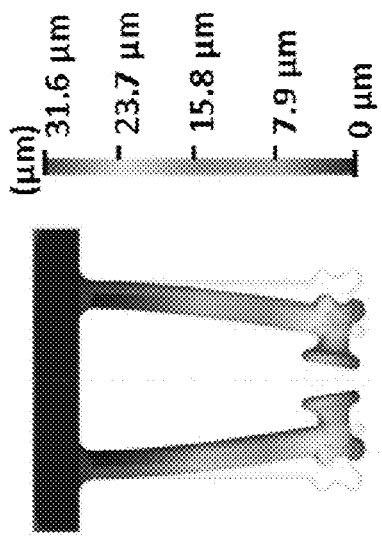
FIGURE 21D
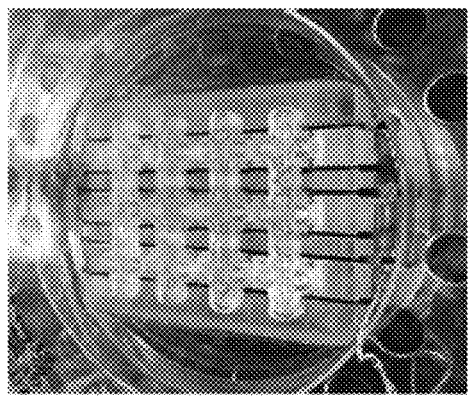
FIGURE 21C
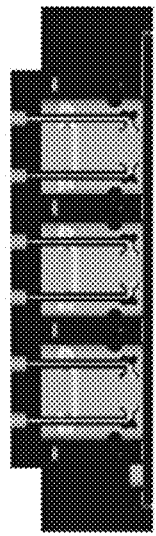
FIGURE 21A
FIGURE 21B
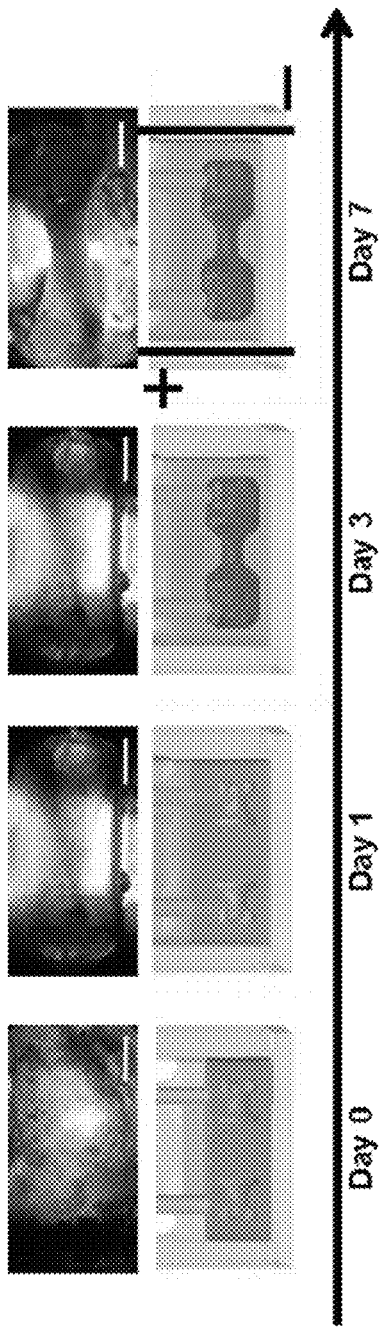
FIGURE 21E Intensity Training Enhances Gene Expression
and Ultrastructural Properties within BEAMs.
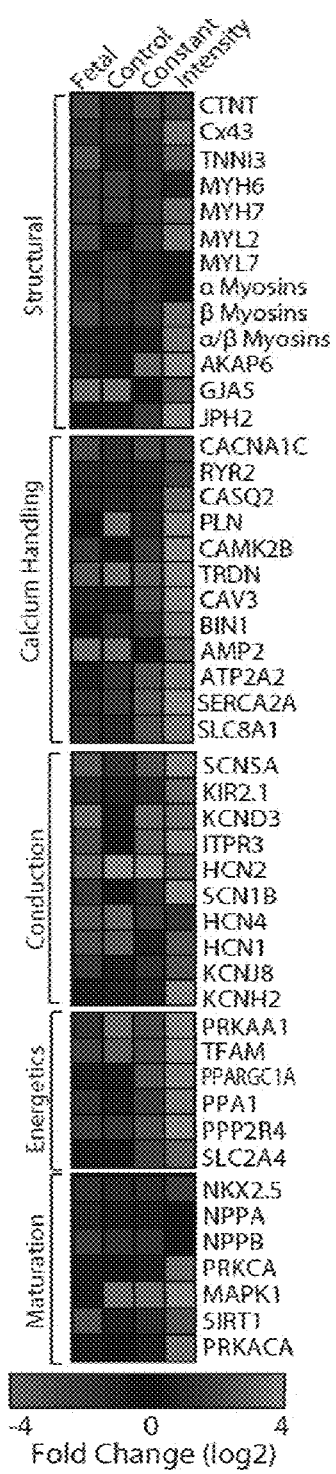
FIGURE 22A
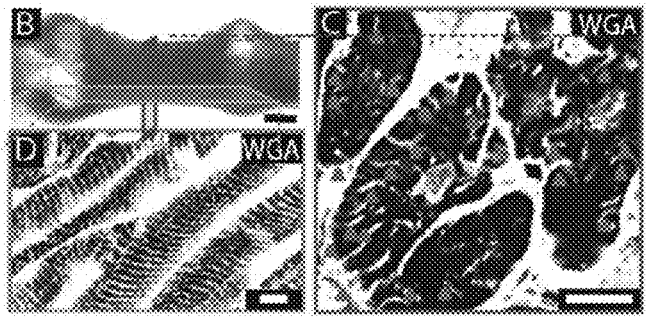
FIGURE 22B    FIGURE 22C
FIGURE 22D
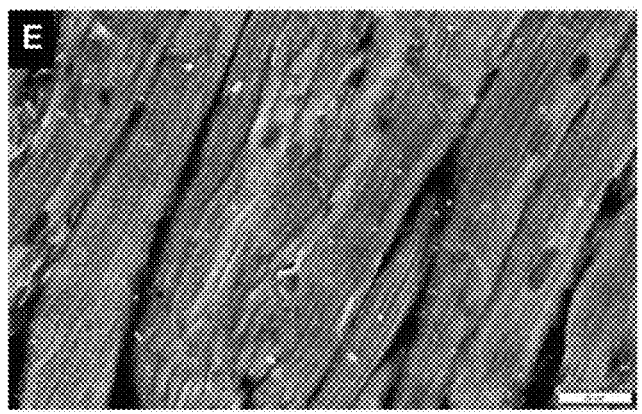
FIGURE 22E
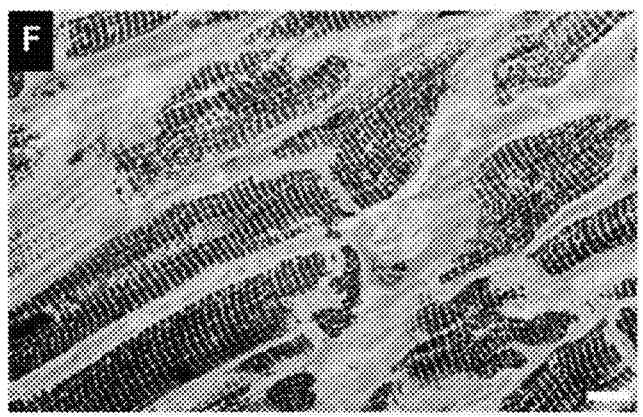
FIGURE 22F

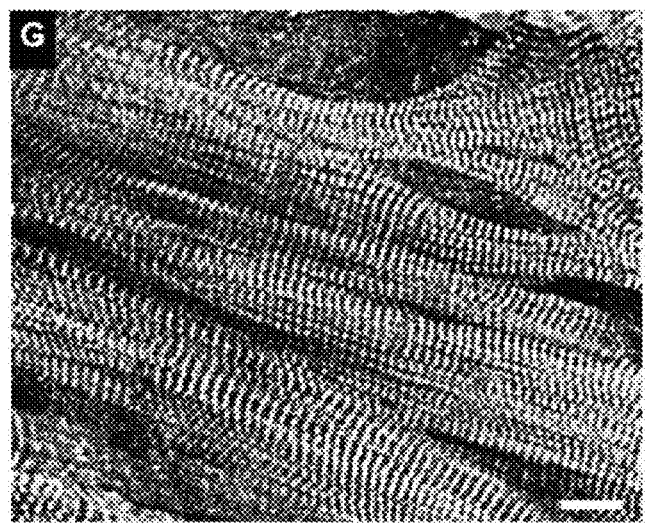
FIGURE 22G
FIGURE 22H          FIGURE 22I
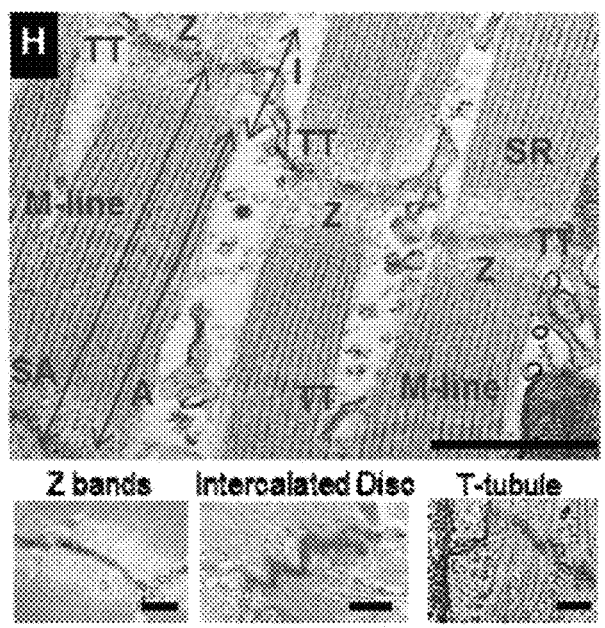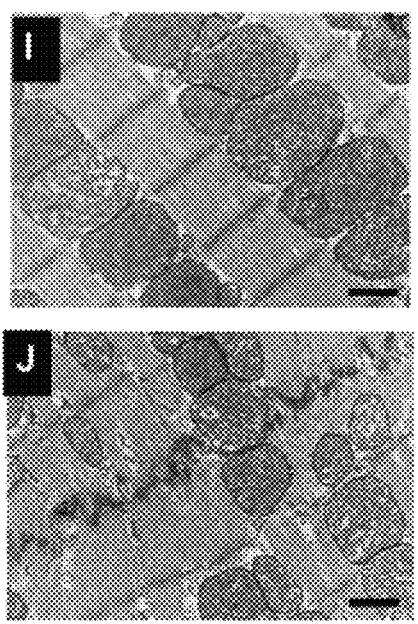
FIGURE 22J Intensity Training Enables Predictive Cardiotoxicity Screening.

Physiologically Relevant Timothy Syndrome Disease Model.
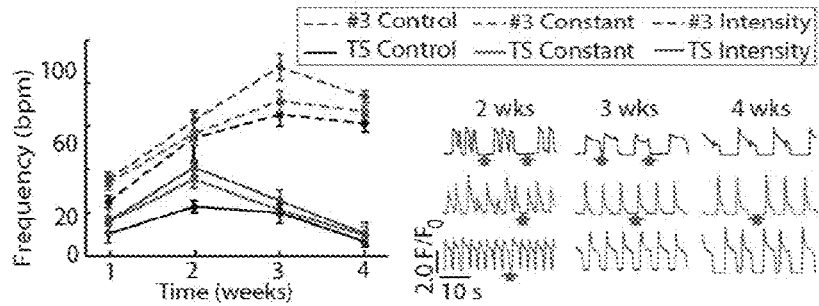
FIGURE 24A        FIGURE 24B
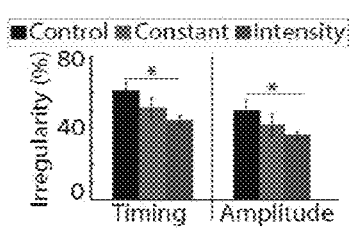   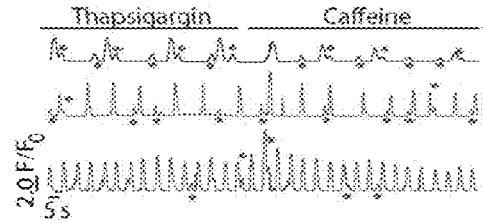
FIGURE 24C        FIGURE 24D
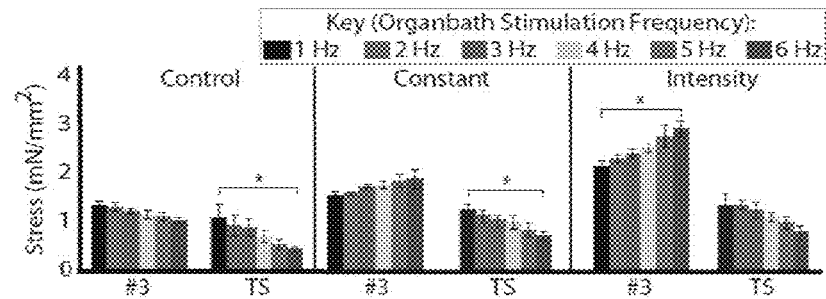
FIGURE 24E
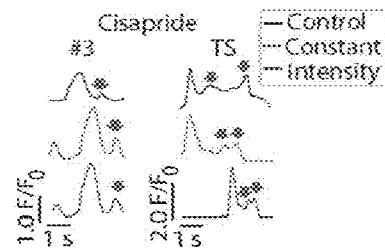   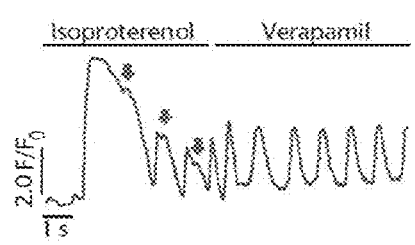
FIGURE 24F        FIGURE 24G
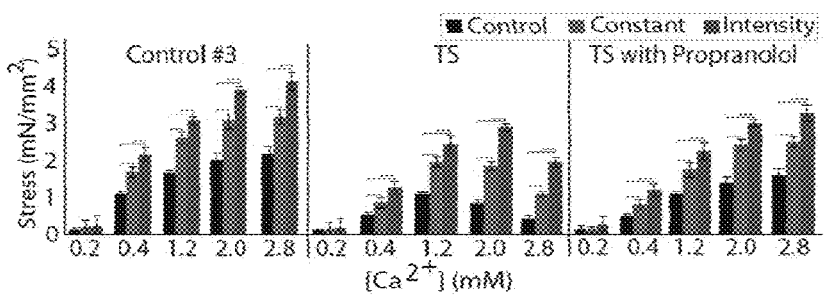
FIGURE 24H Enhanced maturation and functionality of BEAMs in response to training regimen as a function of time.

BEAM functionality and detraining over time.

Upregulation of calcium handling proteins via intensity training enhance functionality.

Physiological hypertrophy within BEAMs.

Increased calcium handling via intensity training over time.

Axial t-tubule immunostains.

Molecular structure within intensity trained BEAMs.
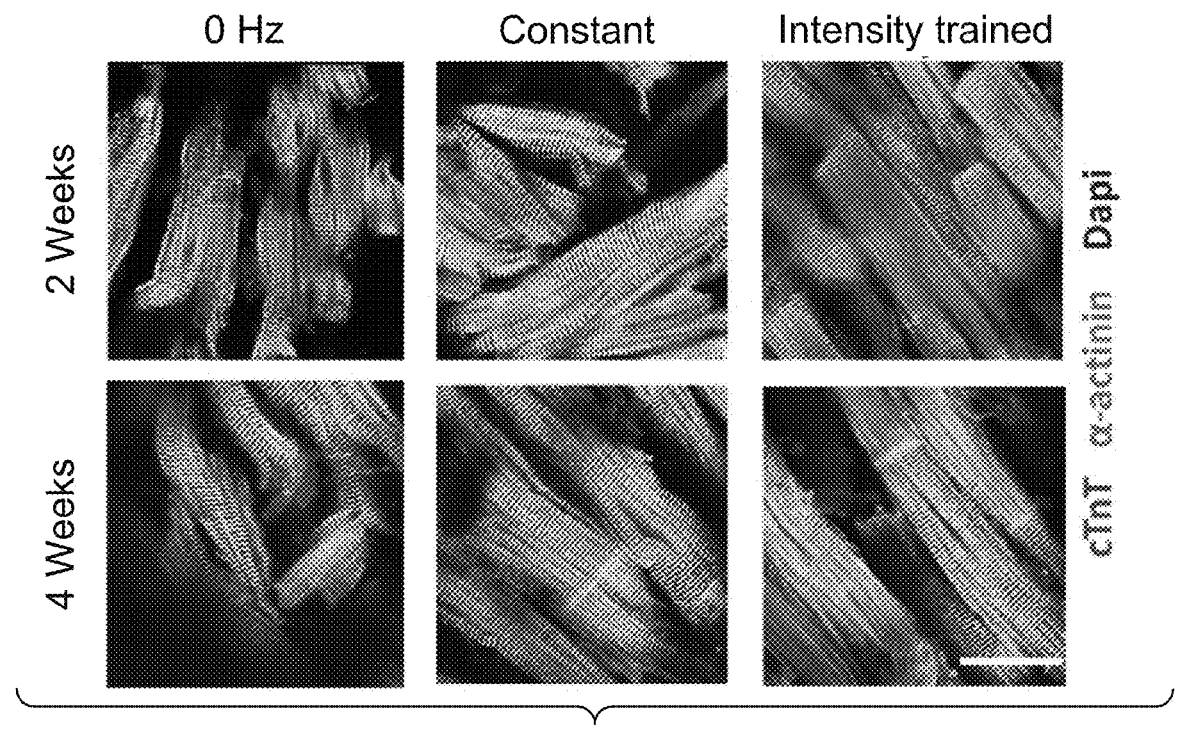
FIGURE 32A
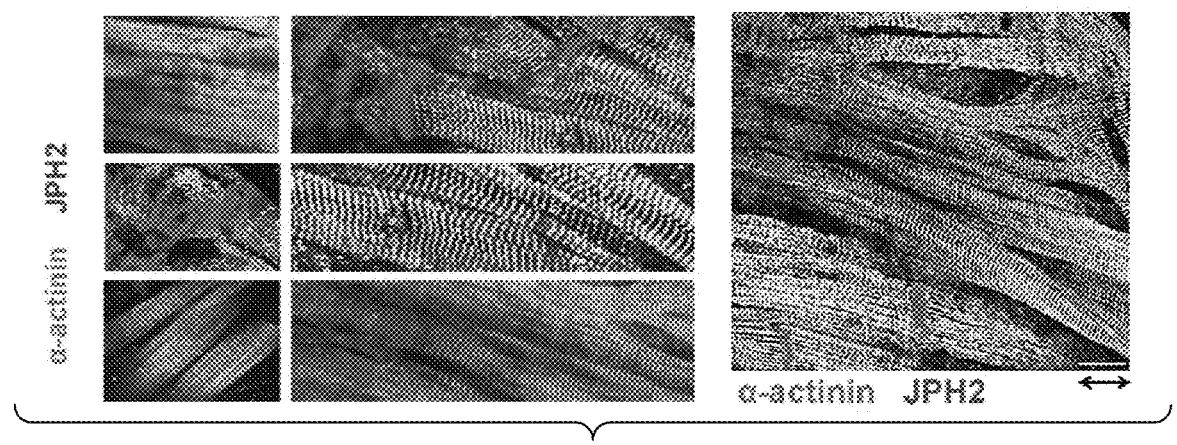
FIGURE 32B
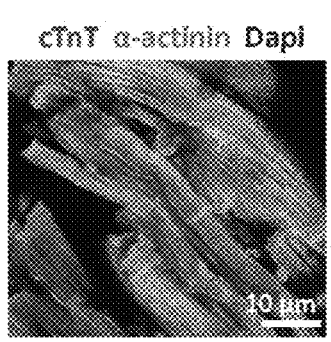 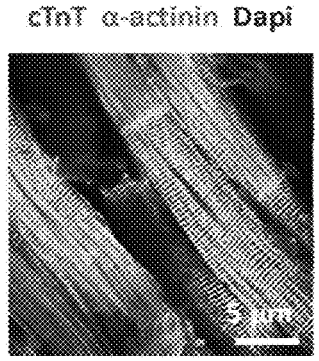 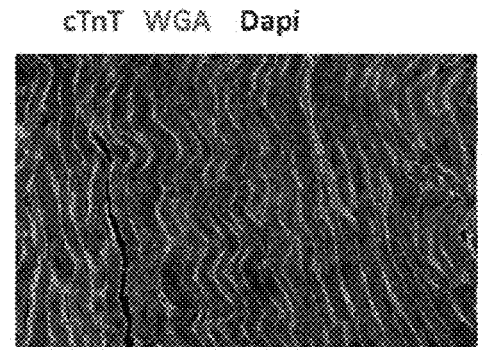
FIGURE 32C        FIGURE 32D        FIGURE 32E Detailed TEM images of intensity-trained BEAMs.

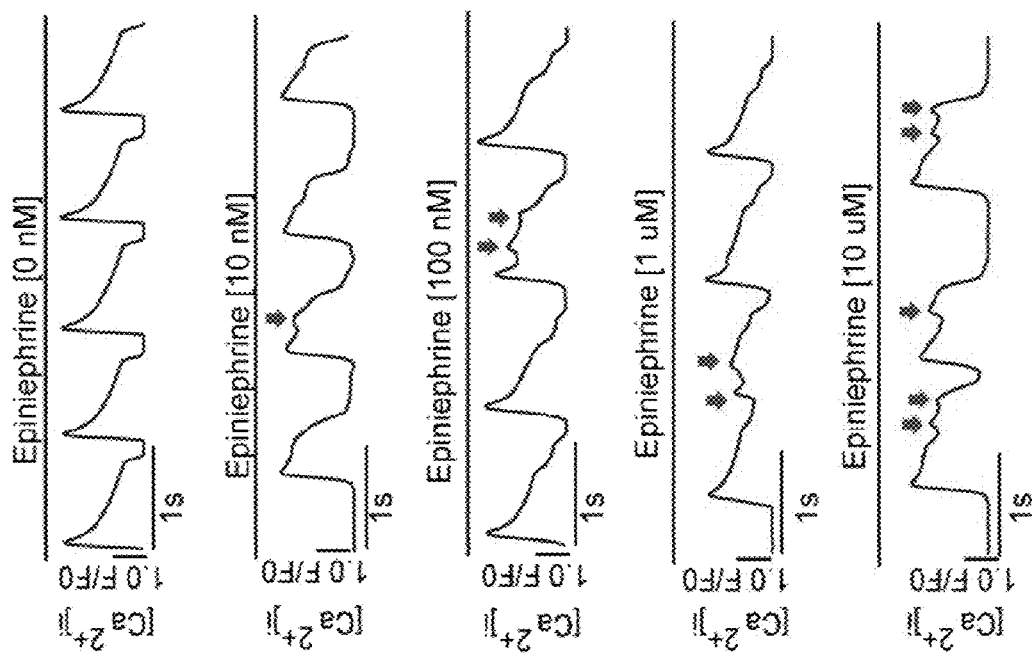
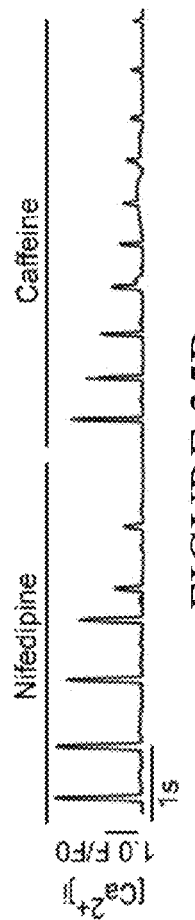
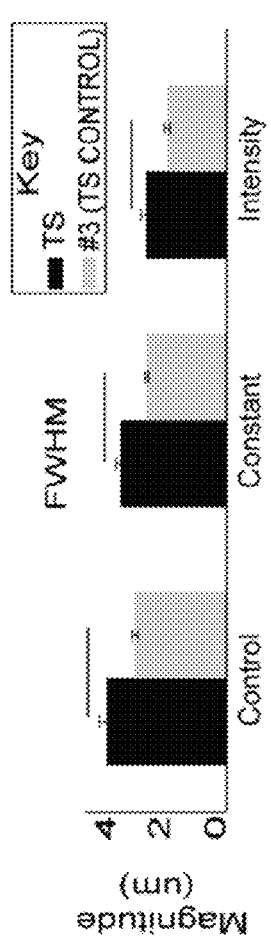
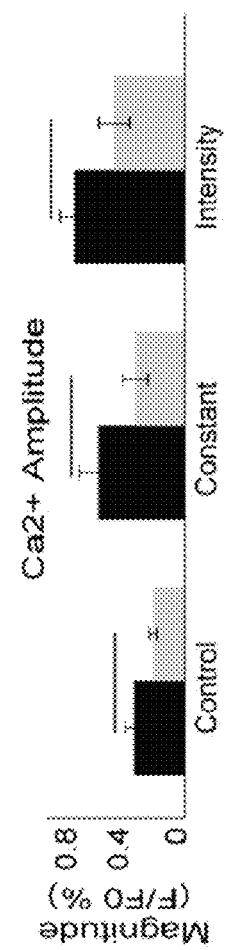
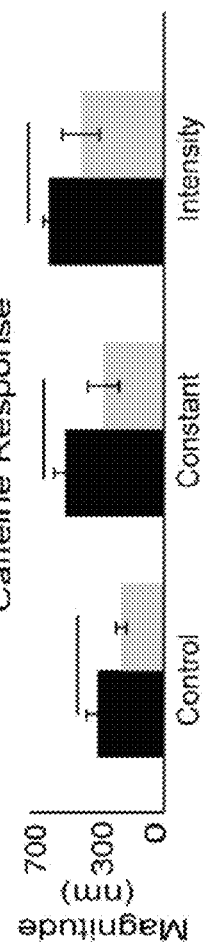
FIGURE 35D
FIGURE 35E
FIGURE 35F
FIGURE 35G
FIGURE 35C WGA cTnT DAPI
Intensity Trained, Week 4
Longitudinal Section, 100x

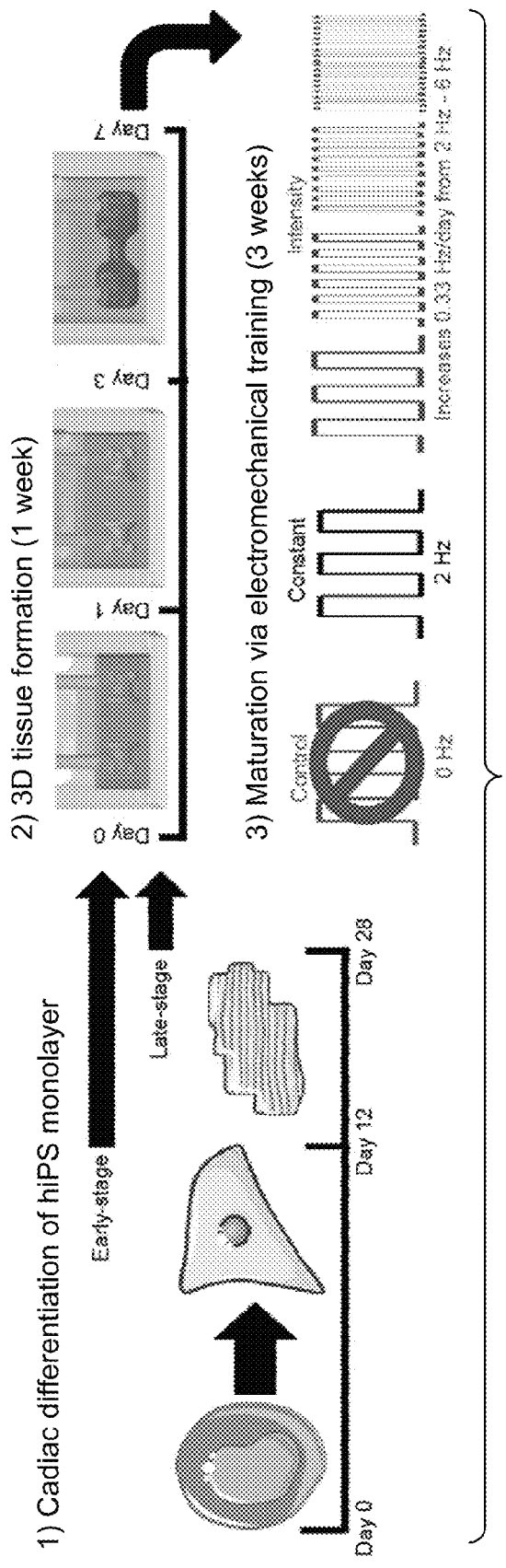
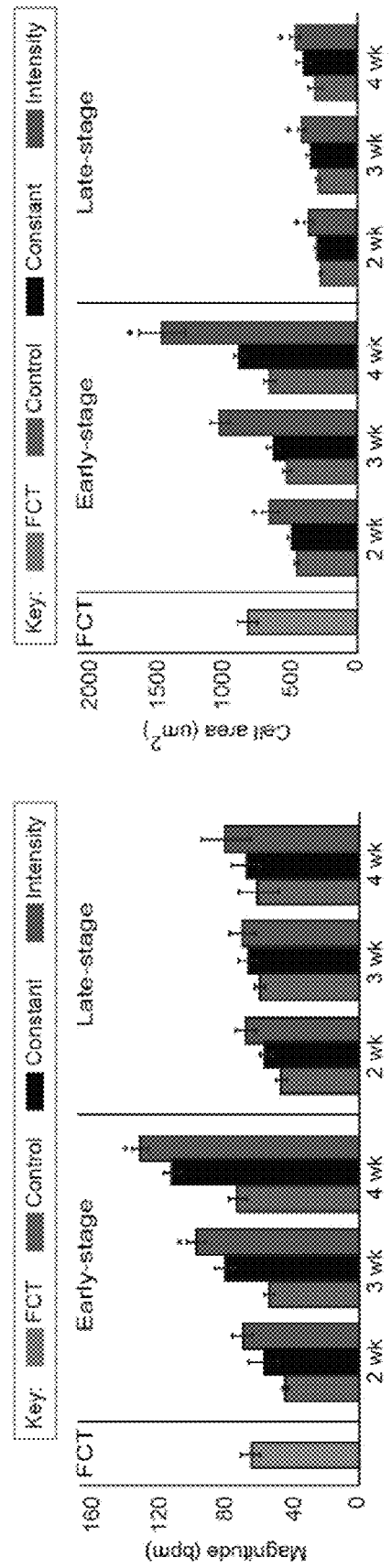
FIGURE 45A
FIGURE 45B
FIGURE 45C

Ultrastructural features.
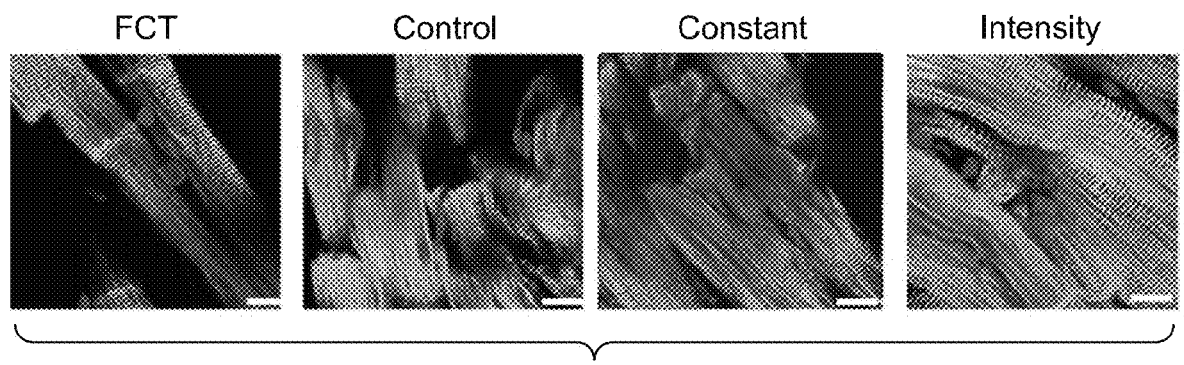
FIGURE 46A
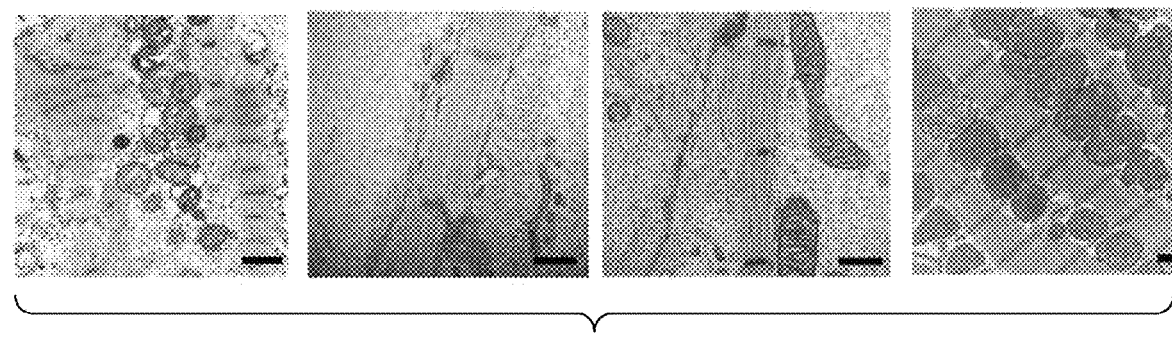
FIGURE 46B
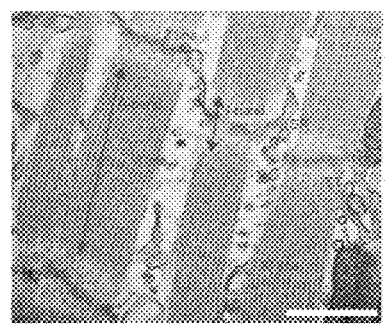 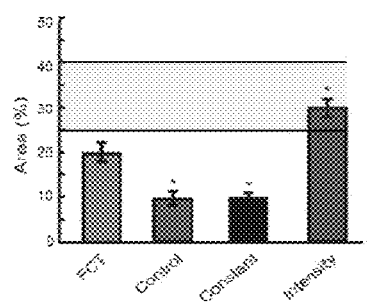 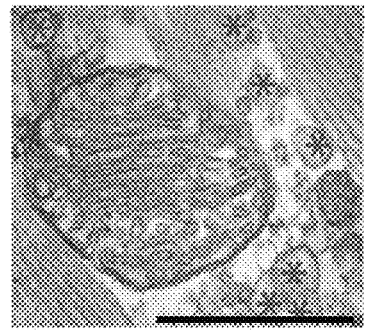
FIGURE 46C           FIGURE 46D           FIGURE 46E

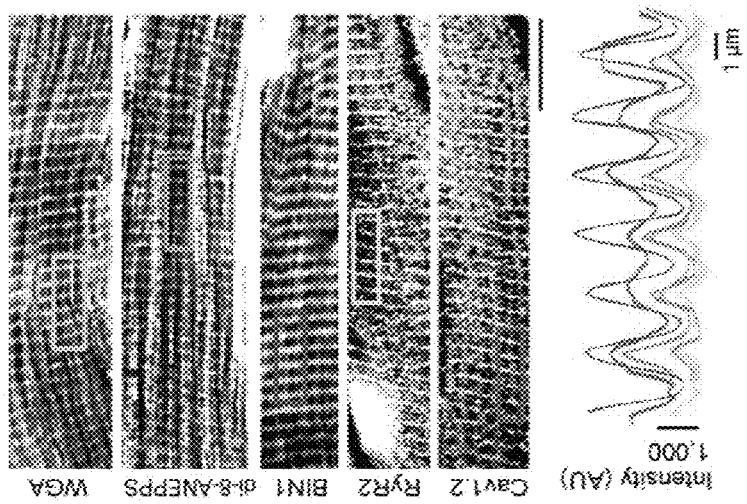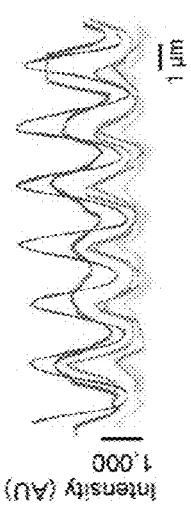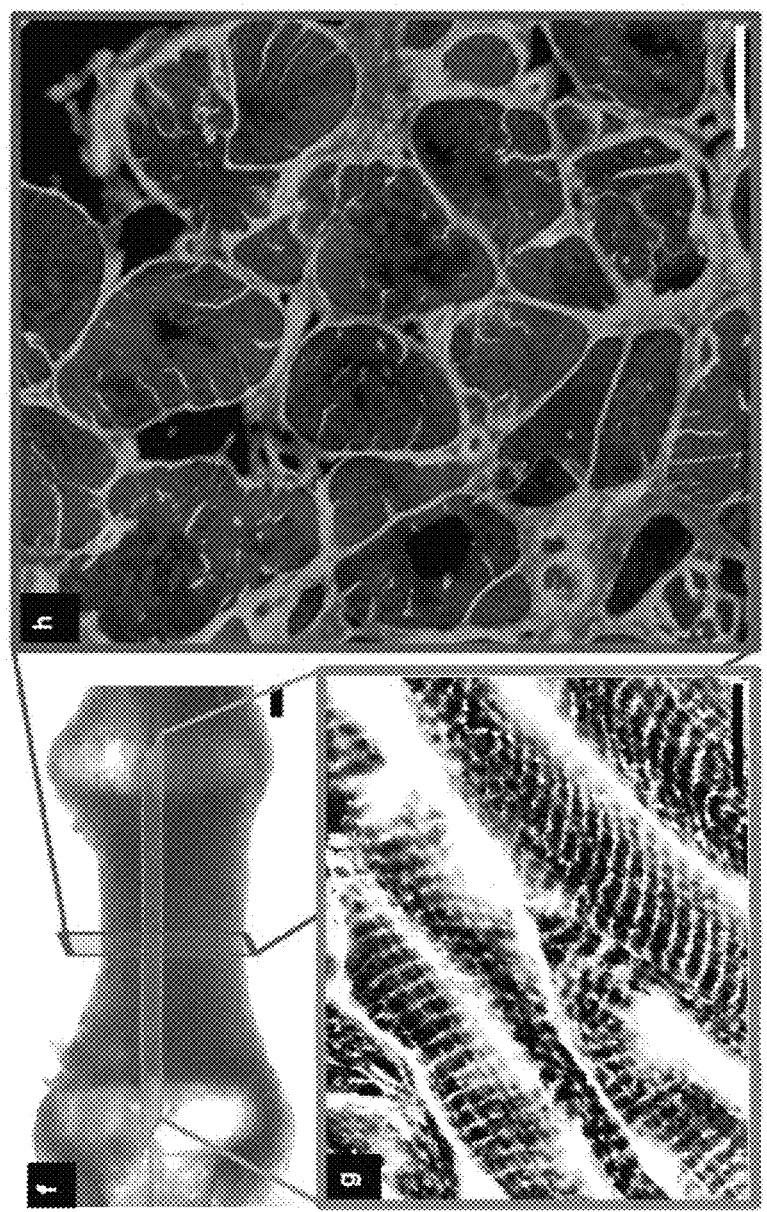
FIGURE 46I
FIGURE 46J
FIGURE 46H
FIGURE 46F
FIGURE 46G

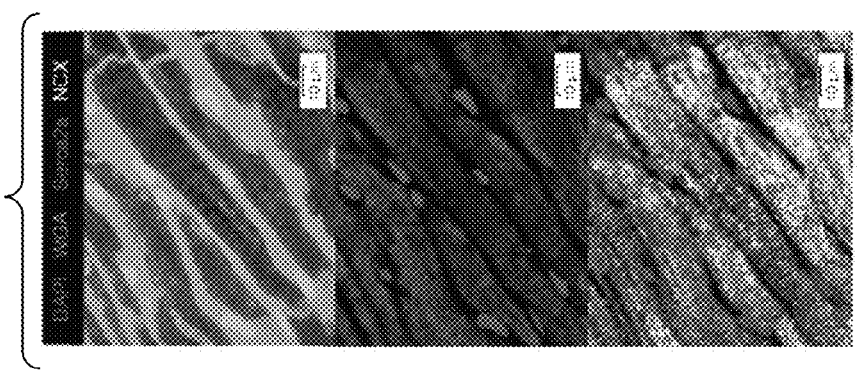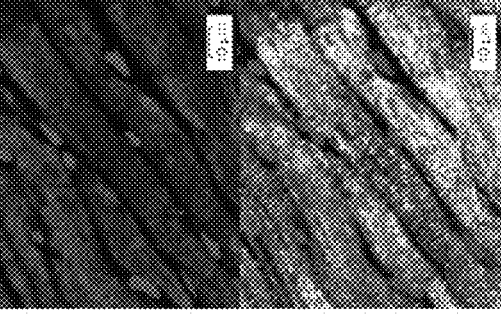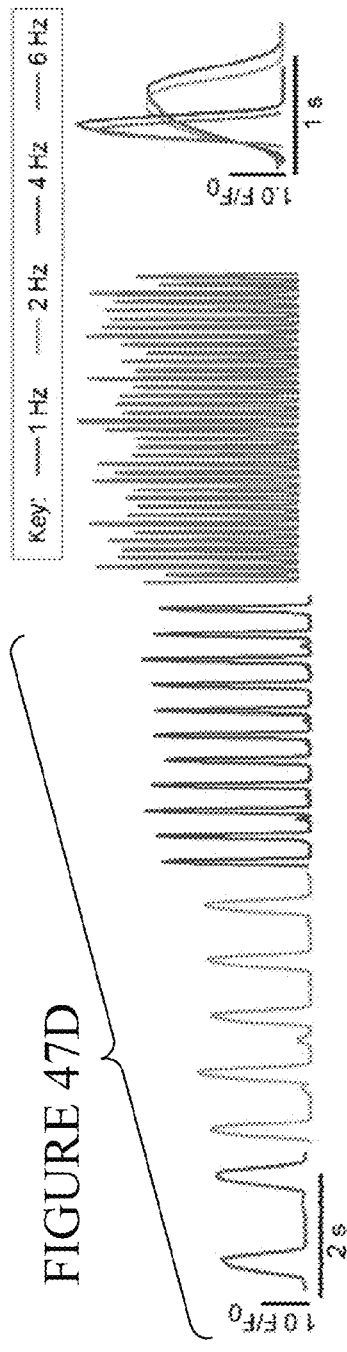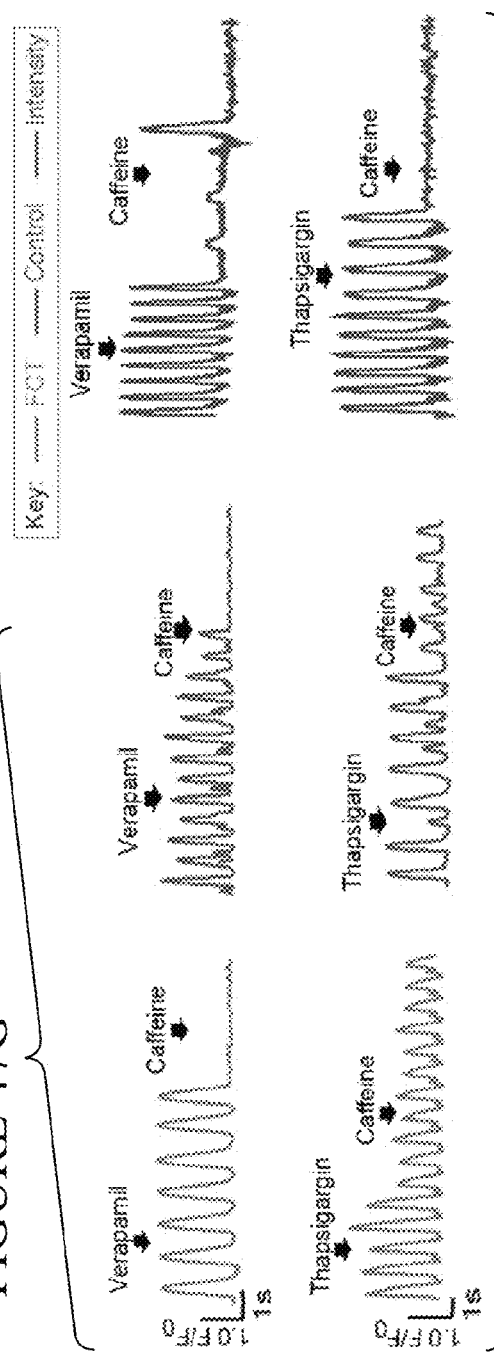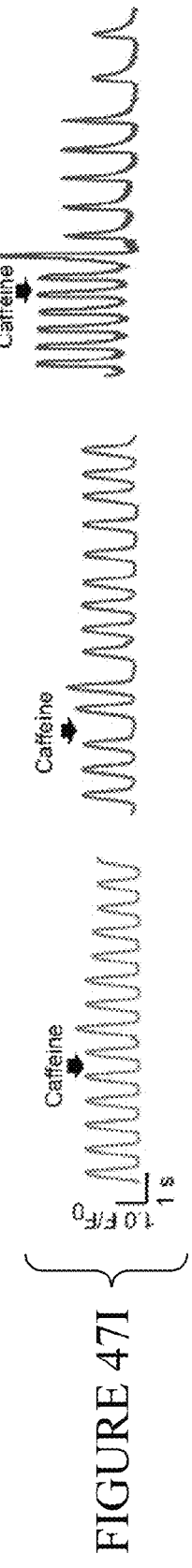

Intensity training of early-stage hiPS-CMs is required to enhance mitochondrial development.

Early-stage intensity-trained organoid, 2 weeks

Late-stage, 2 weeks

Isoproterenol Toxicity:
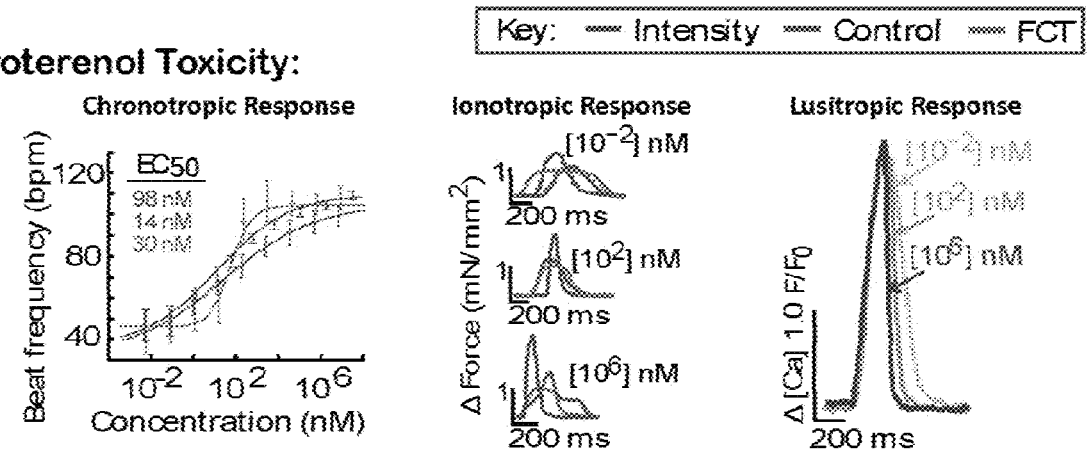
Drug testing:
| Drug | Drug EC$_{50}$ values | | |
|---|---|---|---|
| | FCT | Control | Intensity |
| Isoproterenol | 30 nM | 14 nM | 98 nM |
| Epinephrine | 11 nM | 900 nM | 18000 nM |
| Caffeine | 83 nM | 1200 nM | 1900 nM |
| Propranolol | 304 nM | 460 nM | 720 nM |
| E-4031 | 316 nM | 261 nM | 10 nM |
| Cisapride | 710 nM | 308 nM | 180 nM |
Maturation enables prediction of proarrythmia upon Cisapride exposure:
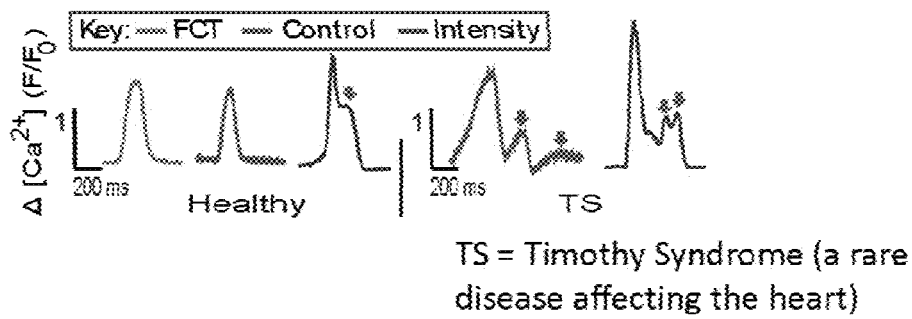
TS = Timothy Syndrome (a rare disease affecting the heart)
FIGURE 51

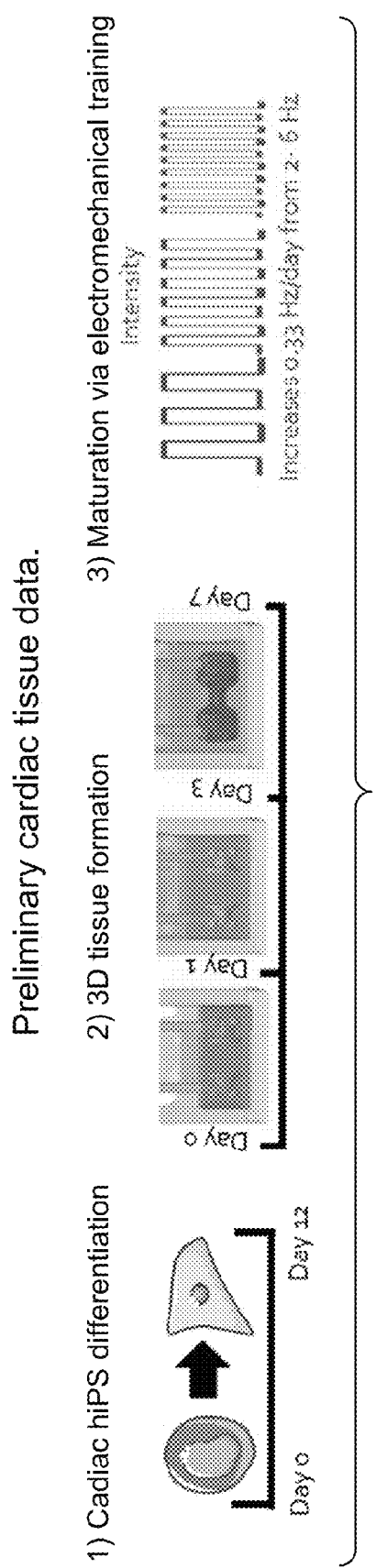
FIGURE 53A
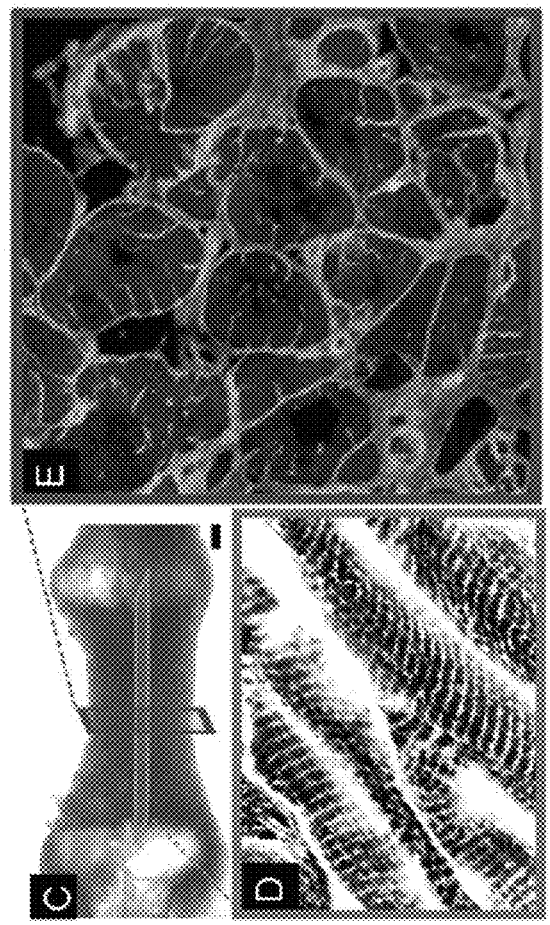
FIGURE 53C
FIGURE 53D
FIGURE 53E
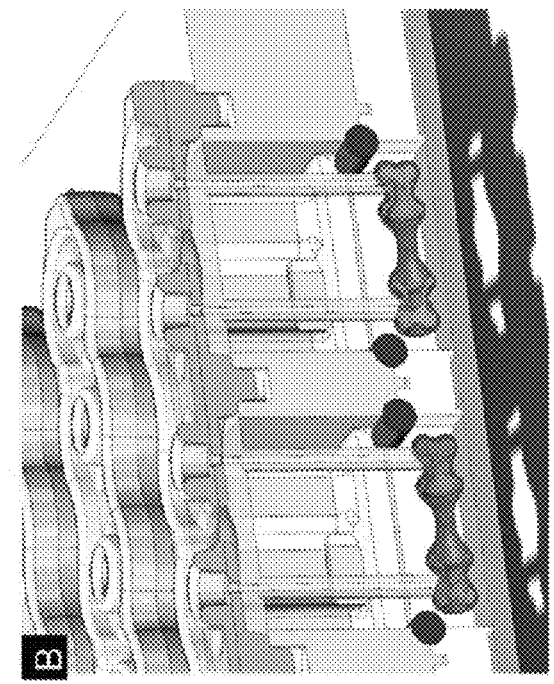
FIGURE 53B

| Baseline (B) | Moderate Intensity Interval Training (M) | Prolonged Moderate Intensity Interval Training (ML) | High Intensity Interval Training (H) |
|---|---|---|---|
| Constant Stimulation | 60% increase for 1 hour | 60% increase for 2 hours | 90% increase for 1 hour |
| 0 Hz | 0 Hz | 0 Hz | 0 Hz |
| 1 Hz | 1.6 Hz | 1.6 Hz | 1.9 Hz |
| 2 Hz | 3.2 Hz | 3.2 Hz | 3.8 Hz |
| 3 Hz | 4.8 Hz | 4.8 Hz | 5.7 Hz |
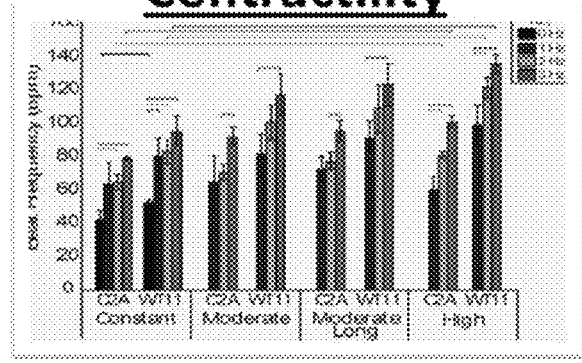
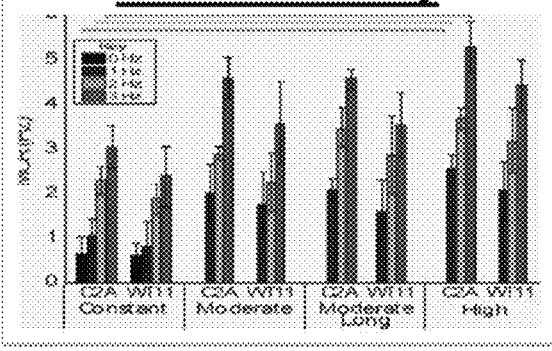
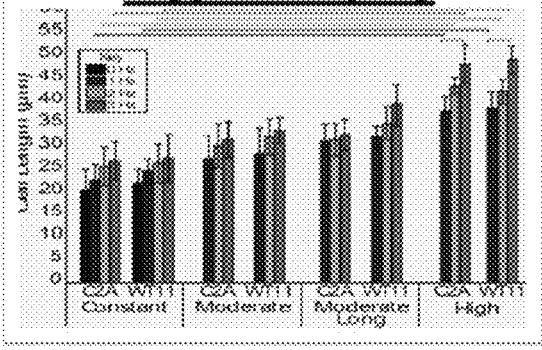
FIGURE 56

SEQUENCE LISTING

```
<160> NUMBER OF SEQ ID NOS: 82

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acagagcgga aaagtgggaa g                                                   21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgttgatcc tgtttcggag a                                                   21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtgactgga gcgccttag                                                      19
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgcacatga gagattggga                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatagagaga ctcctgcggc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccgtcttccc attctcggtt                                              20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcgtgcctga tgacaaacag gagt                                         24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atactcggtc tcggcagtga cttt                                         24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgggcgagt gaacgtgaaa a                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccgaacgtaa tcagccttca g                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gcccaacgtg gttcttccaa                                                20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ctcctcctct gggacactc                                                 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
agttctccct aaagctgctg t                                              21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tctgcctagt gtagttgcca tt                                             22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
agagtgtgaa gaagcccacg                                                20

<210> SEQ ID NO 16

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aacagatgcc aaaacttctg ct                                              22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actctggctc ctggaacttt g                                               21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgccccttg gtctctatg                                                  19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcatagctga tcggttcatg tcc                                             23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagttgtctt ggtggtctct c                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catcaagcac actgatcccg t                                               21

<210> SEQ ID NO 22
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccactcccat agctttccca g                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgattccaac gccaccaatt c                                           21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggagtcca taggcgatta ct                                          22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catcgaacac tcctctacgg a                                           21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggacacgcta actaagatga ggt                                         23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cattgccatc cccaacaaac c                                           21

<210> SEQ ID NO 28
<211> LENGTH: 21
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 28
agagtgggtc tttggtgttc c                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
acctcactcg ctcagctata a                                              21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
catcacgatg atacagatca gca                                            23

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gcacaccagg ctacctgtc                                                 19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
catacgcctc tttgcgaagg                                                20

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tcacagaaga catagtgacg acg                                            23

<210> SEQ ID NO 34
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 34
tggcaataga gcttgctgaa a                                              21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaccccaaga acattaacga gg                                             22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggacaacaga cggtagcacc                                                20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgaggcaaa caagatcgca g                                              21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgtgacttga tgtcggggaa                                                20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgagcagtgc gtccagaatt t                                              21

<210> SEQ ID NO 40
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 40
cgatcttgtt tgcctcatcc c                                              21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agctggctga tgtgatggtc                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cacttgtgcc ttaggttgcc                                                20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtgcgaacca accgctaca                                                 19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccagcgaatg tccacacac                                                 19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccaagcagac taagcaggac a                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
acactgccat acttcacgac a                                            21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agaagggcat tgactccgag                                              20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tagcggatca ggcgtgaga                                               19

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcctgcgcta tgagaatgag g                                            21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tggtgttgtg ctcgtagttt tc                                           22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
catgccaccg ctttaatcca g                                            21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 52
attgtagcca ccagtttccg a                                              21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtgattgccg tccgaaatgg                                                20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agttggtgaa taggaaccac ct                                             22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caacctgggc gaccagatag                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggtgttggga gagacgttgc                                                20

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttgaaacctg aaaatgtcct gct                                            23

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 58
ggtgagccac aacttgttct t                                                 21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atggcgtttc tccgaagcat                                                   20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tccgccctat aagcatcttg a                                                 21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gctttctggg tggactcaag t                                                 21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gagggcaatc cgtcttcatc c                                                 21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccctggagta ccgagtcttc c                                                 21

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
```
catttttgca ttagaccagc gtg          23

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
tctcaggcat acgctgacta c          21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ggagactctg tactcgaagg t          21

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
atccttggac gattcctcat tgg          23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
caggtgagtg ggagcaatct          20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ccaaggaccc tagagccgaa          20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ataggcgggg taggcgttat                                                20

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caacgcagac ctgatggatt t                                              21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agcccccgct tcttcattc                                                 19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tggaaacgtc cgggttacag                                                20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctgatccggt ccatcttcct                                                20

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tggacttatc catcaaggga tga                                            23

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agtgtgatcc attccgcaga g                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tctggagcag tattacgacc c                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ctggctggaa tctagcagtc t                                              21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tagccttgtc agataaggaa gga                                            23

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acagcttcac agtcaacttt gt                                             22

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
caaggagacc gggaaccact a                                              21

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cattcagggt gtgttcgatc tg                                             22

ENGINEERED ADULT-LIKE HUMAN HEART TISSUE

CROSS REFERENCE TO RELATED APPLICATIONS

This application claims priority to U.S. Provisional Patent Application Ser. Nos. 62/159,953, filed May 11, 2015, 62/198,502, filed Jul. 29, 2015, 62/275,385 filed Jan. 6, 2016, and U.S. NonProvisional patent application Ser. No. 15/151,751 filed May 11, 2016, each of the contents are incorporated herein by reference in their entireties.

STATEMENT REGARDING FEDERALLY SPONSORED RESEARCH

This invention was made with government support under grant EB017103, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 22, 2016, is named 16-50081-US (501038_20457)_SL.txt and is 18,919 bytes in size.

TECHNICAL FIELD

The disclosed subject matter relates to engineered three-dimensional (3-D) human heart tissue (e.g., micro-sized tissue). More specifically, it relates to 3-D human tissue having ultrastructures and characteristics of adult human native tissue. The engineering approach to make the 3-D tissue is biomimetic and recapitulates conditions associated with native tissue development, remodeling and/or disease in a patient-specific manner. The engineering approach further enables the use of engineered tissues in form of microfluidic multi-tissue platforms designed to enable testing of drugs in tissues that are healthy and tissues that express inherited and acquired heart disease. The platforms are designed to enable measurement of key functional properties—such as the beating frequency, force of contraction, strain and stress, and calcium flux in real time using optical methods. Finally, the platform is configurable and allows incorporation of multiple tissue types connected to each other by perfused microfluidic conduits established to recapitulate key interactions of interest for drug testing and modeling of disease.

BACKGROUND

Cardiovascular disease continues to be the leading cause of death in developed countries, and there is a need for developing more effective approaches to modeling disease and evaluating new treatment modalities. The current in vitro culture systems and animal models have limited ability to emulate human physiology. Despite major advances, engineered tissues do not recapitulate the adult heart, largely due to the immature phenotype of human cardiomyocytes derived from the induced pluripotent stem cells (hiPS-CM). Engineered tissues lack many of the hallmarks of adult heart muscle: excitation-contraction (EC) coupling (requiring networks of T-tubules), mature calcium homeostasis (requiring functional sarcoplasmic reticulum), and—most importantly—the positive force-frequency response. The limited ability of these tissues to mimic the adult human heart physiology remains a critical barrier to the discovery and implementation of new therapeutic options. Removal of this critical barrier would have wide applicability in disease modeling and preclinical drug screening, for example.

The estimated costs for bringing a new drug to the clinic has increased to ~$1.2 billion, up from about ~$800 million in 2003. Pharmaceutical companies face their largest losses when drugs fail late, in Phase III trials and at post-marketing. The majority of drug recalls in the past 40 years have been due to cardiotoxicity (19% of withdrawals), hepatotoxicity (26% of withdrawals), or unpredicted adverse effects of drug interactions. Drug toxicities may result in deaths and are highly costly.

As many as 60% of late-stage drug development failures are due to unforeseen absorption, distribution, metabolism, excretion, and toxicity profiles that might have been predicted if models of human liver tissue were available earlier in drug development. Likewise, heart models of cardiotoxicity do not always correlate with clinical risks. For example, preclinical hERG assays are quite helpful in identifying compounds with action potential prolongation, but are not sufficient for predicting clinical QT-proarrhythmia. Thus, preclinical models can provide a critical window into human physiology for determining drug safety and efficacy.

The current lack of predictive drug screening is a barrier to bringing drugs to patients, and escalates the number and costs with drug failures. Existing drug screening models lack structural and signaling features of native tissues, the temporal and spatial sequences of molecular and physical regulatory factors, and the dynamic forces and systematic factors provided by blood circulation. Animal models often fail to capture human-specific features, and offer only limited control of and insight into specific mechanisms. As a result, the disconnection between in vitro studies, translational animal models, and human clinical studies, decreases the effectiveness of resulting therapeutic strategies. Consequently, most drugs tested in animals fail in clinical trials. Engineered cardiac tissues of sufficient biological fidelity would foster disease modeling and the development of patient-specific drug regimens. Cardiac tissues formed from human induced pluripotent stem (hiPS) cells have limited utility due to their immature, fetal-like phenotype.

SUMMARY

The disclosed subject matter provides functional human tissue units, engineered to combine biological fidelity with the use of high-throughput platforms and real-time measurement of physiological responses.

In accordance with one aspect, iPS cell-based vascular, cardiac and tumor micro-tissues are formed. The iPS based micro-tissues are functional three dimensional tissue units having tissue-specific architectures ("ultrastructures") having an integrated vascular network, microfluidic endothelialized connections between tissue modules, which establish a functional representation of human biology in health, injury and disease.

In one embodiment, the engineered tissue includes many of the molecular, structural, and functional properties of adult human heart muscle, including well-developed registers of sarcomeres, networks of T-tubules, mature calcium homeostasis, comprehensive responses to beta-adrenergic stimulation, and a positive force-frequency relationship. The advanced level of maturation was confirmed by comparison to human fetal heart tissue, and probed by studying physiological responses to drugs and by modeling heart disease.

It was found that the measured drug EC50 values corresponded to plasma levels in patients, while the patient-specific model of Timothy Syndrome recapitulated the disease phenotype and the effects of clinically used drugs. Adult-like human heart muscle can be engineered in vitro and used for predictive studies of drugs and modeling of cardiac disease. Intensity training enables formation of adult-like heart muscle from patient-specific hiPS cells, for use in predictive studies of drugs and disease. In other embodiments, the engineered tissue is liver or vascular tissue.

In another aspect, a method is provided for engineering the 3-D micro-tissue. In one embodiment, the method includes deriving cardiomyocytes from induced stem cells ("iPS") and encapsulating the derived cardiomyocytes in a hydrogel. The hydrogel encapsulated cardiomyocytes undergo electromechanical conditioning to achieve cell maturation. The electromechanical conditioning involves exposing the derived cardiomyocytes to electromechanical stimuli that increases in intensity over a period of time. The resultant three-dimensional cardiac tissue includes transverse (T)-tubules, high density of mitochondria and a positive force-frequency relationship, all of which are hallmark features of adult human heart tissue that have not been demonstrated previously.

An integral component of the tissue platform is a set of on-line methods for measuring functional responses of the heart tissue. Tissue contractility was measured by tracking the change in the projected tissue area as a function of time, from bright field videos acquired at rates of 150 frames per second. An automated intensity threshold was used to identify cell location in the video frame. Absolute differences in cell area from the baseline frame were then calculated to create a time course of cell area dynamics as a function of time. The resulting time courses were analyzed using an automated peak finding algorithm to determine locations of maximum cell contraction indicated by the locations of local maxima in the time courses. Beat period lengths were determined from the length of time between pairs of local maxima. Beat frequencies were determined by inverting beat periods. Contraction amplitude relaxation times were measured from the length of time required for the time course to relax in amplitude from the peak contraction amplitude of the local maxima to the calculated relaxation amplitude (e.g. the R90 time was the length of time elapsed from the local maxima until the contraction time course reached 10% of the local maximum contraction difference amplitude).

Calcium transients were analyzed using the Fluo-4 NW dye in RPMI+B27 media containing 5 μM blebbistatin to reduce movement artifacts, for 30 minutes at 37° C. Videos were acquired at a rate of 150 frames per second using a Pike F-032 camera controlled by the custom-designed, free-source SPLASSH software. Videos were analyzed in MAT-LAB using a custom script that calculated the temporal changes in calcium fluorescence intensity. Each frame was normalized to a baseline background region to give baseline corrected changes in minimum and maximum fluorescence values for each frame. This temporal change in fluorescence intensity was presented as a calcium transient trace. The calcium transient timing was determined as the peak-to-peak value of two successive beats as defined by the peak maxima. Calcium transient amplitude was determined by numerically integrating the area below the peak maxima relative to the baseline. Calcium transient traces were analyzed during 5 mM caffeine stimulation of tissue constructs previously treated with either 1 mM verapamil or 0.002 mM thapsigargin. Quantitative measurements of the caffeine response were obtained by comparing the calcium transient amplitude before and after the addition of 5 mM caffeine. The average rhythmicity was defined as the ratio of the parameter standard deviation to the parameter mean of the corresponding (control, constant, intensity) tissue group. Beats with parameter measurements falling outside two standard deviations from the average rhythmicity were classified as irregular.

The platform allows force measurements from the deflection of the elastic pillars the properties of which are precisely set. Twitch tension measurements can be obtained by increasing the [Ca2+] concentration from 0.2 to 2.8 mmol/L. The tissues were subjected to electrical stimulation for 3 minutes, and an average of 10 contractions were measured. The stimulation was then discontinued for 10, 20, or 30 seconds, and the tissues were allowed to recover for 2 minutes. Post-rest potentiation measurements were obtained by analyzing the change in twitch tension from the first beat upon re-initiation of electrical stimulus.

Contractility and twitch parameters can be further characterized in response to changes in tissue construct length (Frank-Starling response) and to the increasing electrical stimulation. Twitch forces were calculated as the average of the difference between maximum and minimum cyclic force. Force-length relationships to determine the Frank-Starling relationship were determined by incrementally increasing the distance between pillars in the organ bath, and then allowing the tissue to recover before the force measurement was made. The Frank-Starling responses were recorded by increasing the length of the tissue in step-wise increments until increases in length no longer elicited increases in force generation. The force-frequency relationship (FFR) can be measured by increasing the electrical stimulation frequency from 1 Hz to 6 Hz, in 1 Hz intervals and statistically analyzed to evaluate the changes in response normalized to the 1 Hz baseline frequency. The tissues were exposed to each stimulation frequency for 30 seconds and allowed to rest for 60 seconds before increasing the stimulation frequency to the next level.

Finally, a software pipeline was developed to characterize and predict the behavior of cardiac tissue under a variety of conditions. Raw data are analyzed using video processing software to build a feature space comprised of relevant parameters, such as beat frequency, force of contraction, and relaxation time, among others. The resulting vectors and other relevant information, such as drug concentrations and labels are then given to machine learning algorithms to build classifiers and regressors. Immediately obvious applications include the determination of tissue state using video data alone, and the prediction of in vivo drug responses, but these methods are widely relevant to a host of other applications such as characterizing the correlation between our tissues and the corresponding molecular, cellular, and clinical phenotypes. This software package is an integral part of the overall design because it allows us to draw conclusions from large quantities of data in an automated, unbiased, high-throughput way.

DRAWINGS

The patent or application file contains at least one drawing executed in color. Copies of this patent or patent application publication with color drawing(s) will be provided by the Office upon request and payment of the necessary fee.

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 13A, 13B, 13C, 13 D, 13e and 13F show predictive $EC_{50}$ values found for various drugs: Isoproterenol, Propulsid, caffeine, mitoxantrone, epinephrine and naphthalene.

Figure 14:
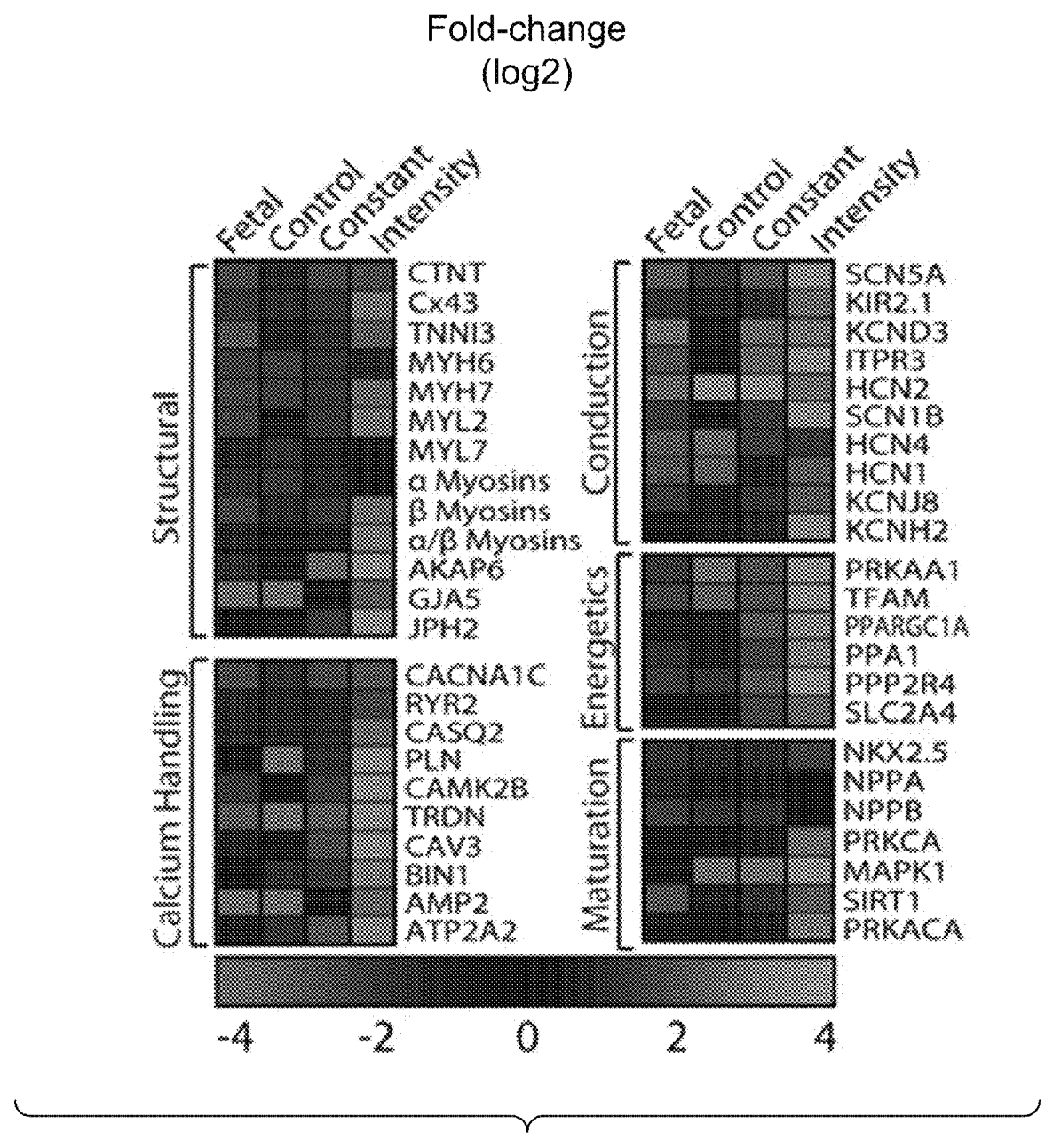
Figure 16C:
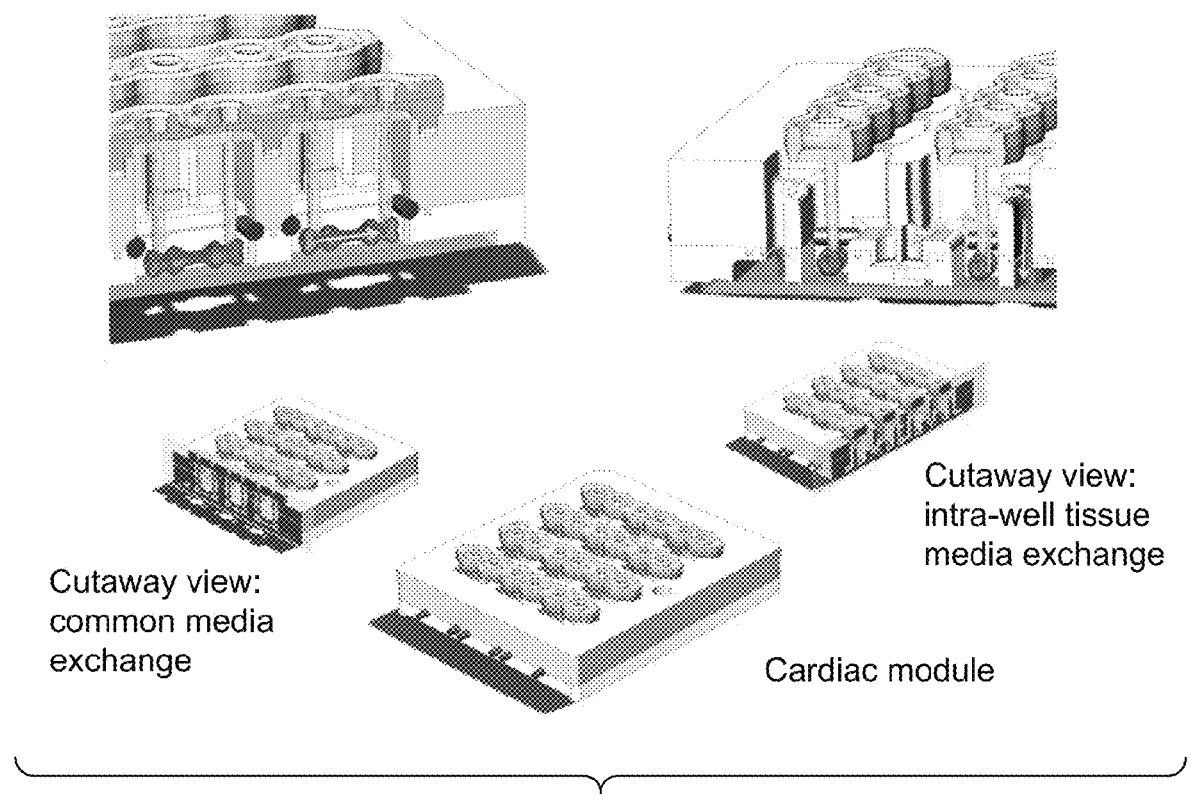
Figure 16D:
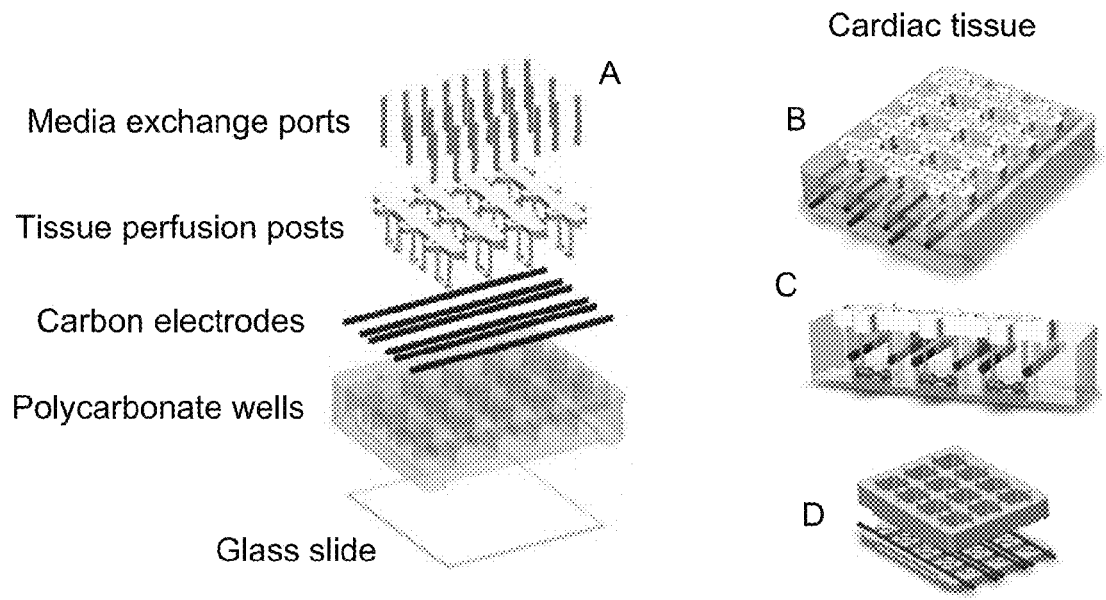
Figure 16G:
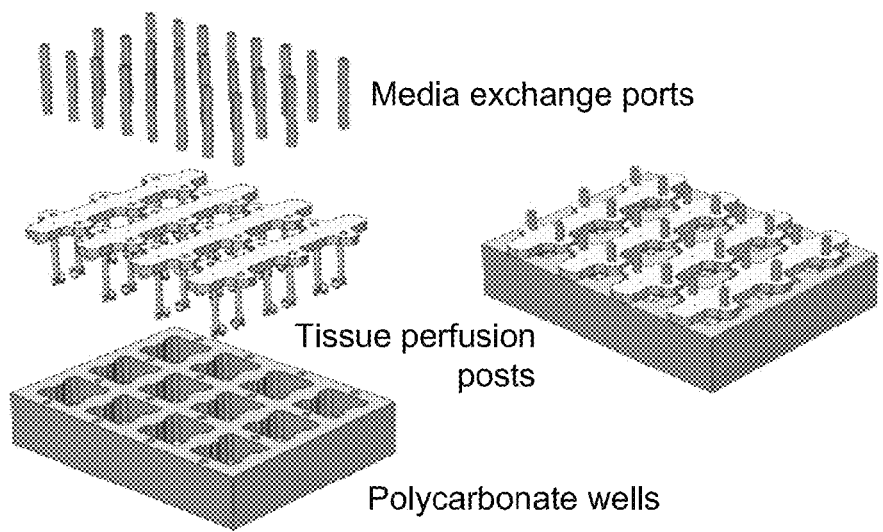
Figure 16H:
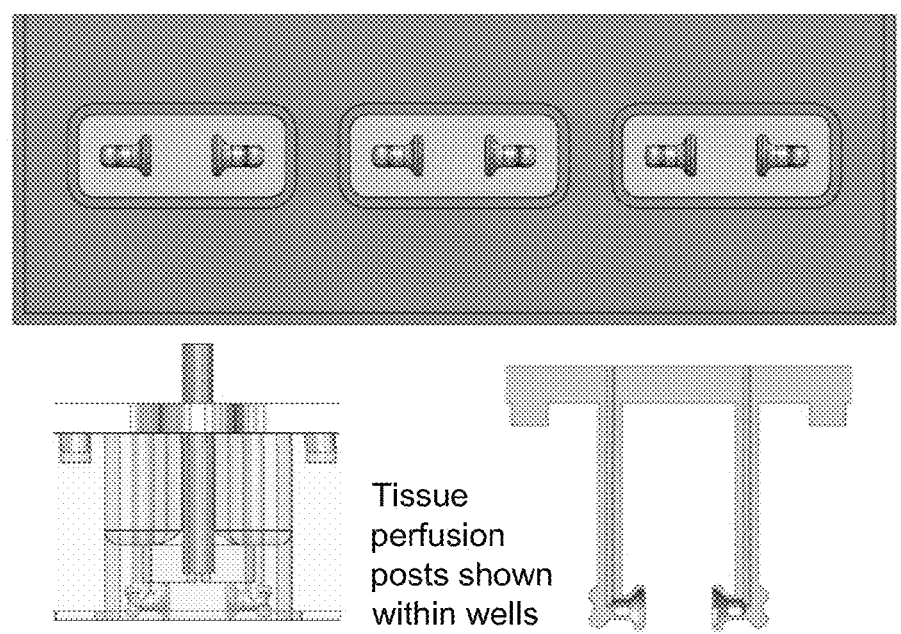
Figure 17A:
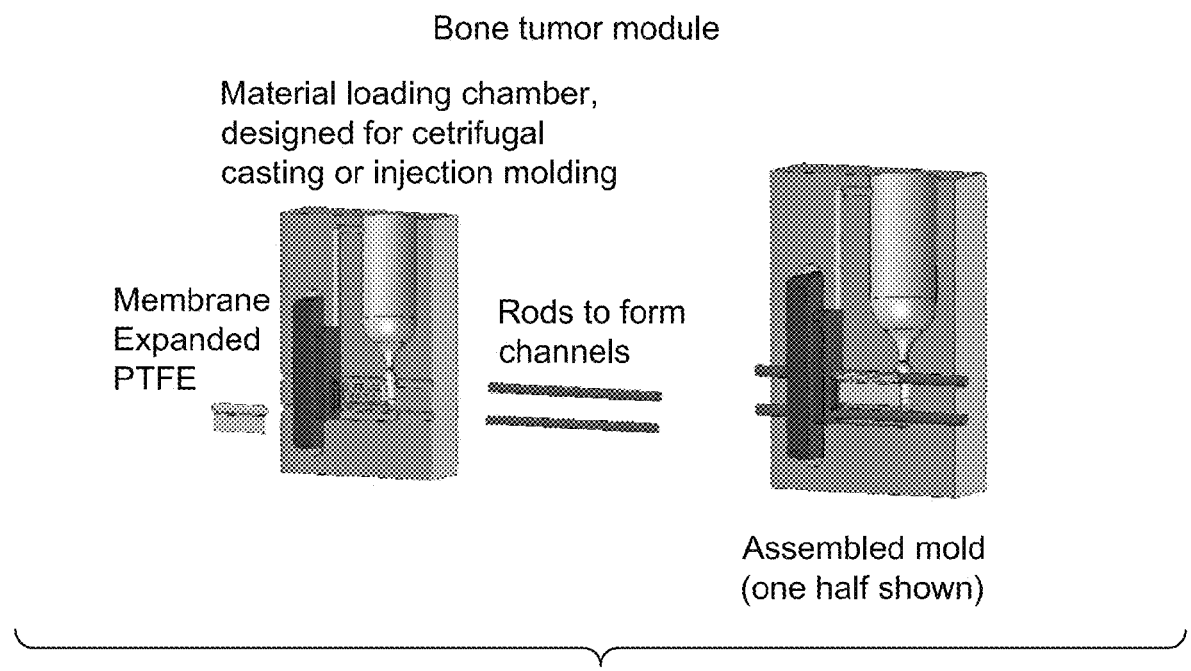
Figure 17B:
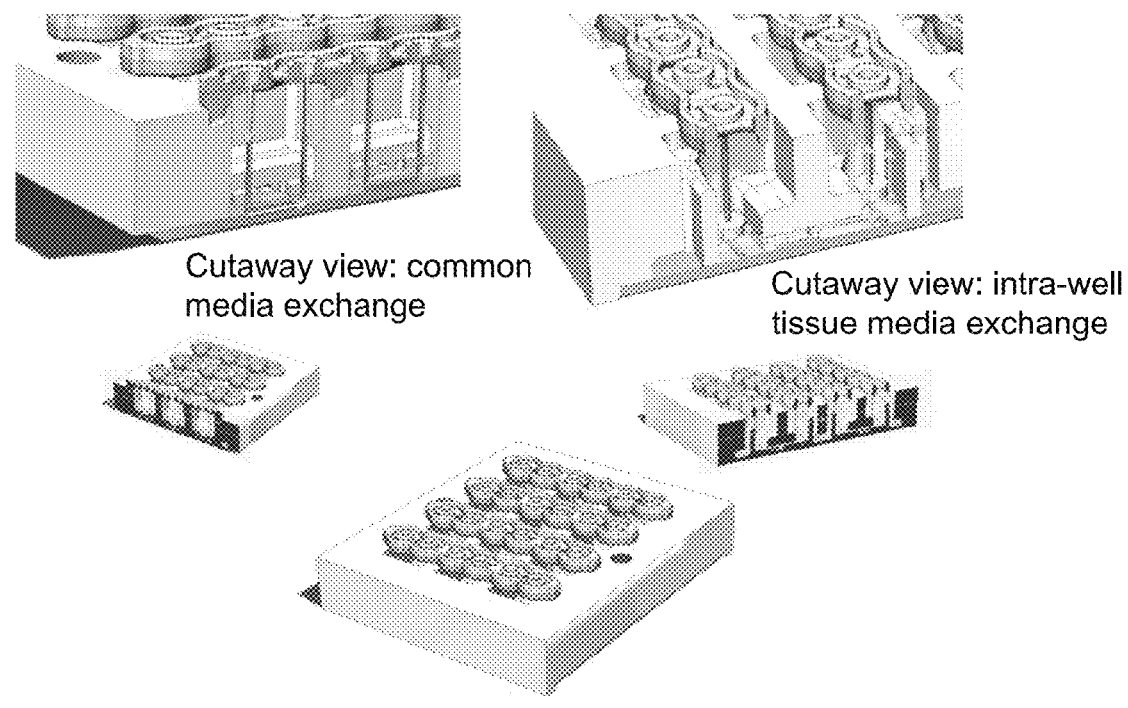
Figure 17C:
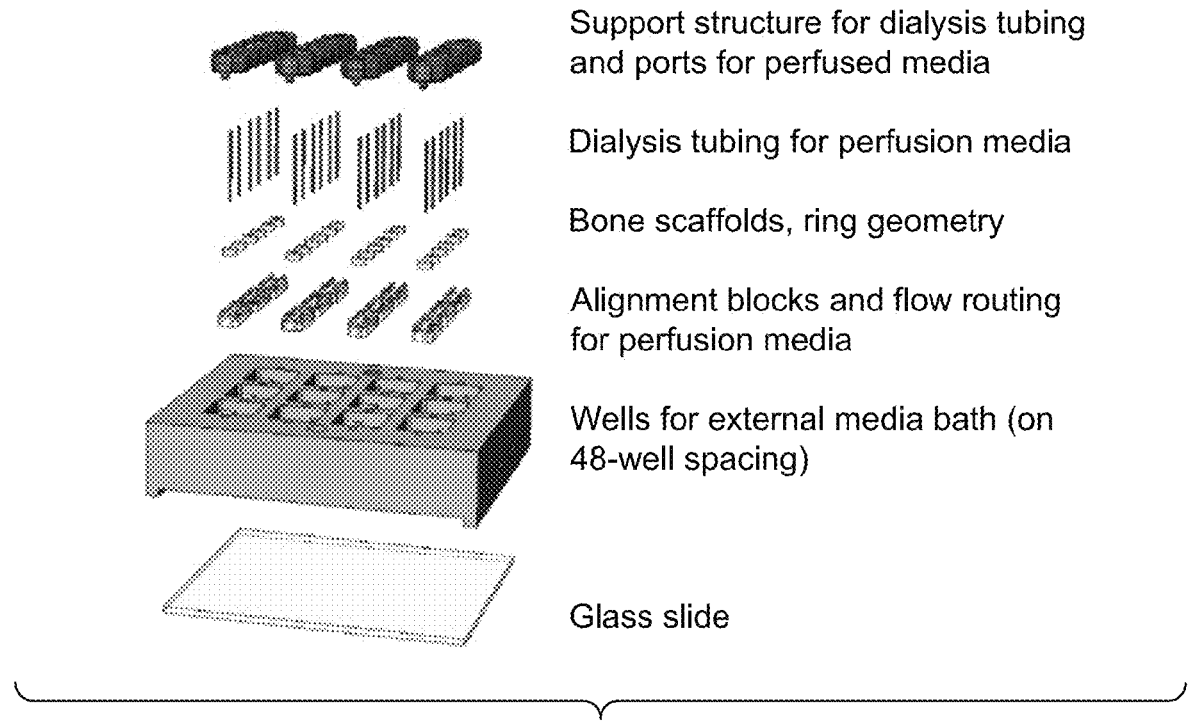
Figure 17D:
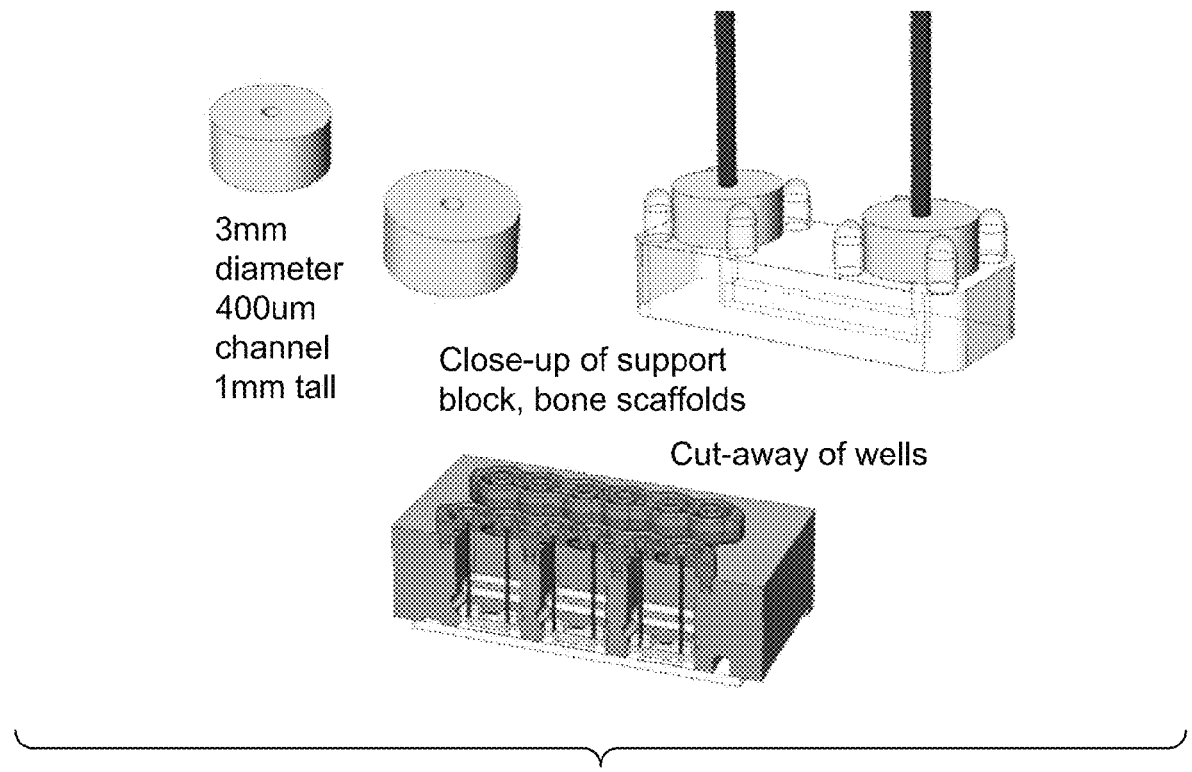
Figure 17E:
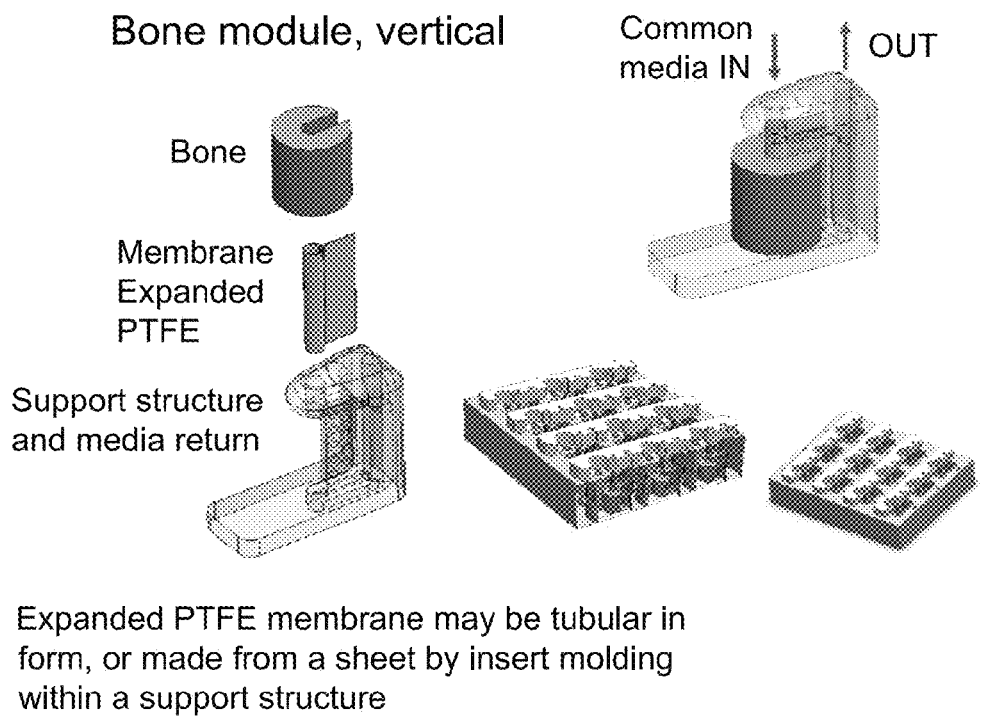
Figure 17F:
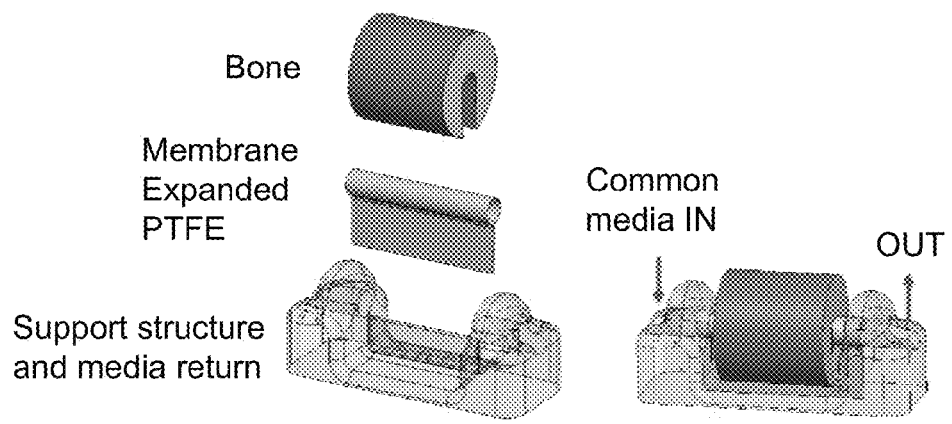
Figure 18A:
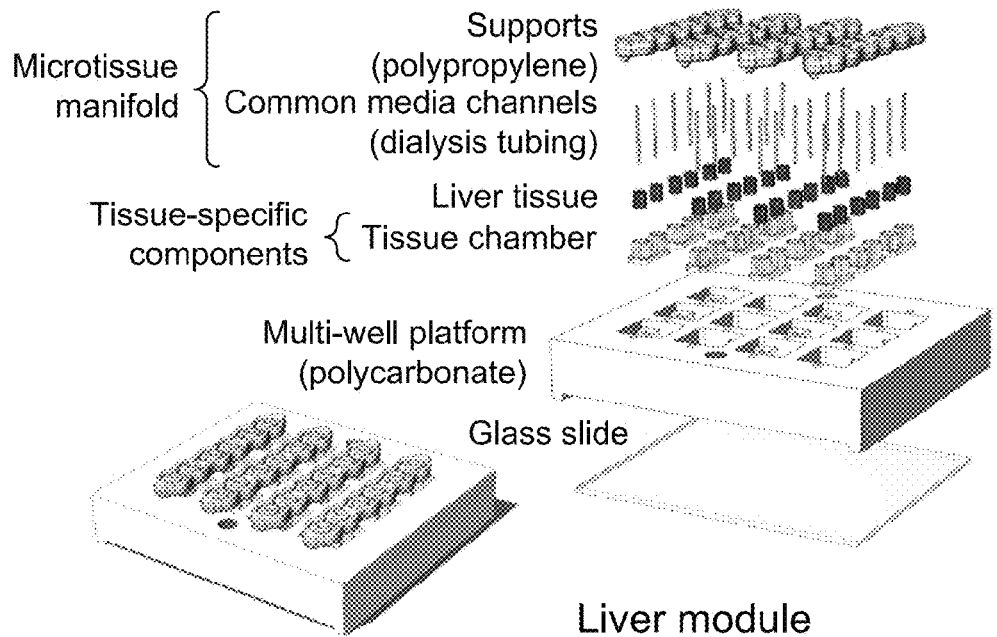
Figure 18B:
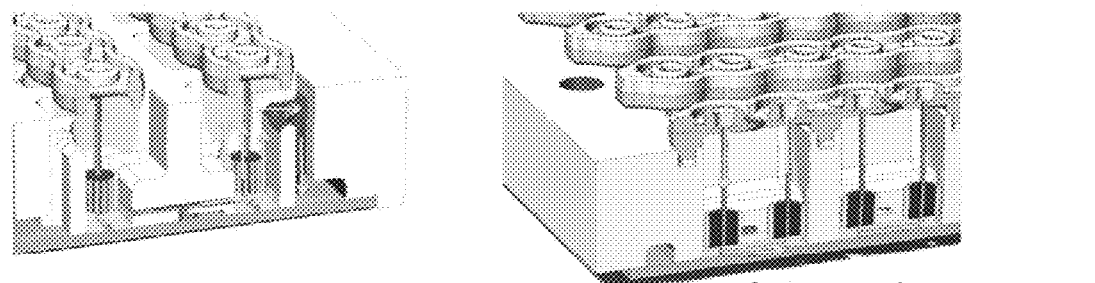
Figure 18C:
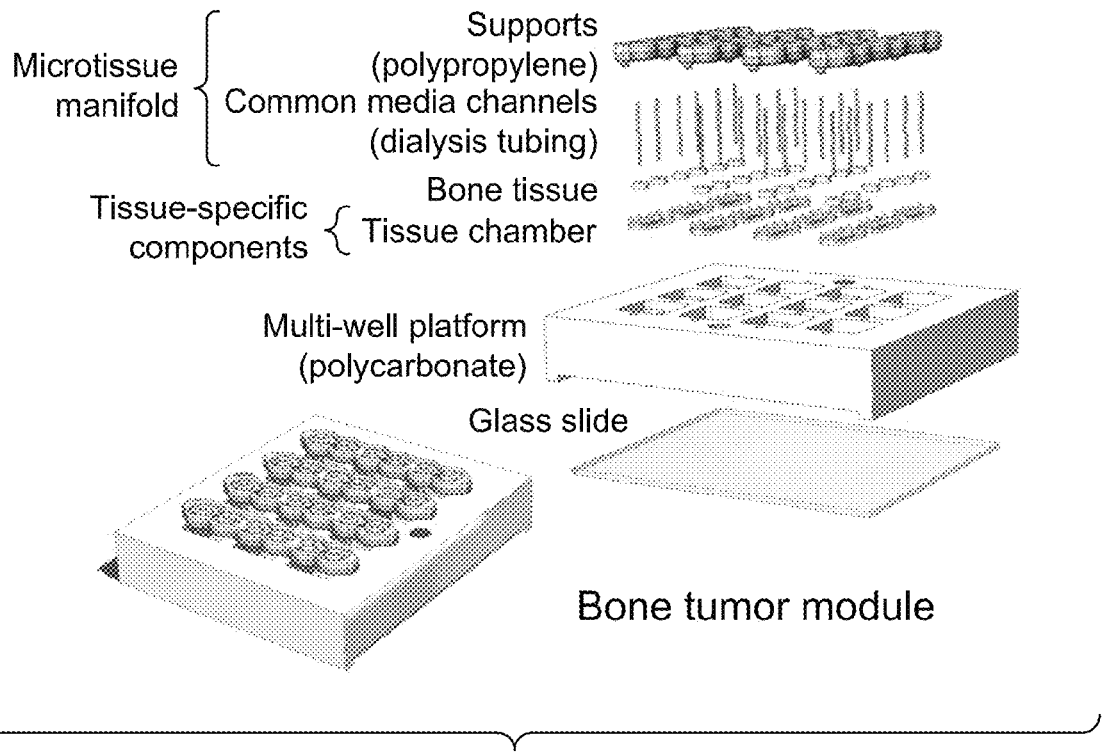
Figure 18D:
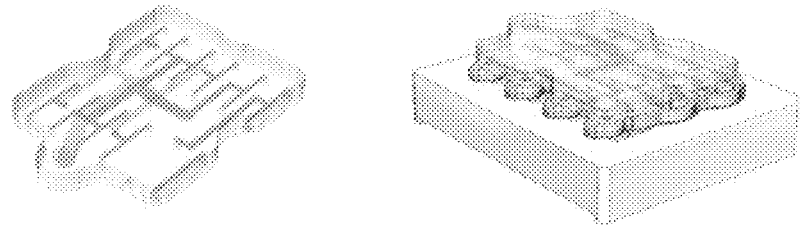
Figure 18E:
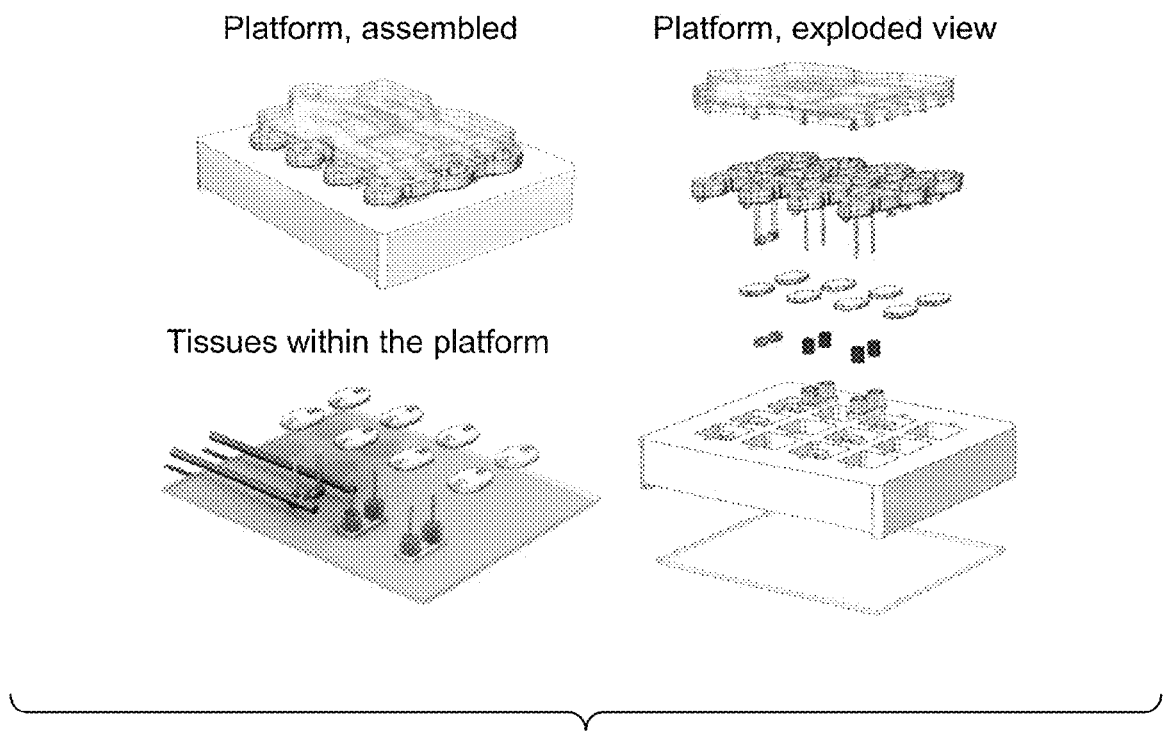
Figure 18F:
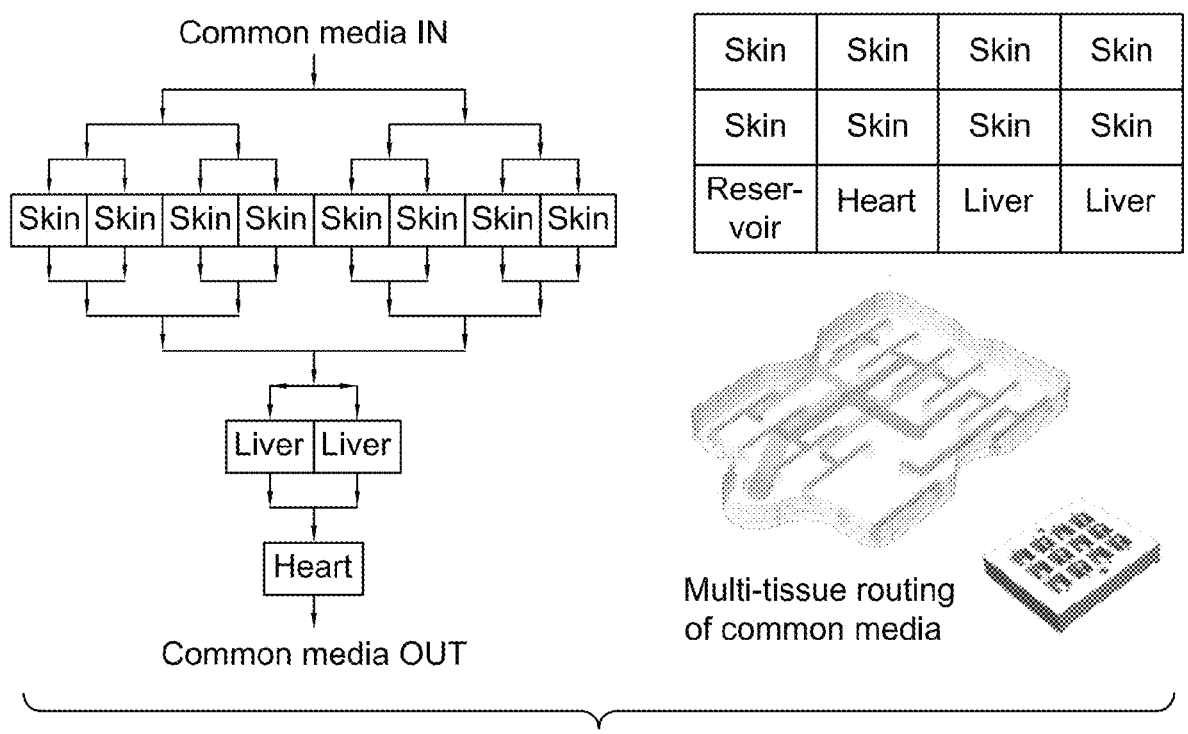
Figure 18G:
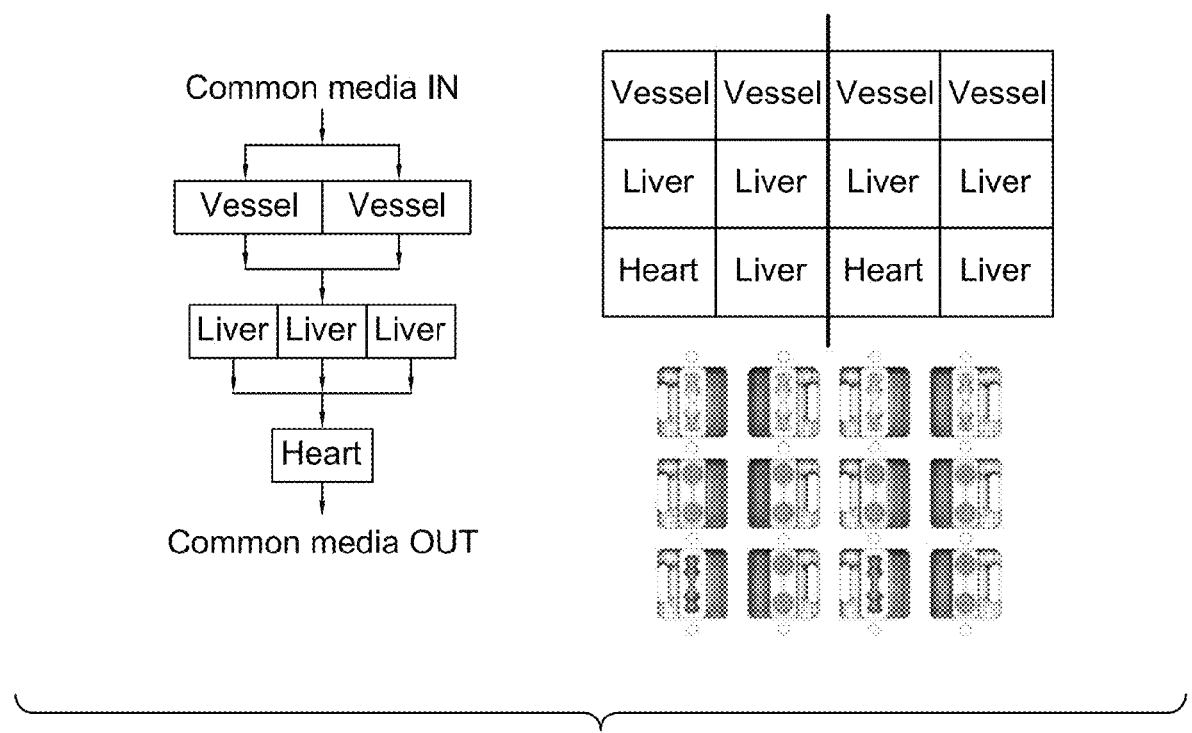

FIG. 14 shows Fold-change in the expression of genes encoding for structural properties, calcium handling, conduction, energetics and maturation of engineered cardiac tissues.

FIGS. 15A to 15D is an exploded view of a bioreactor used to make the 3D functional micro-tissue is shown.

FIG. 16A to 16J shows the components integrated into a bioreactor.

FIG. 17A to 17F shows bone tumor module and process steps, and bioreactor and alternate configurations of bioreactor components.

FIGS. 18A to 18G depicts a various multi-tissue platforms and process steps.

Figure 19A:
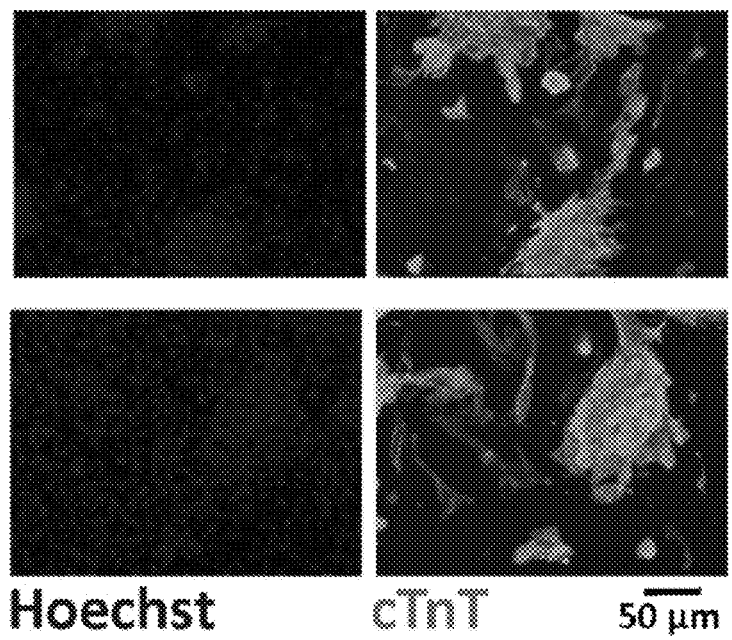
Figure 19B:
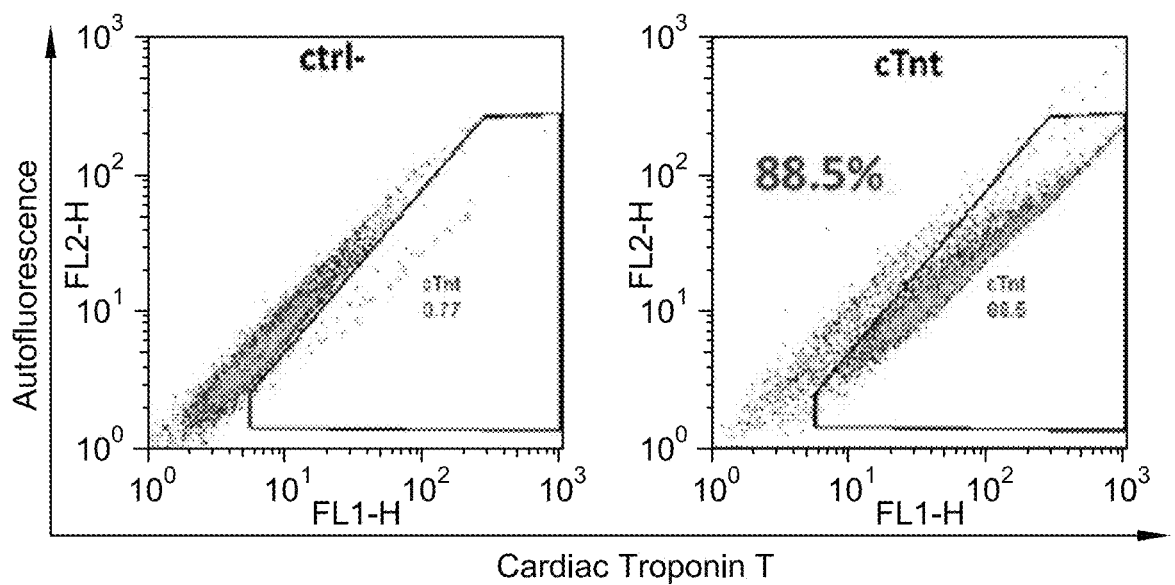

FIGS. 19A and 19B show organoids formed using hiPS-CMs derived from three healthy human donors.

FIGS. 20A to 20I show how intensity training drives BEAM maturation.

Figure 21F:
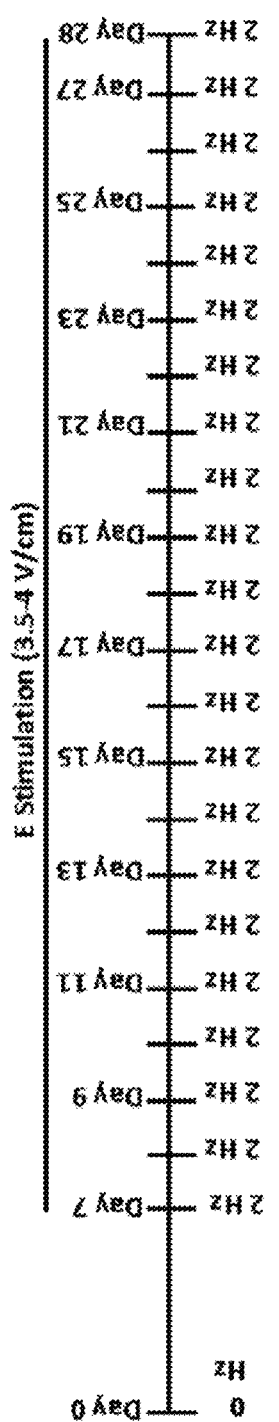

FIGS. 21A to 21 G show BEAM bioreactor and design.

FIGS. 22A to 22J show how intensity training enhances gene expression and ultrastructural properties within BEAMs.

FIGS. 23A to 23H show how various intensity training enables predictive cardiotoxicity screening.

FIGS. 24A to 24H show physiologically relevant Timothy Syndrome Disease Model.

FIGS. 25A to 25H show enhanced maturation and functionality of BEAMs in response to training regimen as function of time.

FIGS. 26A to 26E show BEAM functionality and detraining over time.

Figure 27A:
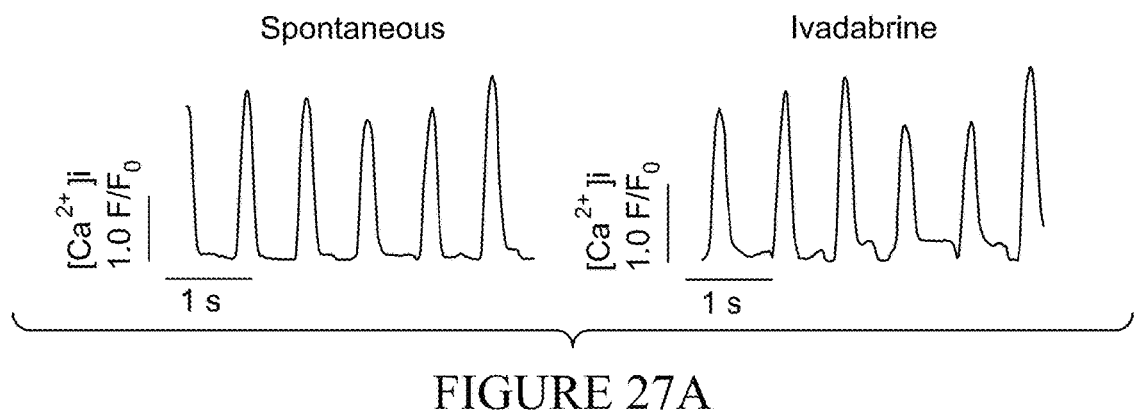
Figure 27B:
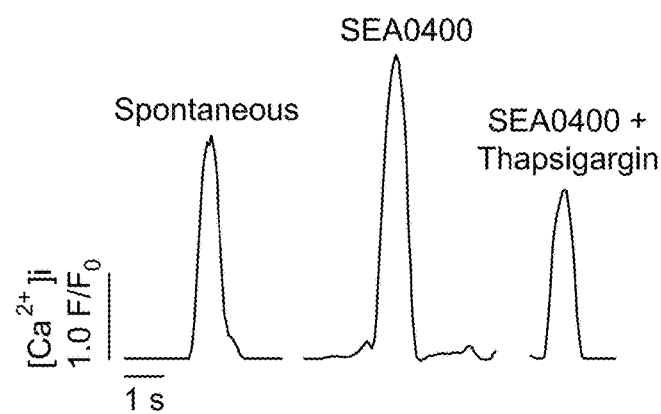
Figure 27C:
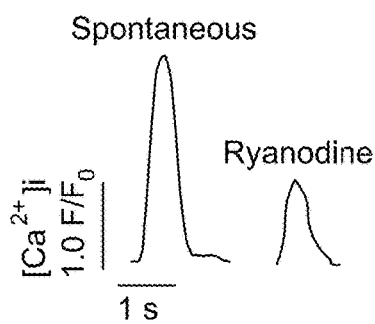
Figure 28A:
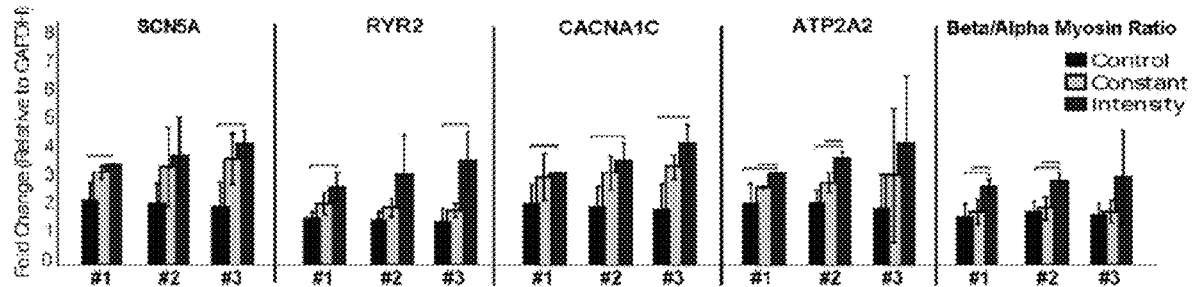
Figure 28B:
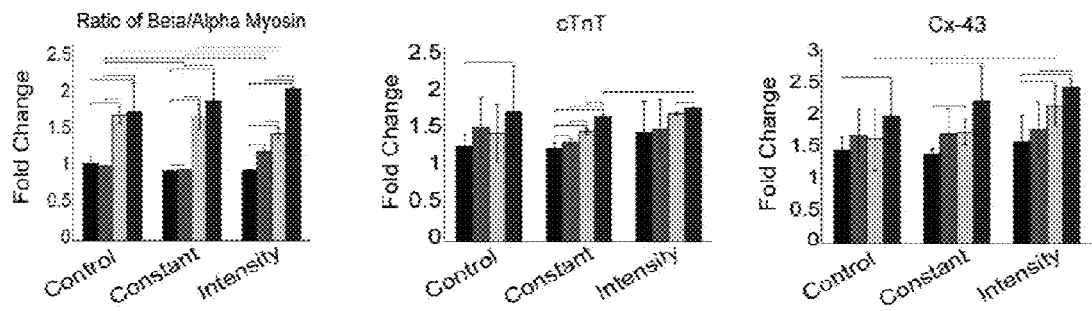
Figure 28C:
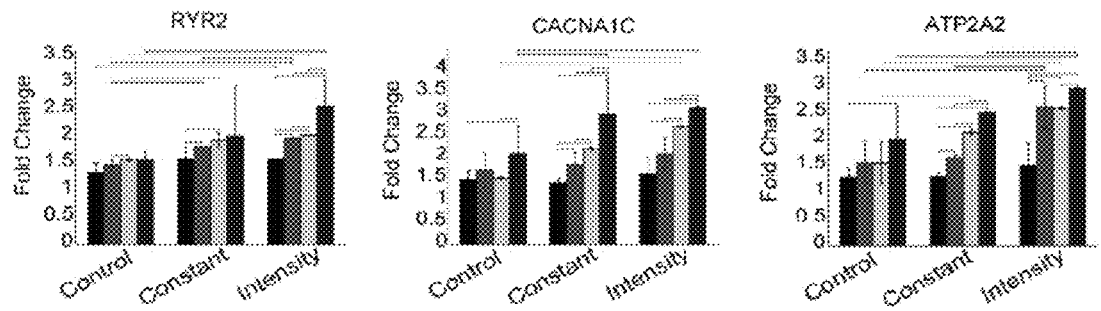
Figure 28D:
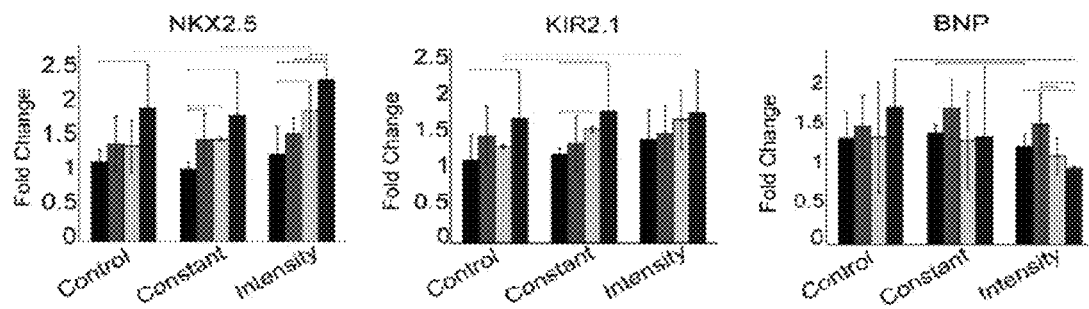

FIGS. 27A to 27C show upregulation of calcium handling proteins via intensity training enhance functionality.

FIGS. 28A to 28D show gene expression of BEAMs over time.

FIGS. 29A to 29D show physiological hypertrophy within BEAMs.

FIGS. 30A to 30I show increased calcium handling via intensity training over time.

Figure 31A:
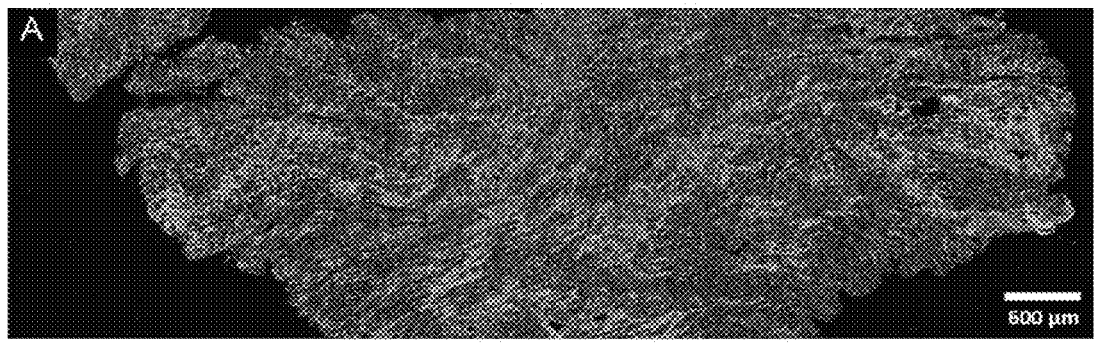
Figure 31B:
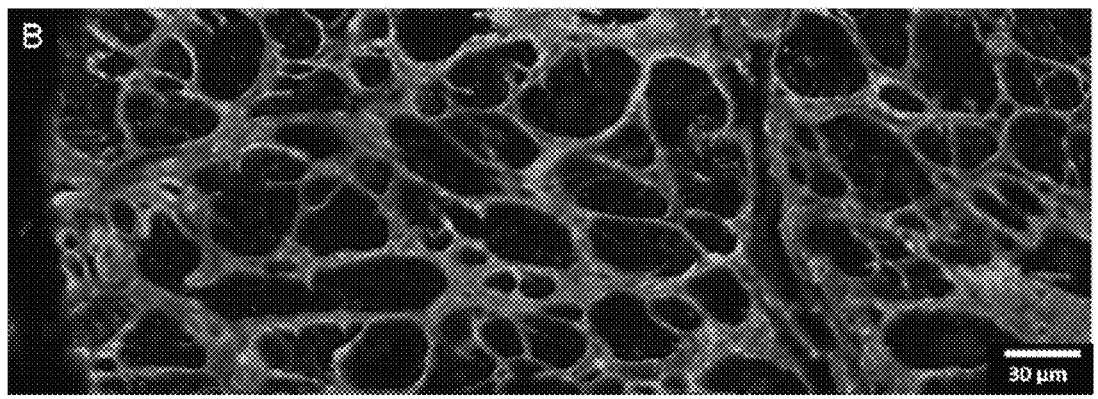
Figure 31C:
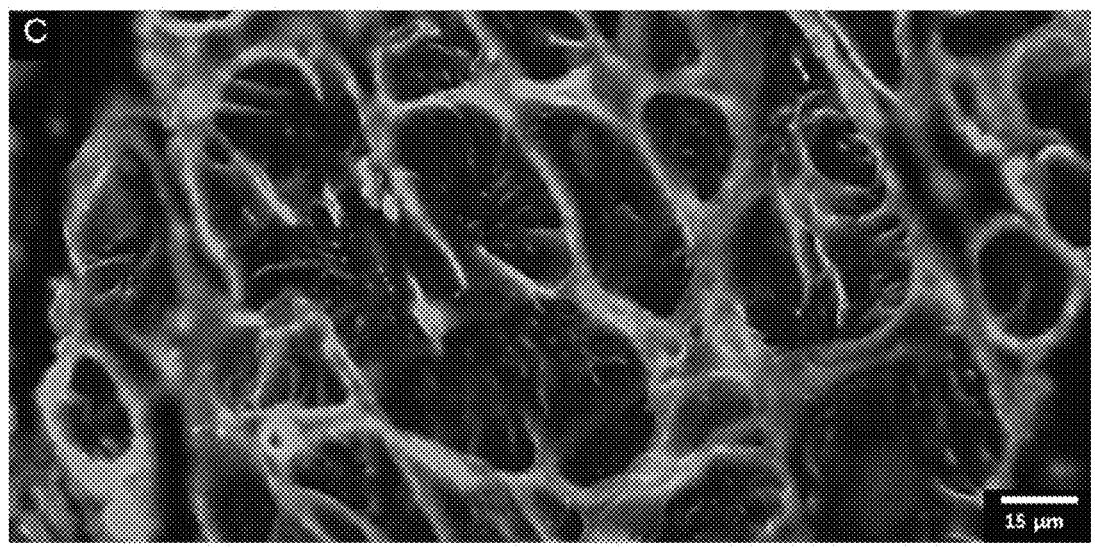

FIG. 31A to 31C show axial t-tubule immunostains.

FIG. 32A to 32E show molecular structure within intensity trained BEAMs.

Figure 33:
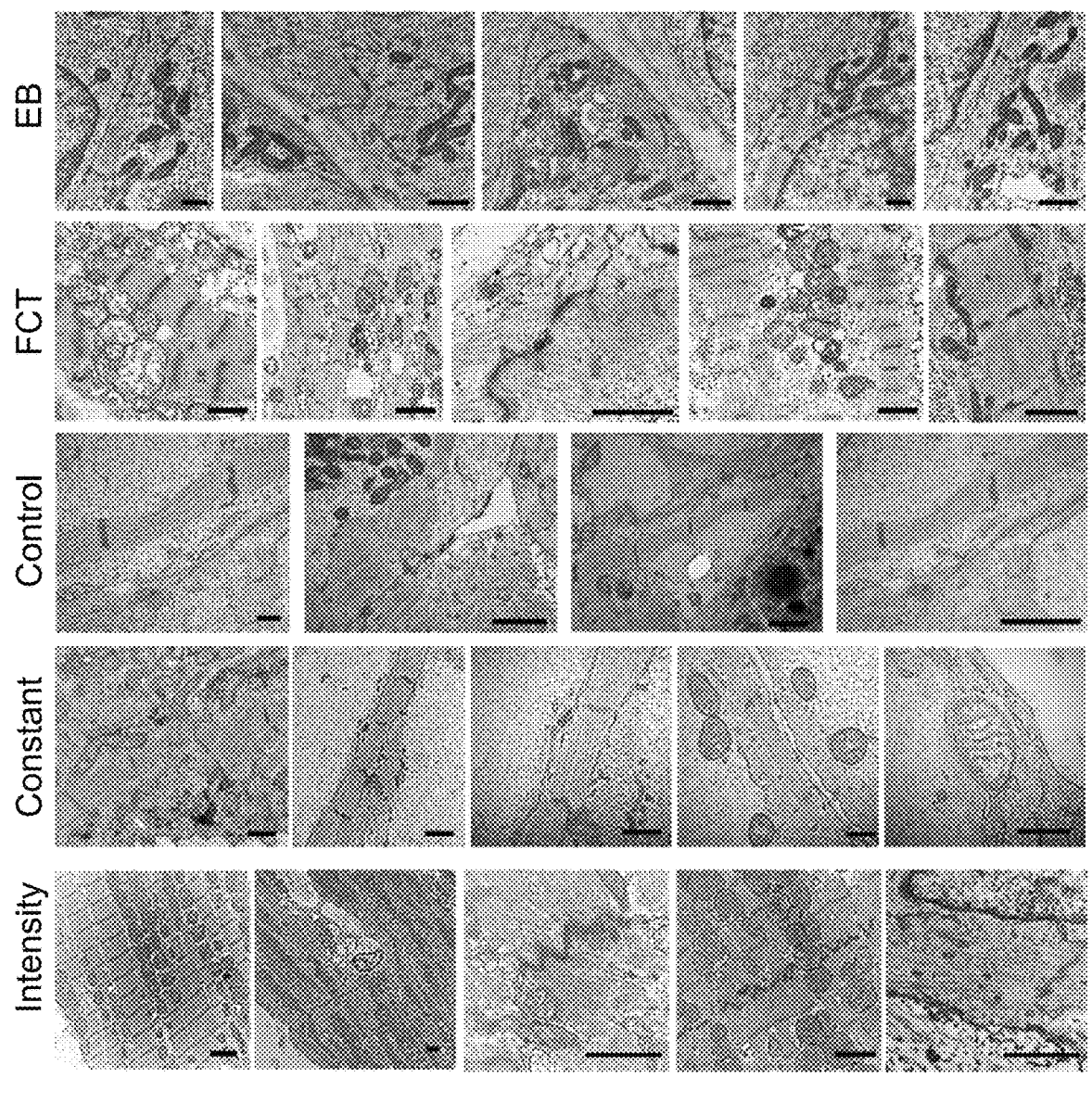

FIG. 33 shows enhanced ultrastructural properties in BEAMs due to intensity training.

Figure 34:
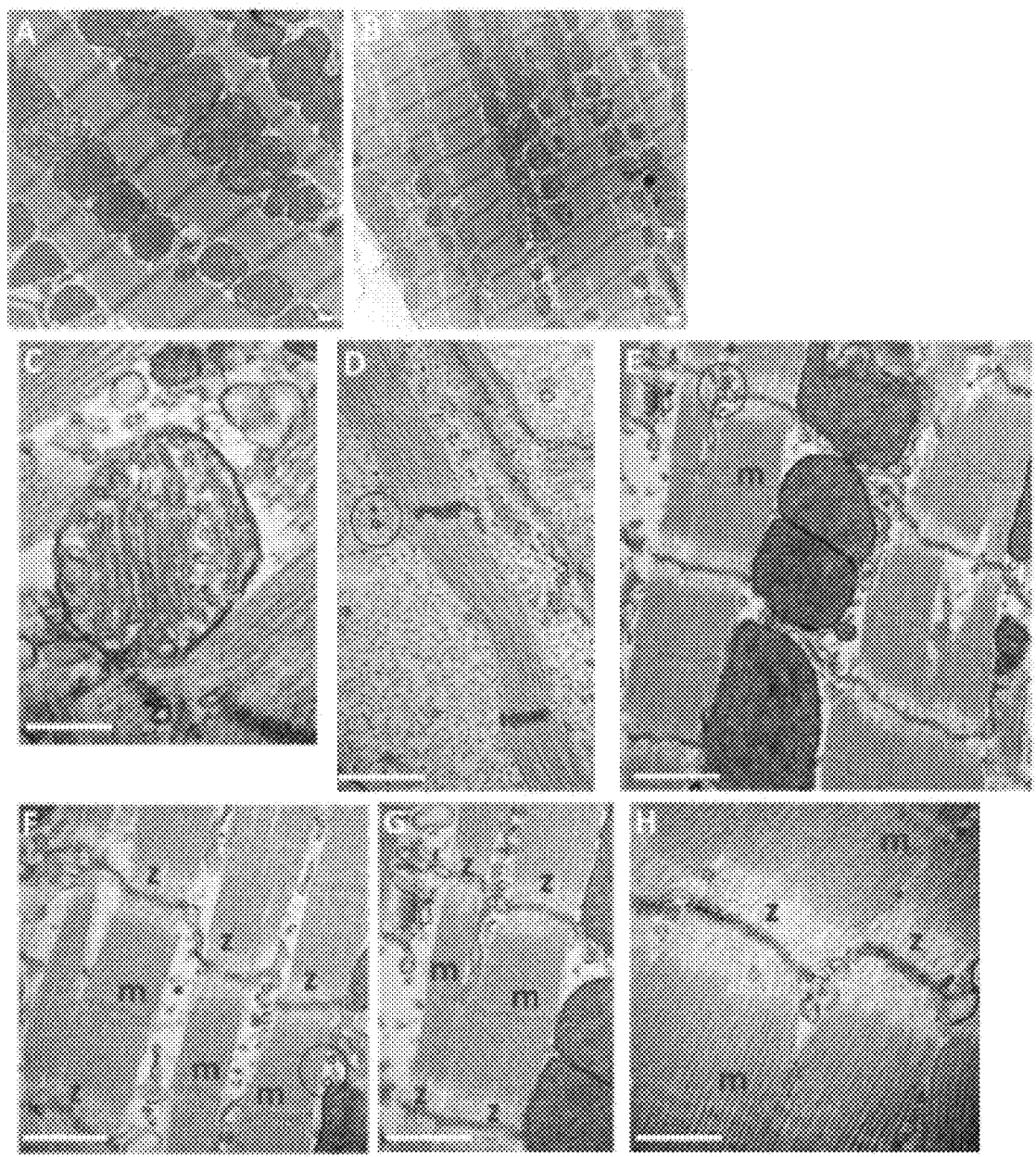

FIG. 34 shows TEM images A-H of intensity-trained BEAMs.

FIG. 35A to 35ll show abnormal calcium handling within Timothy Syndrome BEAM model.

Figure 36A:
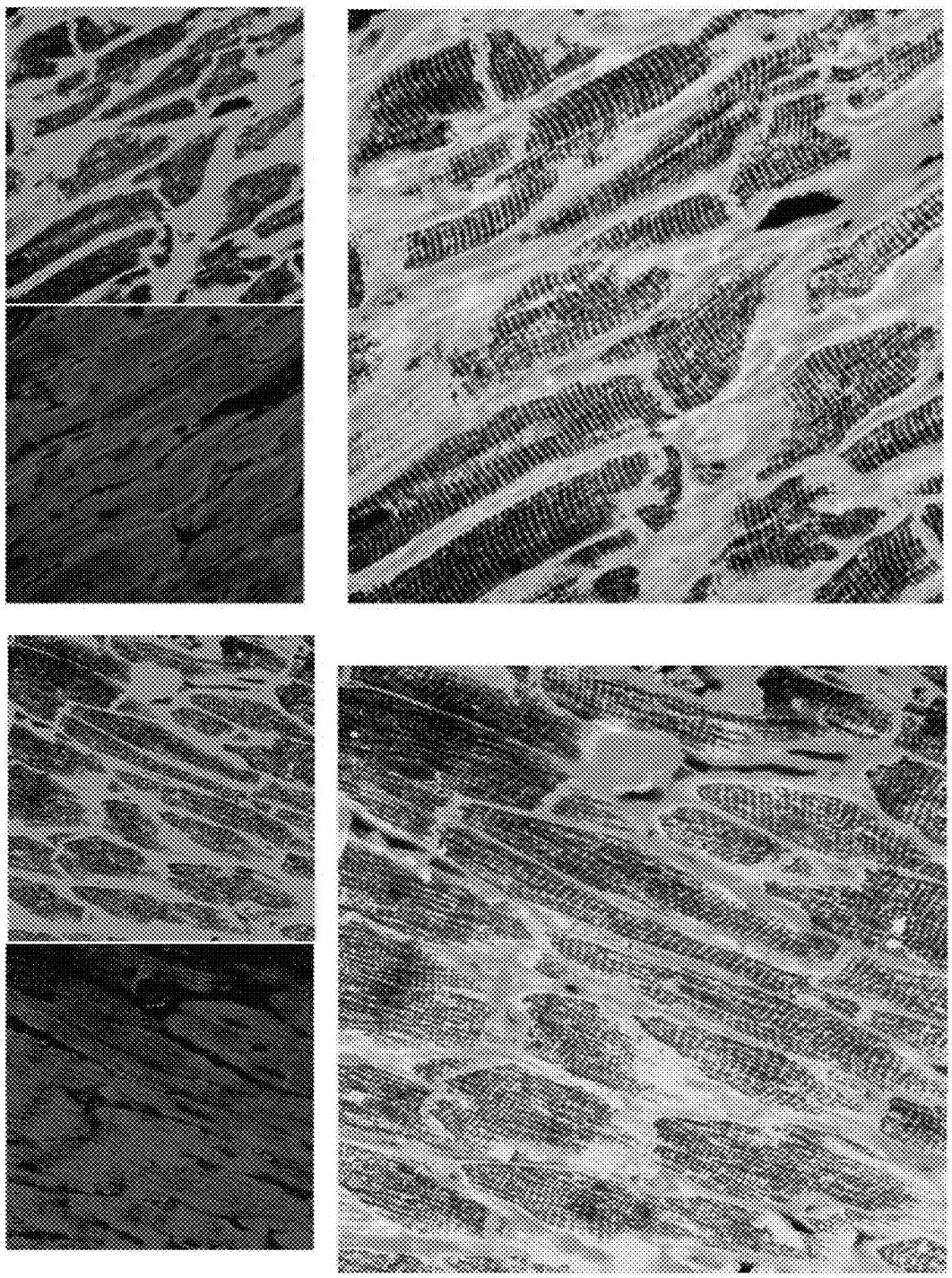
Figure 36B:
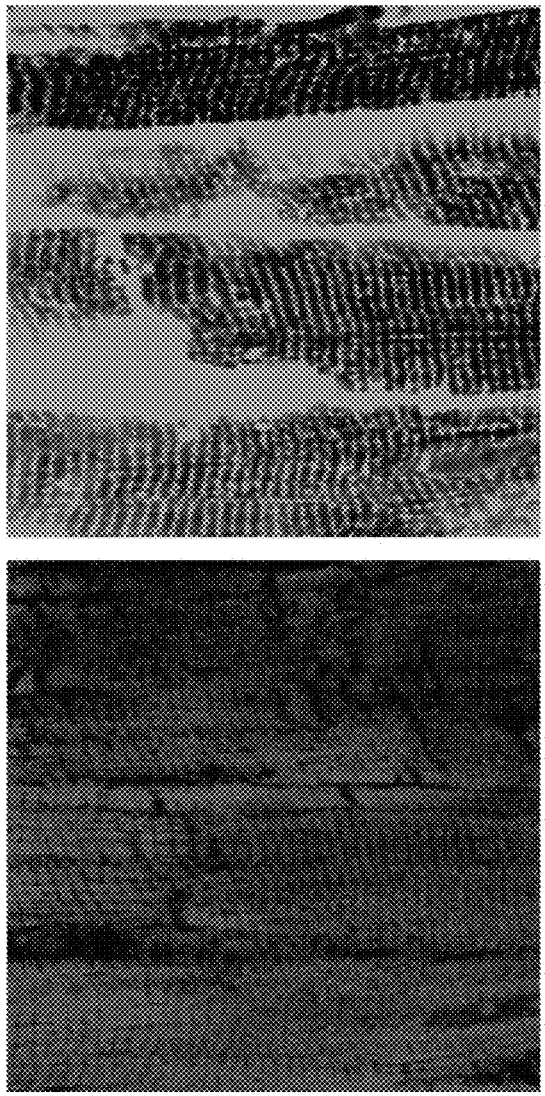

FIGS. 36A and 36B show magnified longitudinal section of intensity trained BEAMs.

FIGS. 37A to 37F show schematic images of a PDMF bioreactor and pillars.

Figure 38A:
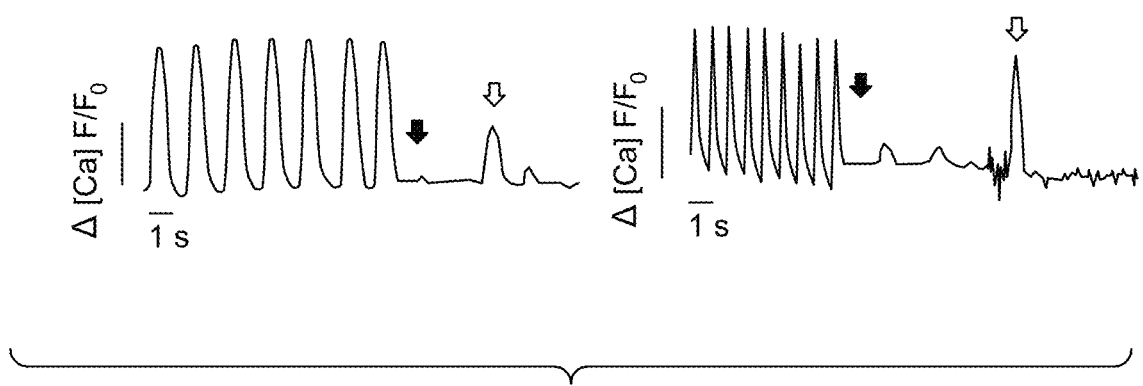
Figure 38B:
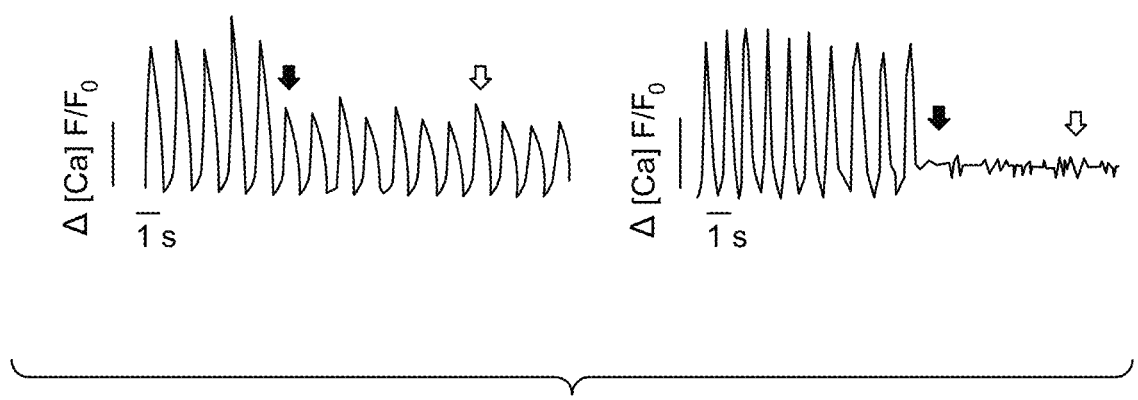

FIGS. 38A and 38B illustrate calcium handling results.

Figure 39:
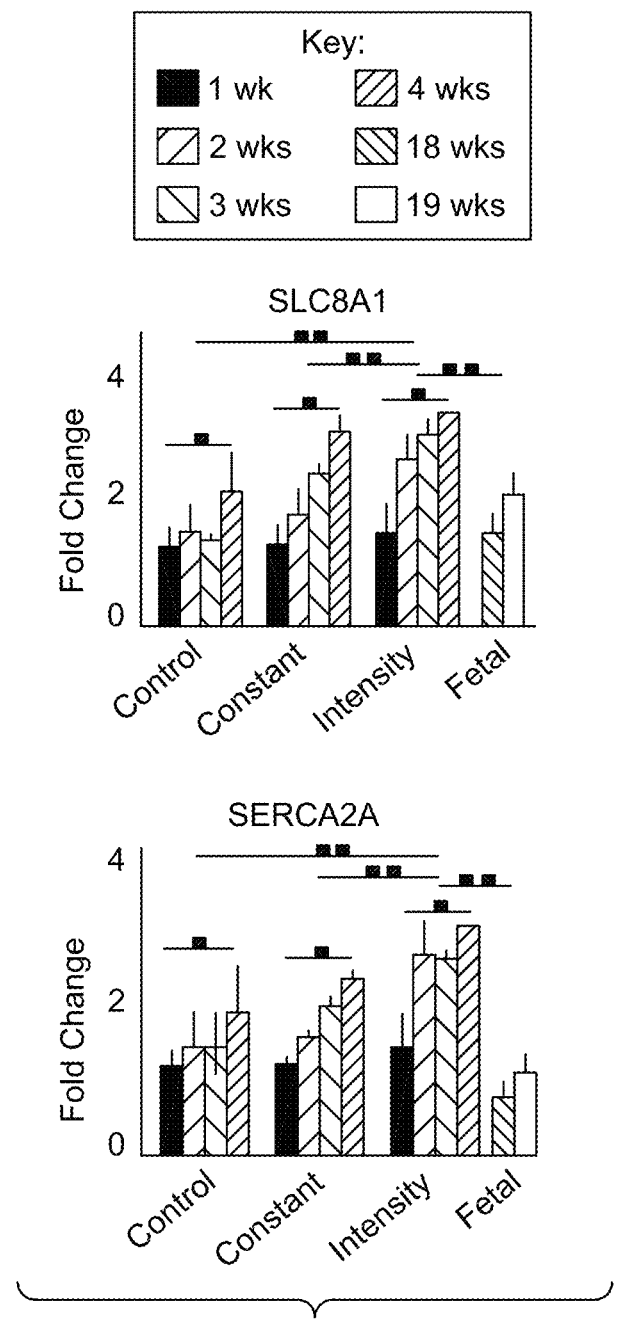

FIG. 39 shows effects of intensity training on SLC8A1 (encoding for the Na—Ca Exchange Pump NCX), and ATP2A2 (encoding for SERCA).

Figure 40A:
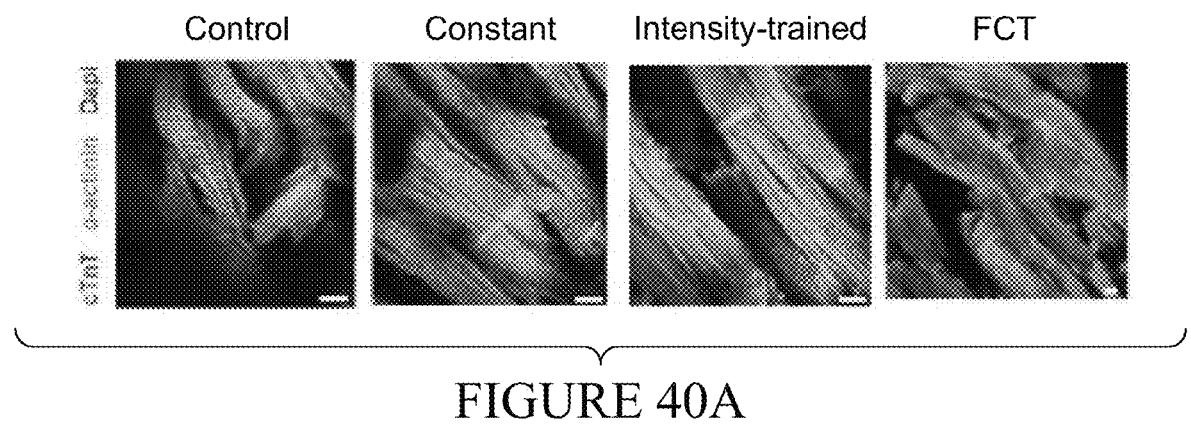
Figure 40B:
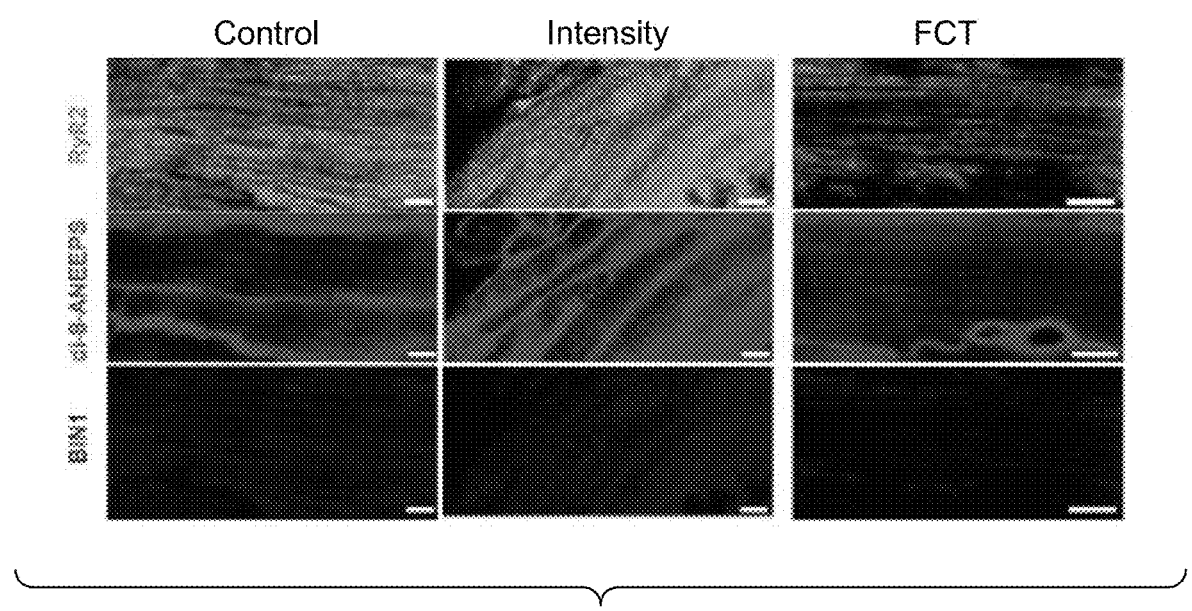

FIGS. 40A and 40B show organoids with mature ultrastructural features.

Figure 41:
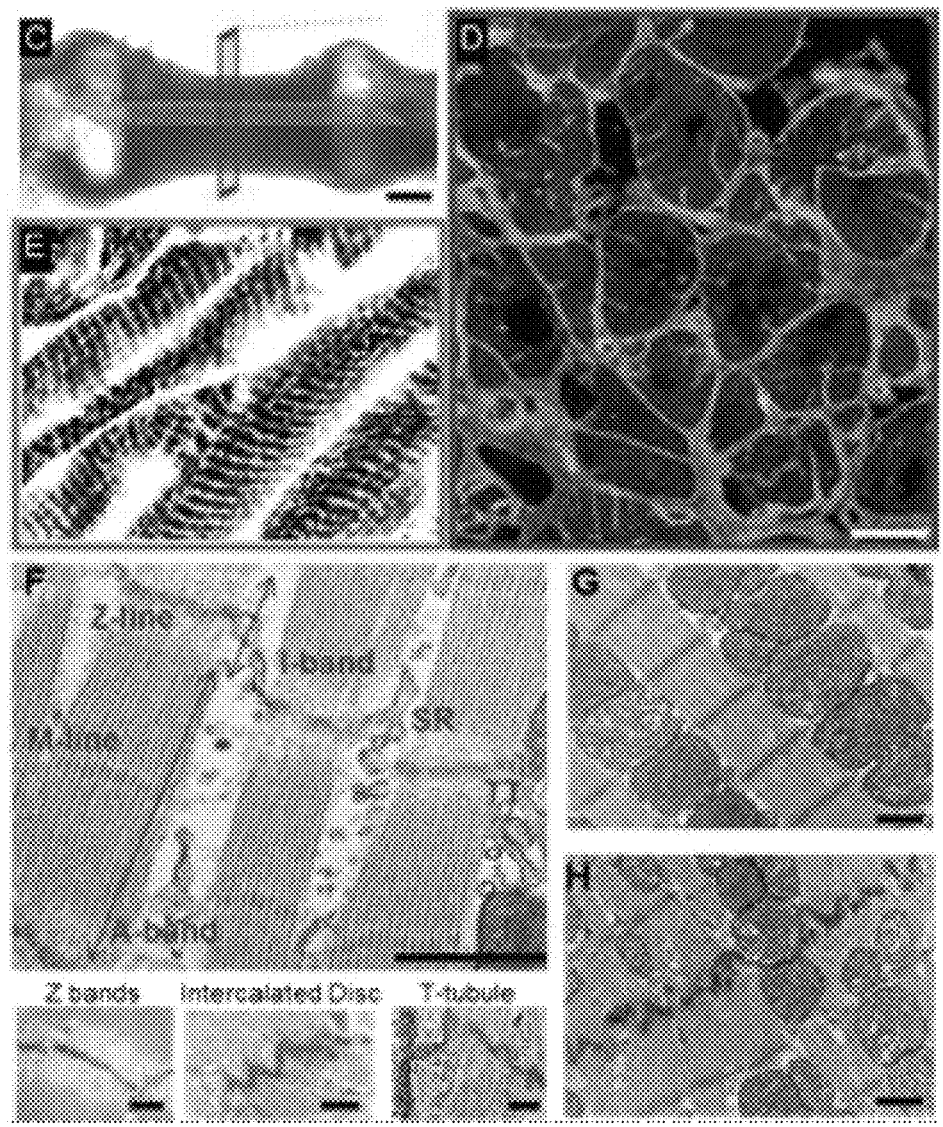

FIG. 41 shows organoids with ultrastructures.

Figure 42:
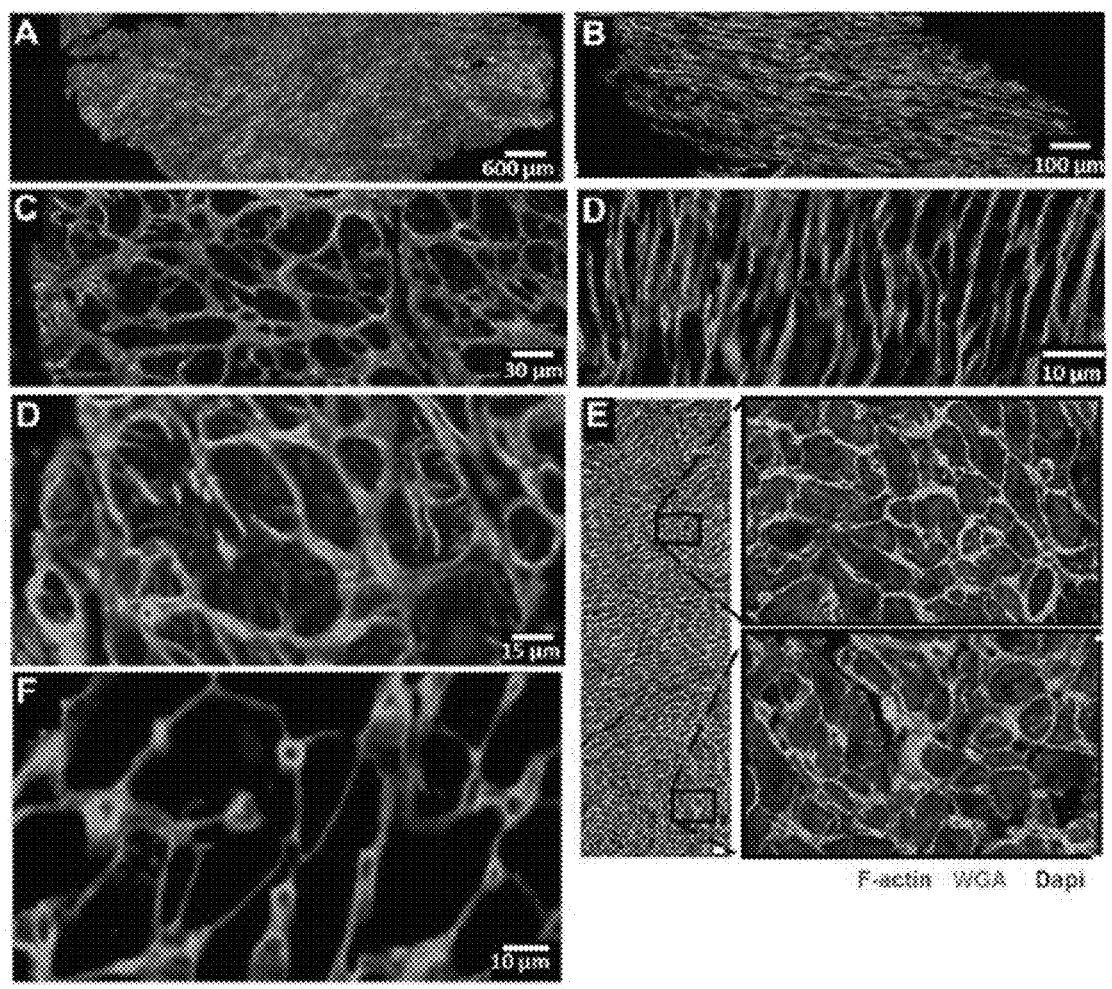

FIG. 42 shows networks of T-tubules were present in both the longitudinal and axial orientation beginning at 2 weeks in intensity-trained organoids.

Figure 43A:
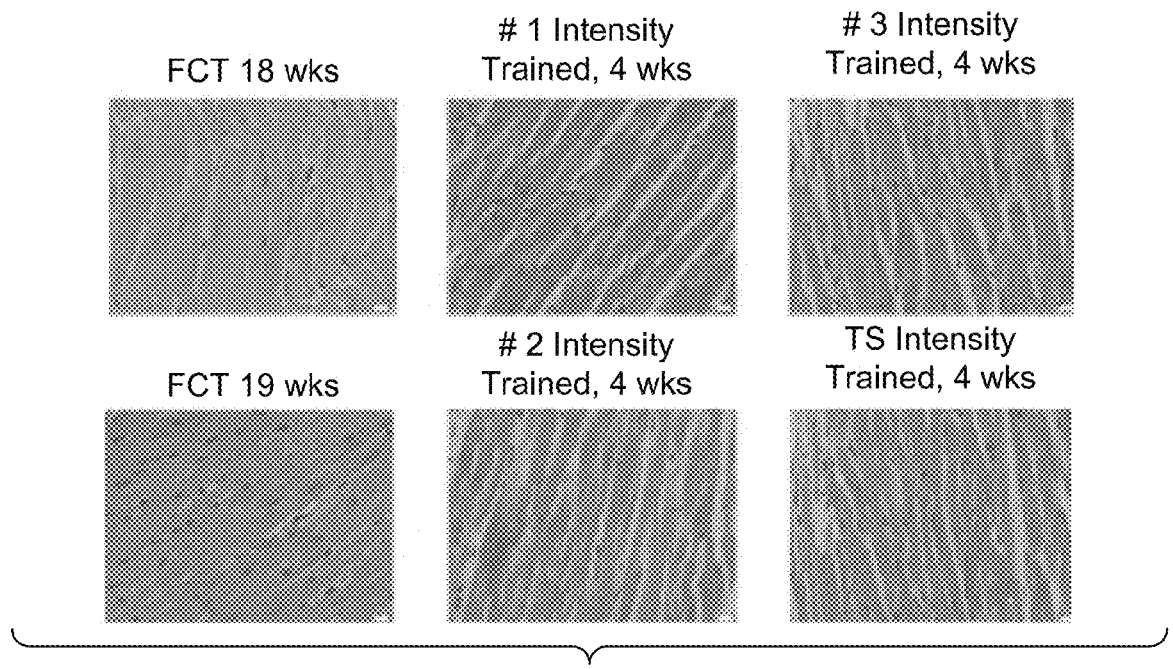
Figure 43B:
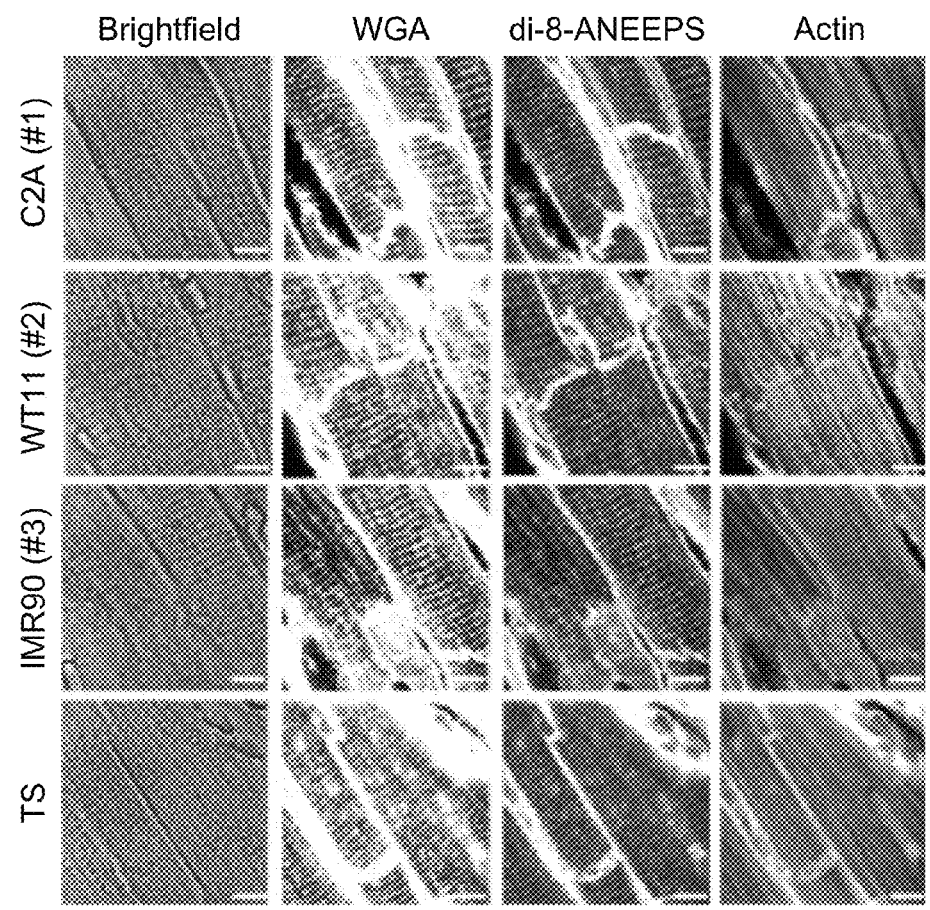

FIGS. 43A and 43B show that Timothy Syndrome organoids displayed morphological ultrastructure.

Figure 44A:
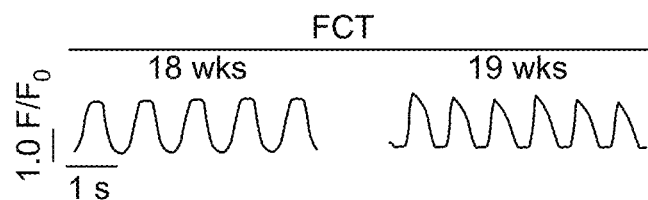
Figure 44B:
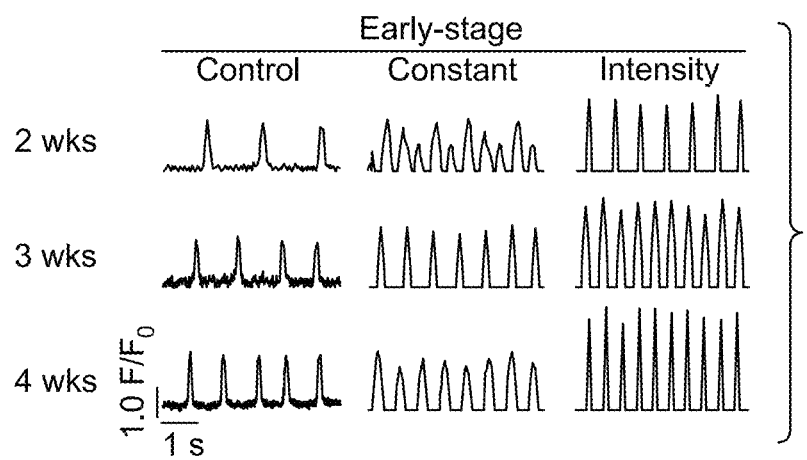
Figure 44C:
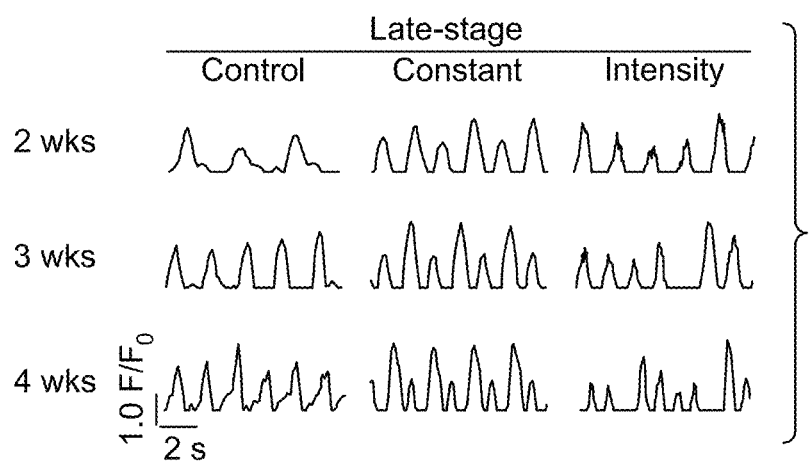

FIGS. 44A to 44C illustrate adult-like contractile behavior and gene expression in a design where early-state or late stage iPS-CMs and supporting fibroblasts were encapsulated in fibrin hydrogel to form organoids stretched between two elastic pillars and forced to contract by electrical stimulation.

FIGS. 45A to 45E illustrate ultrastructural features for early-stage organoids.

FIGS. 46A to 46J illustrate data from calcium handling of organoids in accordance with the described subject matter.

FIGS. 47A to 47L illustrate gene expression within cardiac organoids over time in accordance with the described subject matter.

Figure 48A:
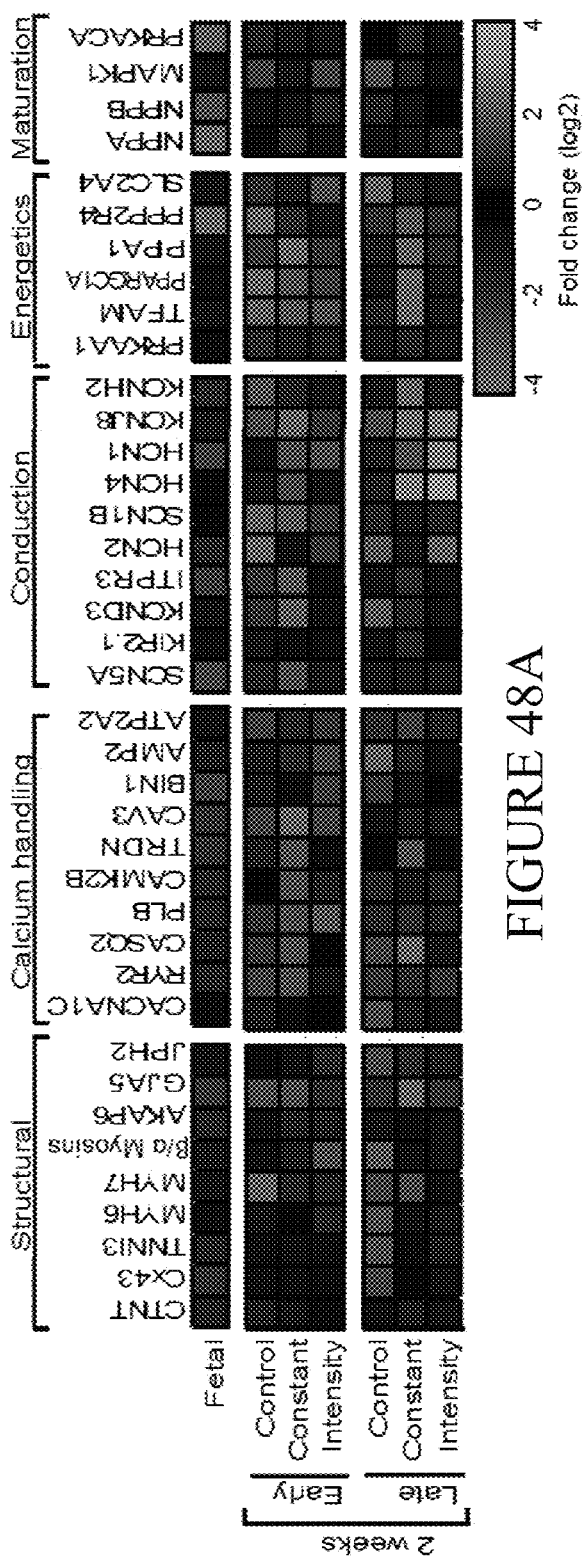
Figure 48B:
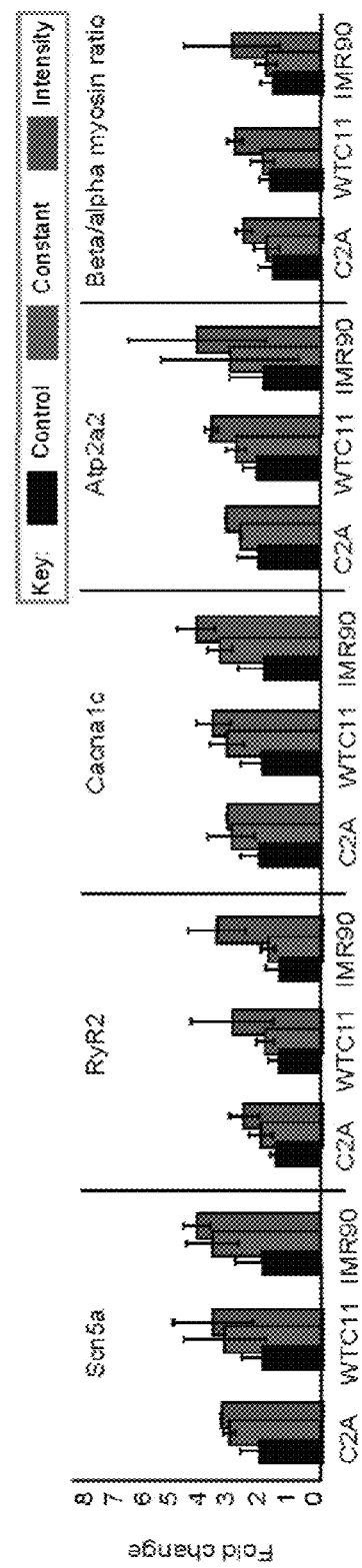

FIGS. 48A and 48B show data for early-stage intensity training and mitrochondrial maturation.

Figure 49A:
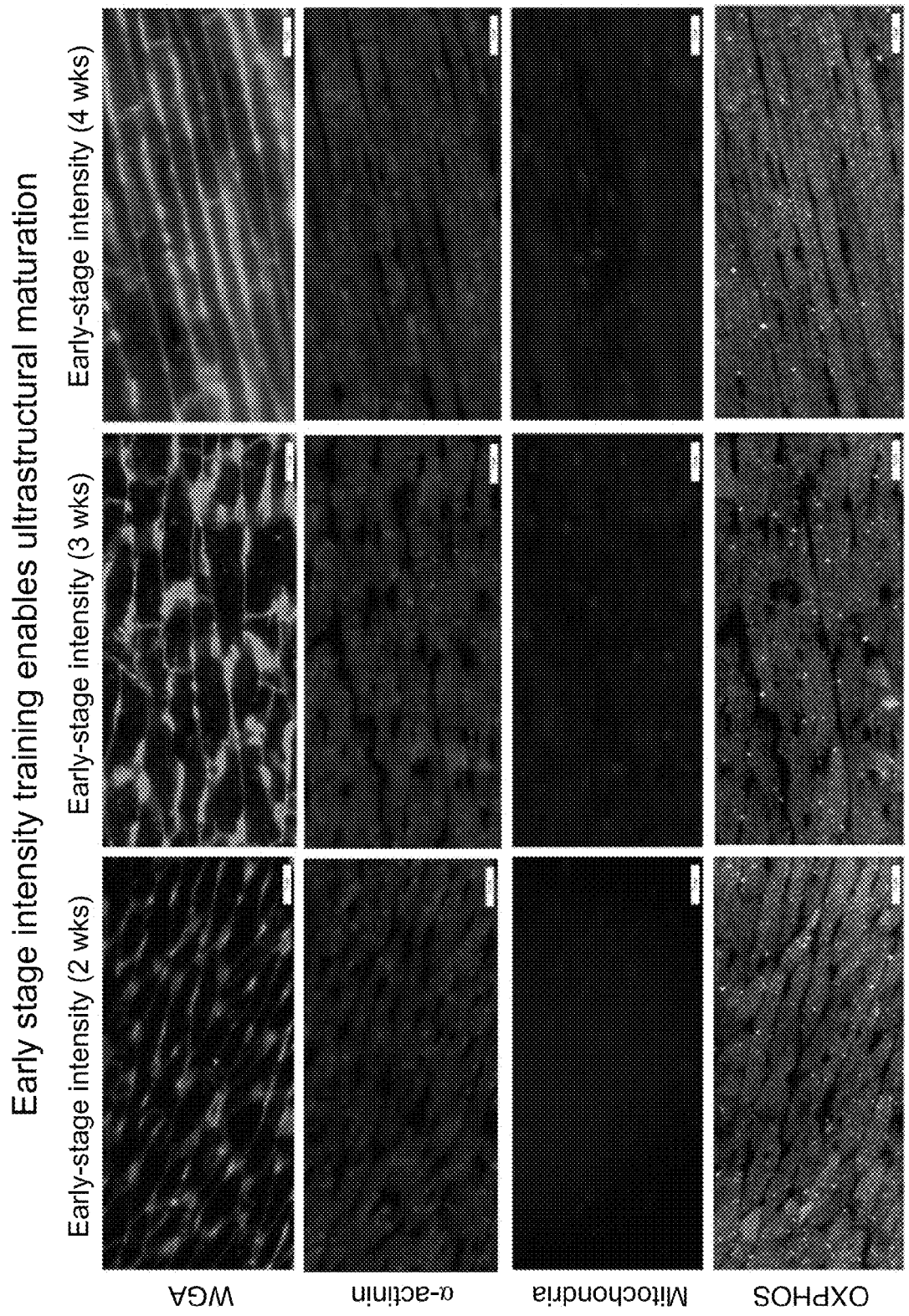
Figure 49B:
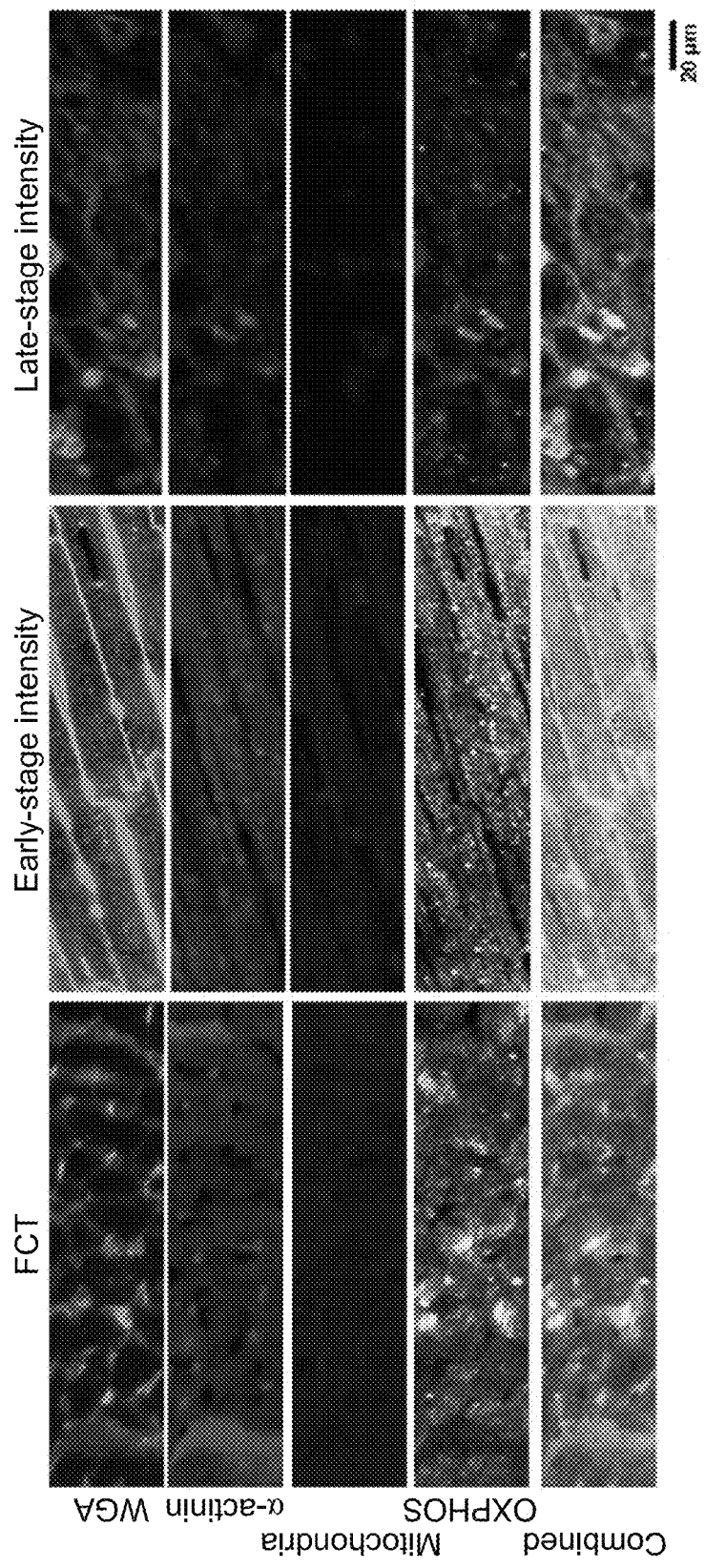

FIGS. 49A and 49B show extended data of cardiac maturation over time in response to intensity training.

Figure 50A:
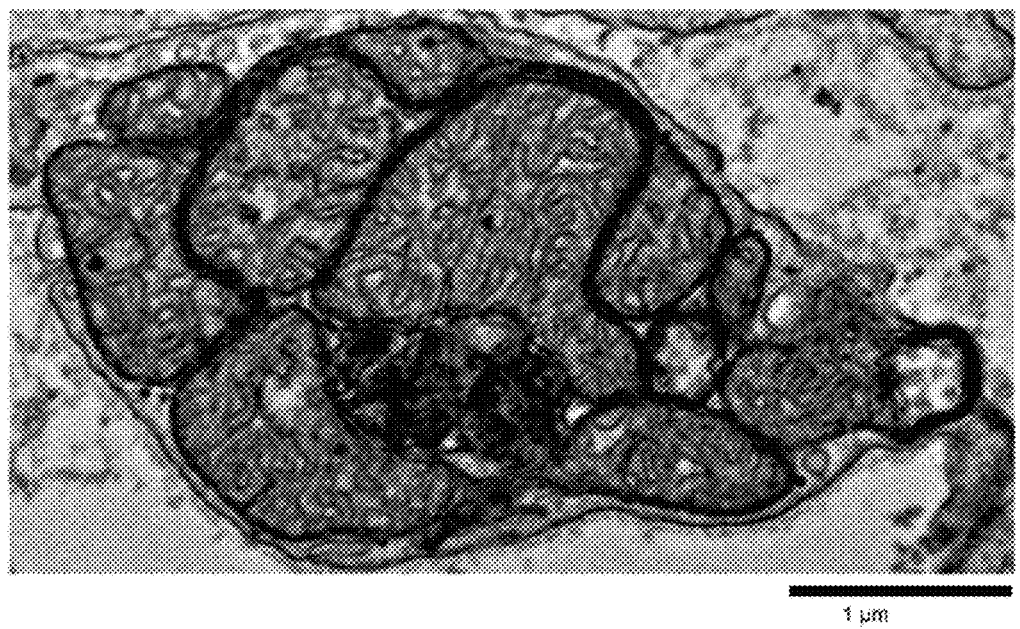
Figure 50B:
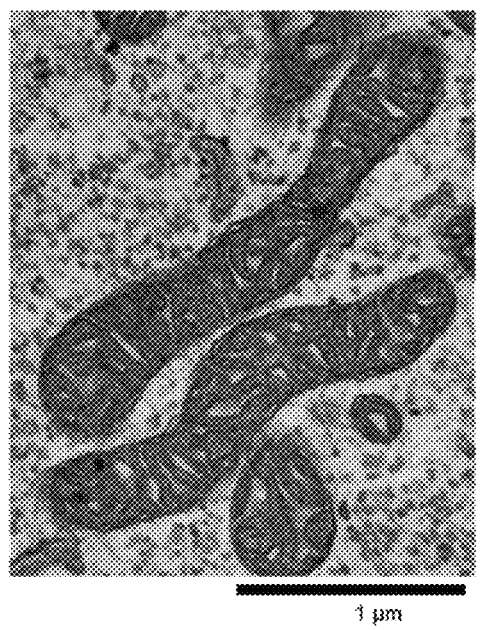

FIGS. 50A and 50B show TEM images for early-stage and late-stage hiPS-CM organoids.

FIG. 51 shows physiological responses of the engineered tissues grown under the intensity training regimen to the drug isoproterenol.

Figure 52:
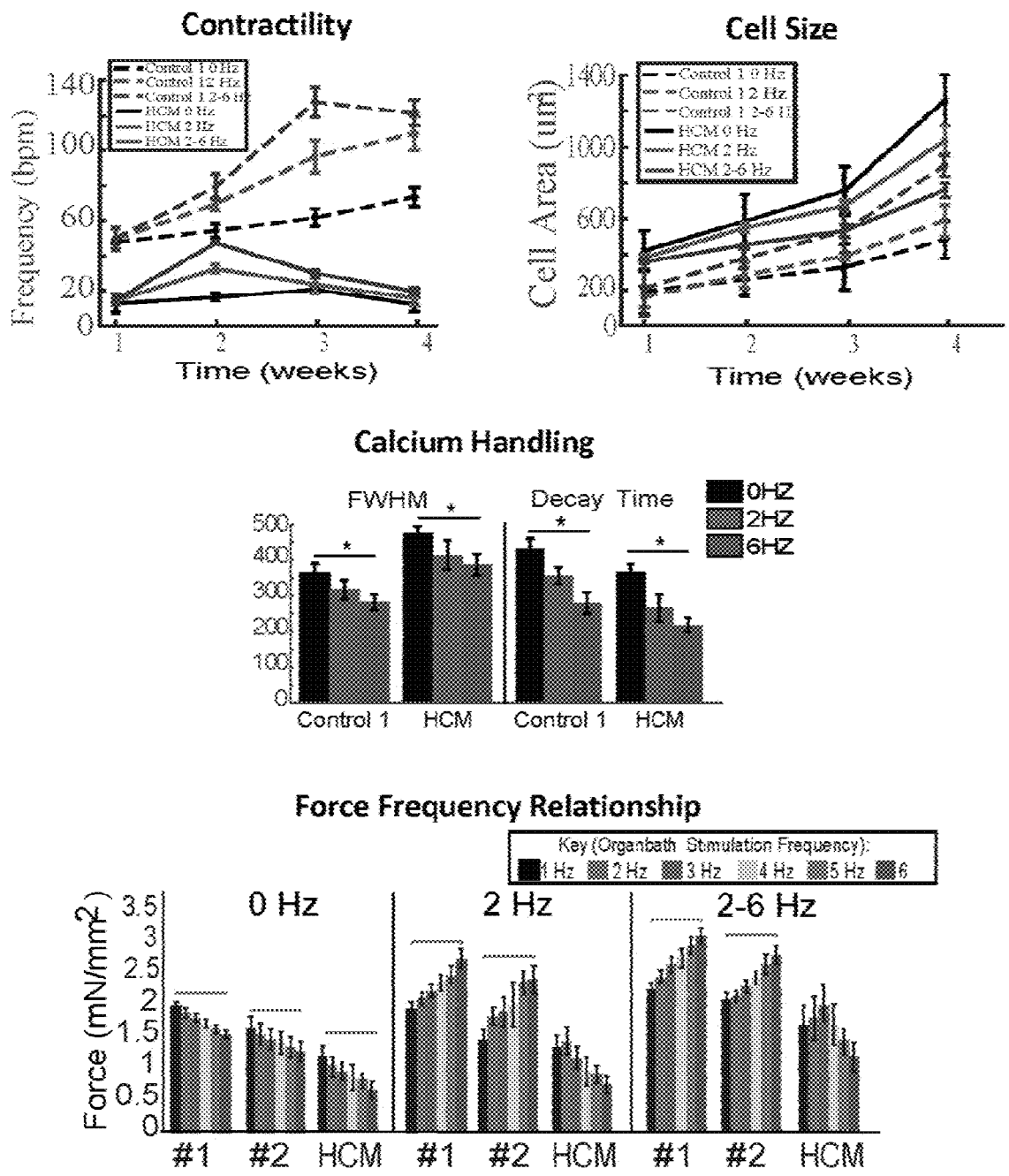

FIG. 52 shows modeling pathological diseases such as cardiac hypertrophy.

FIGS. 53A-53G show preliminary cardiac tissue data.

Figure 54:
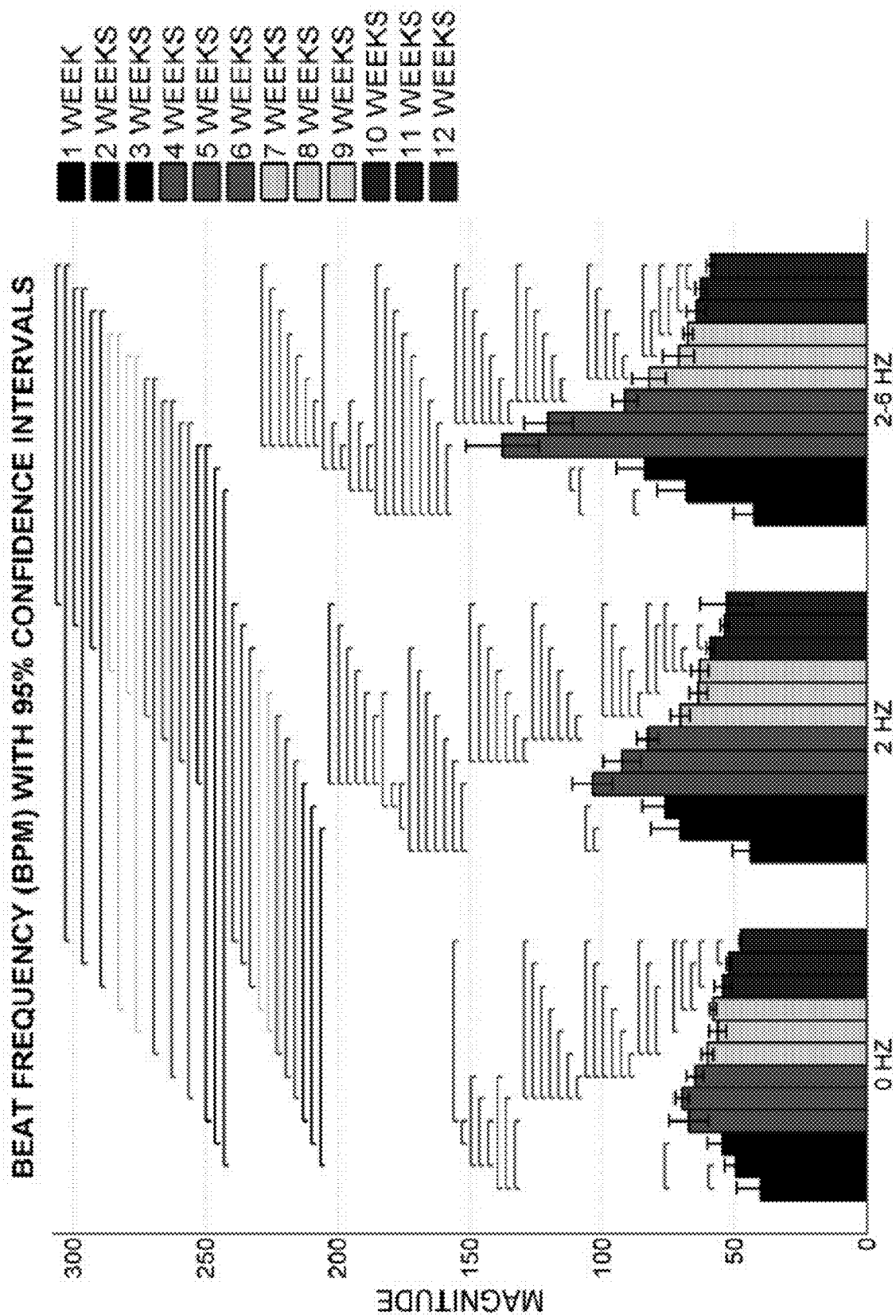

FIG. 54 depicts beat frequency over 12 weeks.

Figure 55:
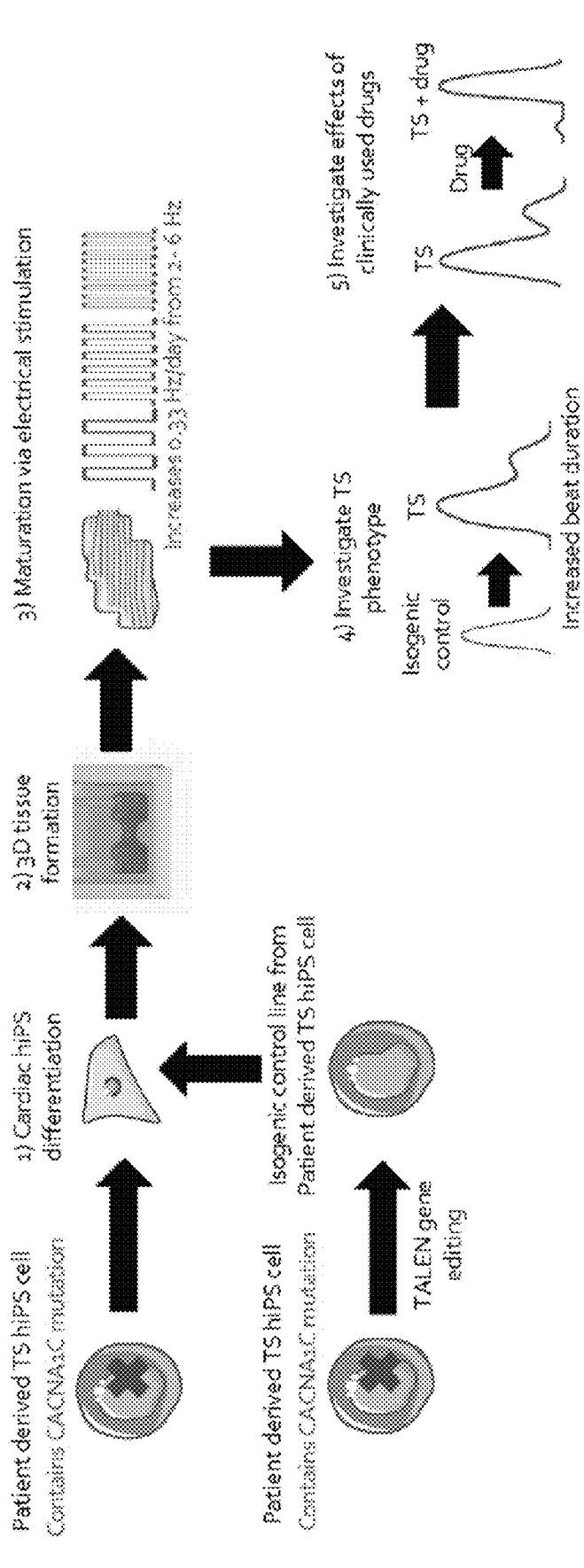

FIG. 55 depicts process for forming personalized organoids.

FIG. 56 shows varying electromechanical stimulation regimens mimic heathy heart regimens.

Figure 57A:
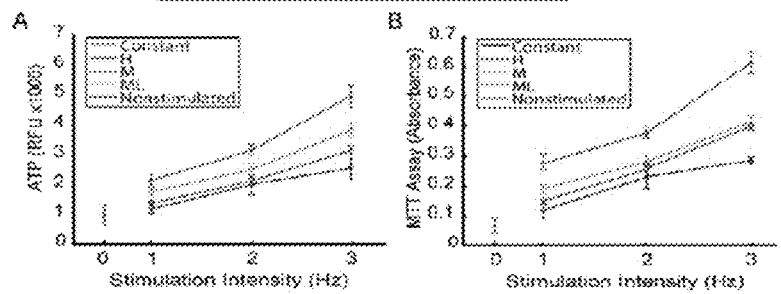
Figure 57B:
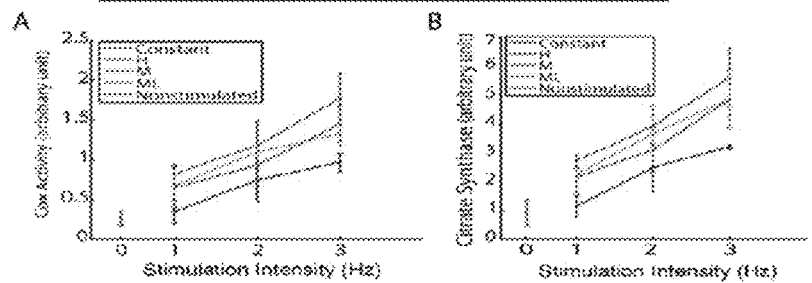
Figure 57C:
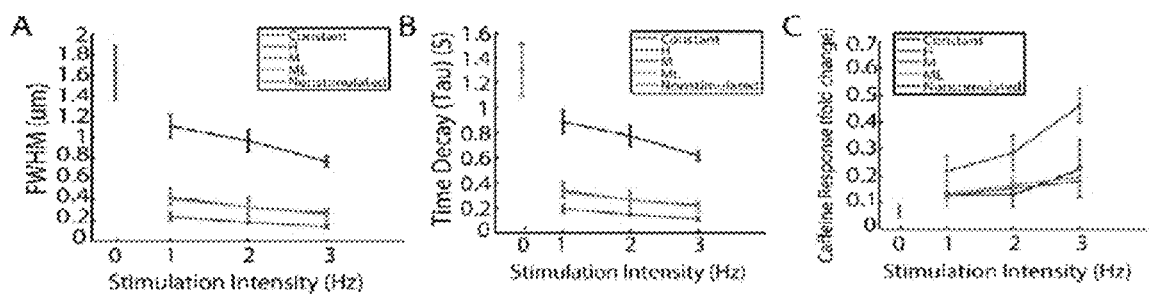

FIGS. 57A to 57C depict changes in enhanced energetics, metabolic activity and calcium handling.

DETAILED DESCRIPTION OF EXEMPLARY EMBODIMENTS

Reference will now be made in detail to exemplary embodiments of the disclosed subject matter, an example of which is illustrated in the accompanying drawings. The method and corresponding steps of the disclosed subject matter will be described in conjunction with the detailed description of the system Generally, the described subject matter provides engineered 3-D human tissue and methods to form and mature engineered micro-tissue. The engineered adult-like micro-tissue is suitable for personalized screening and disease modeling. In a first aspect, a method for engineering, three-dimensional, functional, adult-like micro-tissue, is provided. The micro-tissue described includes heart, vascular and tumor tissues to enable measurements of drug interactions. However, the methods and system taught may be extrapolated to other tissues.

The 3-D tissue formed accurately create tissue having mature adult-like phenotype. Thus, it can be used for assays such as strain mapping, force analysis, and voltage mapping to measure a drug's impact on function at the tissue level, for example, cardiac function at a tissue level.

In one aspect, a method if provided for deriving cells of a particular lineage from a single line of induced pluripotent stem (iPS) cells obtained from a healthy individual. Biophysical regulation of the fate and function of stem cells and their differentiated progeny can be achieved by using molecular, cellular, matrix-derived and physical factors. For example, differentiation of stem cells into endothelial and cardiac lineages may be directed. Accordingly, derivation of multiple micro-tissues starting from a single population of human iPS can provide a large genotype pool for healthy cells and cells with genetic mutations. This is useful especially when the micro-tissue is used for drug screening and modeling of disease.

Figure 1:
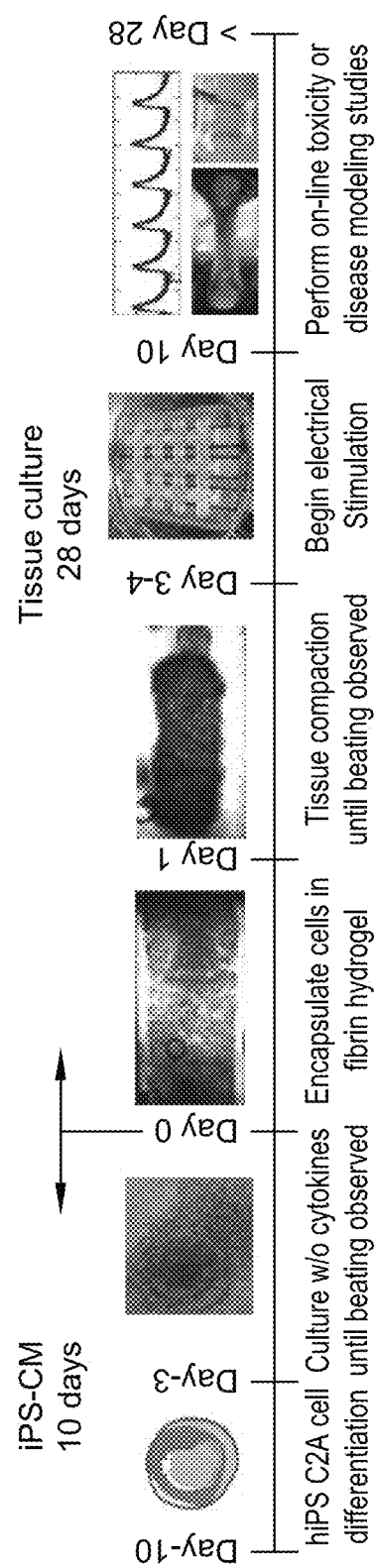
FIG. 1 depicts a method including encapsulating the resulting iPS cardiomyocytes in a hydrogel after a period of 8-10 days.

FIG. 1, as embodied herein, shows a method using iPS cells differentiated towards a cardiac lineage. Differentiation of iPS cell lines into contractile cardiomyocytes, such as iPS C2a, is suitable. It has been found that staged molecular induction from one particular iPS cell line yields about 85% of differentiated cardiomyocytes (as evaluated by Troponin staining and contractile function). Several variations of staged molecular induction in different settings, such as embryoid bodies, mono layers and pseudo-monolayers, however, may be used. By micromanipulation (picking of beating areas), the yield can be increased to about >80%. Microfluidic platforms may be instrumental in the development of protocols for directed differentiation of stem cells obtained from healthy individuals and patients with inherited or acquired heart disease.

As shown in FIG. 1, the method includes encapsulating the resulting iPS cardiomyocytes in a hydrogel after a period of 8-10 days. The iPS cell derived cardiomyocytes are electromechanically functional but immature. The encapsulated iPS cardiomyocytes are conditioned to induce cell maturation, by exposing the derived cells to electromechanical stimuli that increase in intensity over a period of 4 weeks. For example, but not limitation, electromechanical conditioning is applied, following molecular induction (8 days, 3 V/cm, 2 ms square waves, frequency=2-6 Hz). Electrical stimulation is applied at either a constant frequency of 2 Hz for 4 weeks, or at a frequency that increases gradually from 2 Hz at the end of week 1 to 6 Hz over a 2-week time period, and at 6 Hz for one more week. Electrical stimulation applied in this manner increased the strain of contractions in cardiac micro-tissues. In parallel, the contractions became synchronized and the strain generated by cardiac micro-tissues increased as the stimulation frequency increased. In some embodiments, the electromechanical conditioning may begin three to four days after encapsulation of the iPS cells.

The cells typically begin beating after 8-10 days of differentiation and can be used for tissue formation within the bioreactor platform. The bioreactor platform delivers physiologically relevant stimuli, such as passive tension that directs the cells towards anisotropic alignment, electrical stimulation to pace the cardiac constructs and enhance electrical synchronicity within the tissue. In some embodiments, the method includes on-line analysis readouts that do not directly interfere with the tissue or require tissue harvesting at each data point, enabling real-time longitudinal, dynamic studies of tissue responses to drugs and environmental stimuli. Generally, it takes up to four weeks to form the cardiac tissues and mature them to a physiologically relevant level of function, where the tissues can be used to screen for drugs or study various models of disease.

Figure 2A:
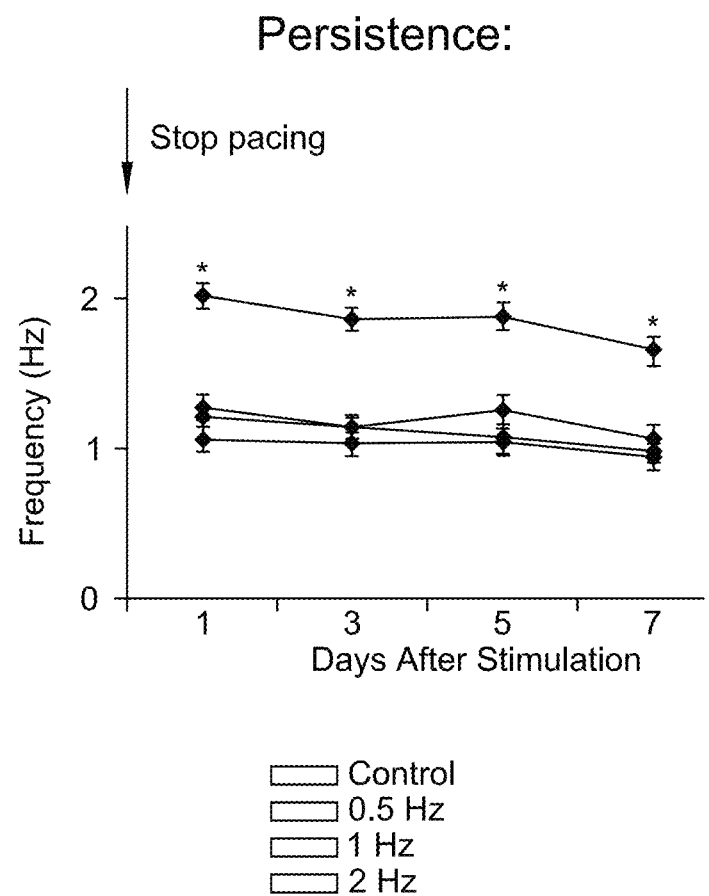
FIGS. 2A and 2B depict graphs showing persistence of the tissue under various levels of electromechanical stimulation for a period of 7 days, and the mechanism, respectively.
Figure 2B:
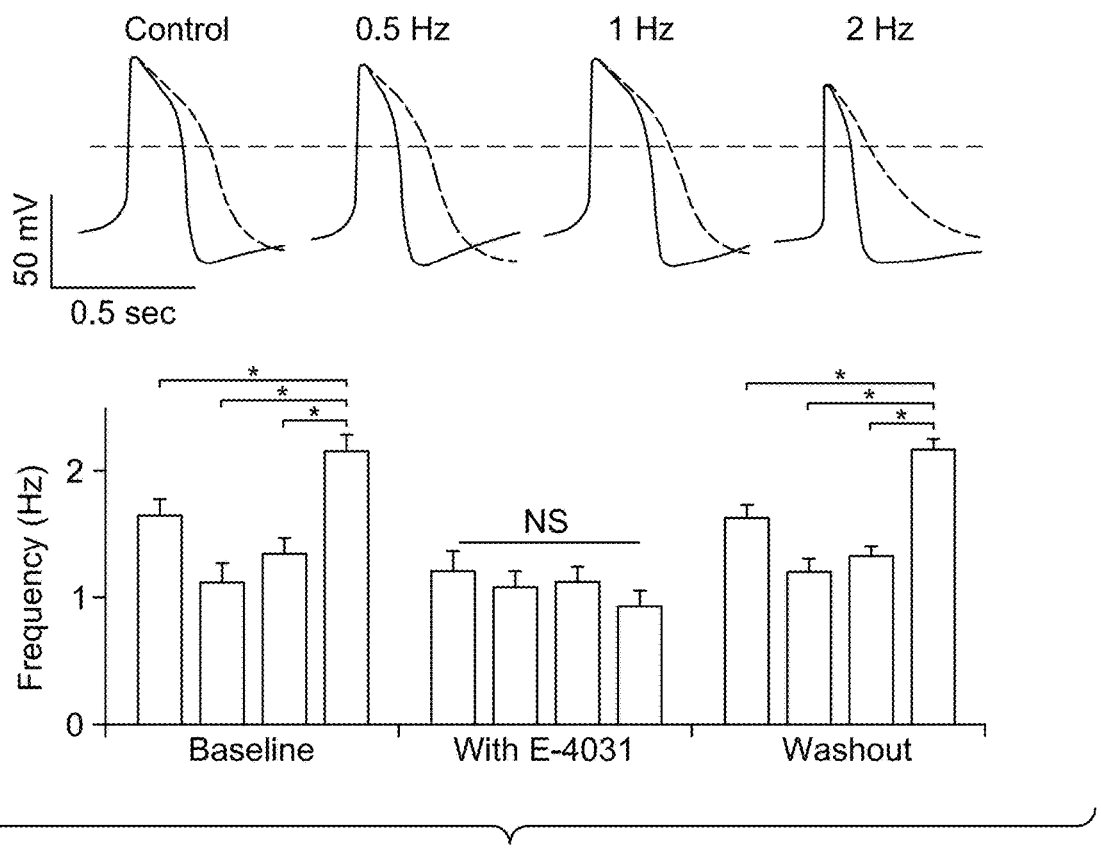

FIGS. 2A and 2B depict graphs showing persistence of the tissue under various levels of electromechanical stimulation for a period of 7 days, and the mechanism, respectively. The resultant iPS cardiomyocytes can be conditioned or trained by inducing them with electrical signals to work against physiological force in order to accelerate and promote their maturation. As electric field signals are present in the myocardium throughout life, the present method mimics these signals by electrically stimulating nascent cardiomyocytes derived from human embryonic and induced pluripotent stem cells. Exposing the cells to electrical stimulation as described matured the cardiomyocytes and induced broad changes in cardiac gene expression, protein organization, and sarcomeric ultrastructure. Stem cell derived cardiomyocytes responded to the electric signals by adapting their autonomous beating rate to the rate which they were stimulated. This rate adaptive effect persisted for a period of time, and was mediated by KCNH2, a voltage gated potassium channel responsible for repolarization, as demonstrated in FIGS. 2A and 2B. Thus, the micro-tissue described herein functions just like a cardiac native tissue, and can be useful, for example, for drug screening or modeling.

Figure 3:
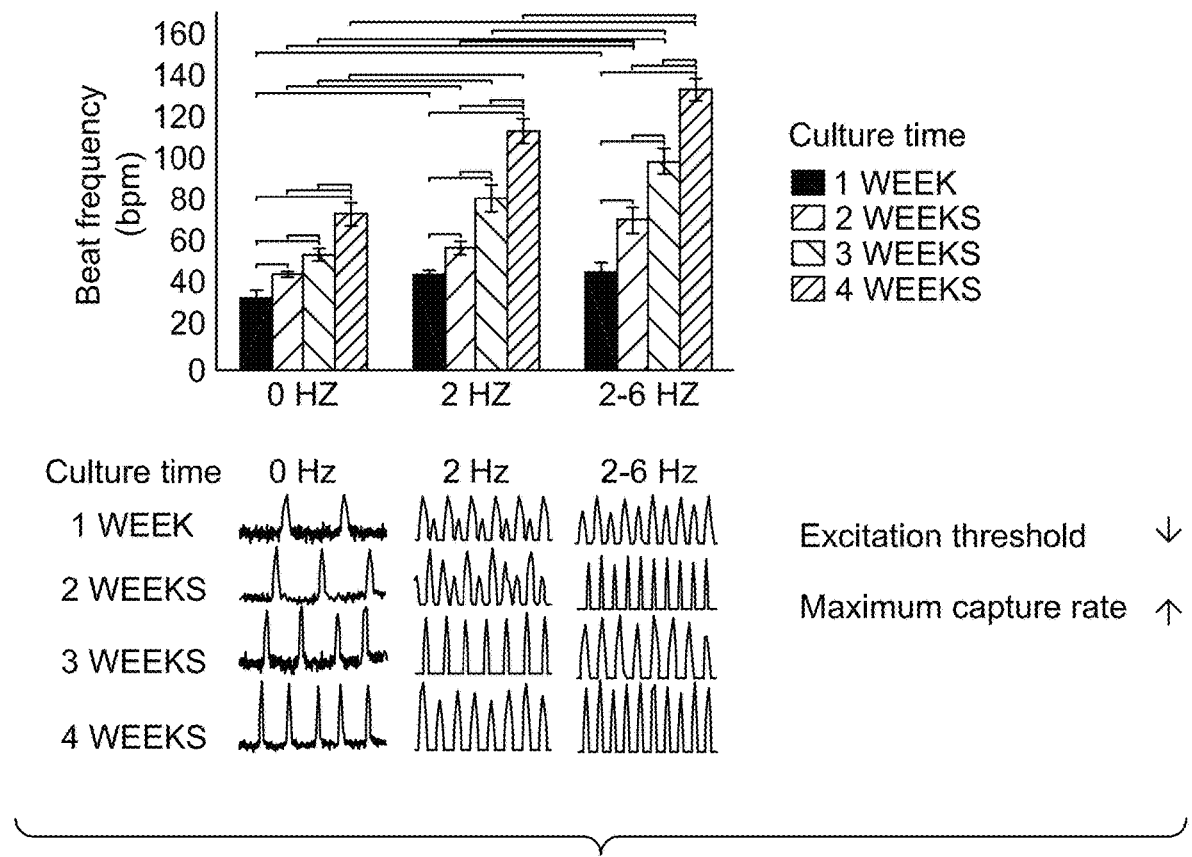
FIG. 3 shows three regimes of electrical stimulation on the encapsulated cardiomyocytes.

FIG. 3 shows three regimes of electrical stimulation on the encapsulated cardiomyocytes. The three regimes of electrical stimulation were: 0 Hz, 2 Hz, and 2-6 Hz (2 Hz @ day 7-6 Hz @ day 19, 0.33 Hz per day). The stimulation enhanced tissue maturation over time as seen by the more regular contraction profile, and increases in frequency and amplitude of contractions. The excitation threshold (ET) decreased and the maximum capture rate (MCR) increased consistent with tissue maturation. As used herein, excitation threshold (ET) refers to the minimum voltage required to elicit synchronous contractions from the tissue. Generally, more mature tissues are more electrically coupled and, thus, will exhibit a lower ET. As used herein, maximum capture rate (MCR) refers to the maximum frequency at which the tissue can synchronously beat. Generally, more mature tissues exhibit a higher MCR. It would be appreciated by a skilled artisan that these are standard measurements of the ability of a tissue to transmit electric signals.

Figure 4:
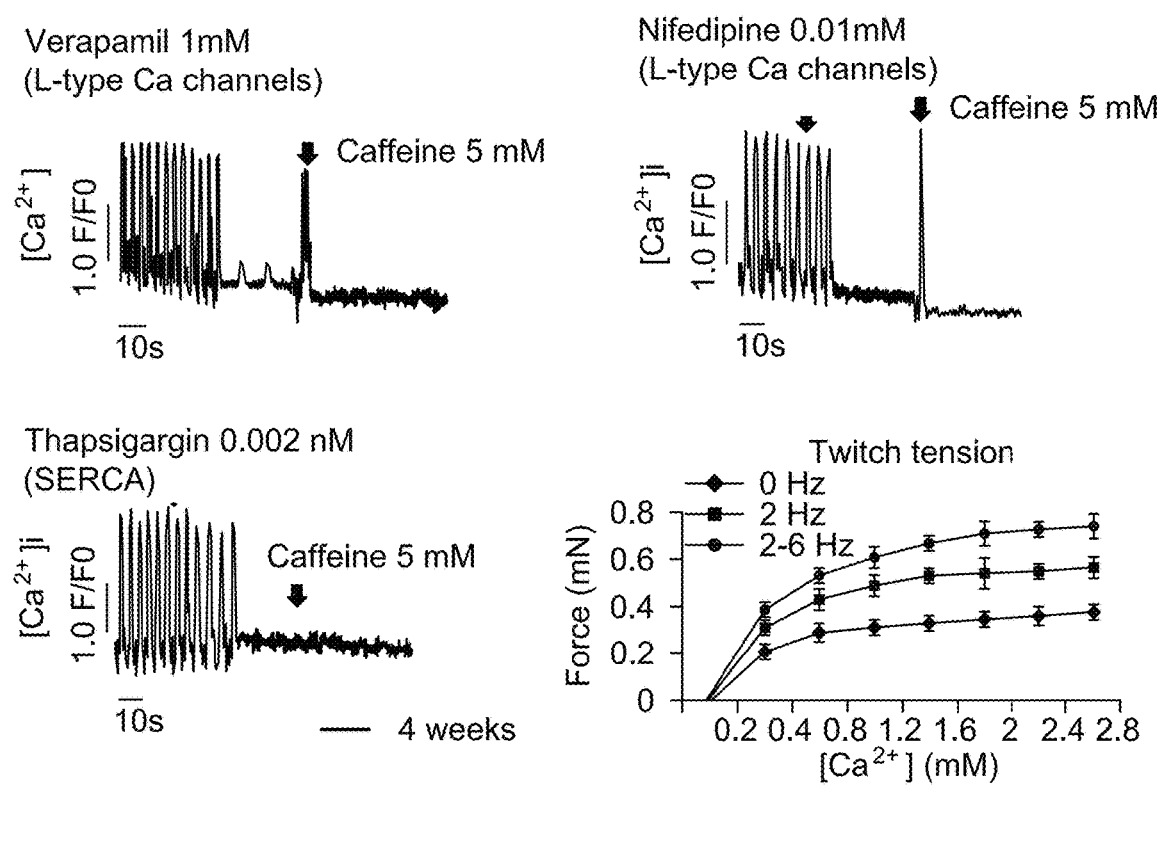
FIG. 4 shows engineered tissue in accordance with the described subject matter screened for caffeine and verapamil handling.

The engineered tissue in accordance with the described subject matter screened for caffeine handling, as shown in FIG. 4. Investigating the Ca signals within the engineered tissue reveal a greater response to caffeine over both time and with electrical stimulation. FIG. 4 also depicts probing the Ca handling properties by blocking the L-type $Ca^{2+}$ channels via administration of verapamil, which resulted in the cessation of Ca2+ transients until adding caffeine enabled the release of intracellular Ca2+ into the cytosol. Also shown is how Thapsigargin raises cytosolic Ca concentration by blocking the ability of the cell to pump calcium into the sarcoplasmic and endoplasmic reticula which causes these stores to become depleted. The ability of the tissue to respond to caffeine reveals that is has the ability to store calcium in the sarcoplasmic reticulum. The ability to store calcium acts as a reservoir so that, at increased contractile demands, the tissue can respond appropriately, which closely parallels the natural physiologic response and enables more accurate drug screening, particularly for stimulants or beta-antagonists. Although this screen is limited to caffeine handling, it is representative of a method of drug screening using the engineered 3-D cardiac micro-tissue. For example, the 3-D adult cardiac micro-tissues are useful for screening particular drugs on the cardiac tissue, e.g., Vioxx™, or other drugs suspected by hERG as causing QT prolongation or other issues.

Figure 5:
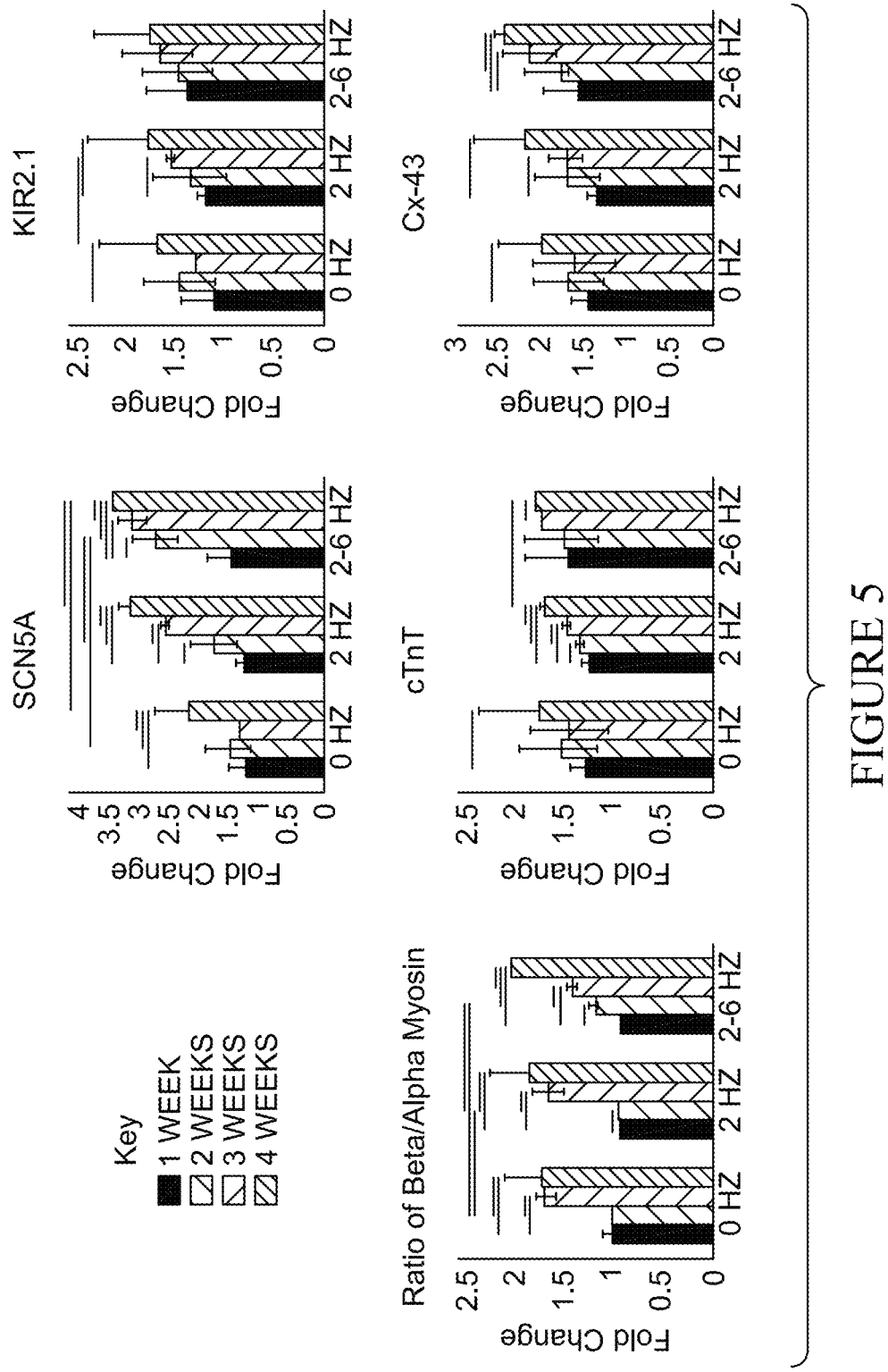
FIG. 5 shows graphs depicting the changes in gene expression over four weeks for SCN5A.

As described supra, exposing the cells to electrical stimulation in the manner described above matured cardiomyocytes, and induced changes in cardiac gene expression. FIG. 5 shows graphs depicting the changes in gene expression over four weeks for SCN5A, which regulates synthesis of sodium channels, KIR2.1, inward-rectifier potassium channel, the ratio of Beta-Alpha myosin, which represents mature-immature form of MEW, cTnT, which encodes the tropomyosin-binding subunit of the troponin complex, and Cx-43, the gap junction protein. Intensity-driven expression of SERCA and NCX should enhance sequestration and extrusion of calcium, enabling the iPS-CMs to relax more quickly and respond to subsequent contractile triggers. Constantly increasing the contractile demand within intensity trained ORGANOIDs resulted in the maturation of CM morphology, to increase force production. Overall, the constant increases in contractile demand imposed by increasing the stimuli over time forces the tissue to respond by maturing rapidly in order to consistently keep up with the imposed demands.

Figure 6:
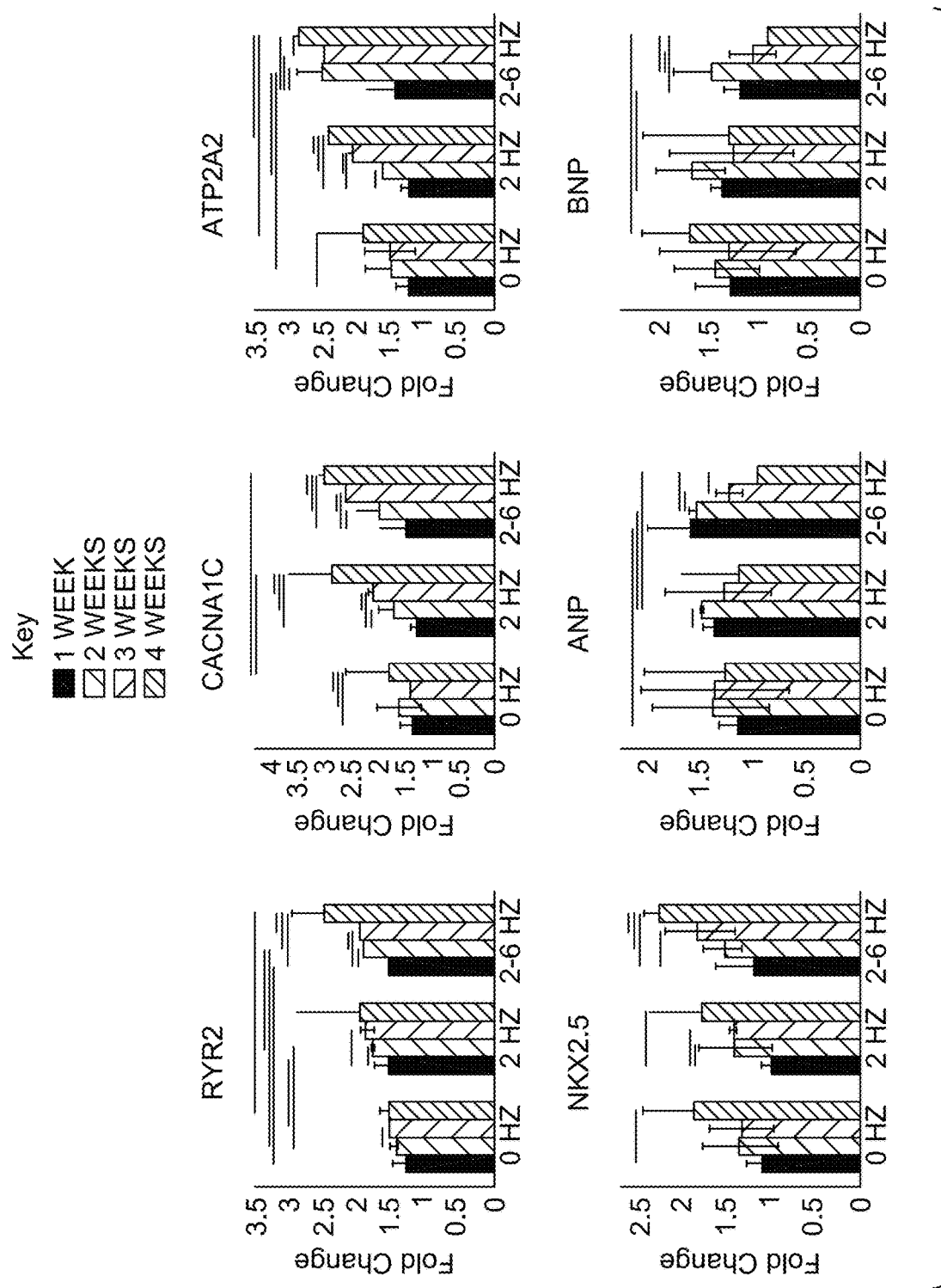
FIG. 6 depicts graphed changes in gene expression over four weeks for RYR2.

FIG. 6 depicts graphed changes in gene expression over four weeks for RYR2, which mediates Ca-induced Ca release from sarcoplasmic reticulum, CACNA1C, a voltage dependent L-type Ca channel, ATP2A2, a Mg-dependent enzyme catalyzes the hydrolysis of ATP coupled with the translocation of Ca from the cytosol to the sarcoplasmic reticulum, NKX2.5, a homeobox protein, key transcription factor of cardiac differentiation and ANP, an atrial natriuretic peptide.

Figure 7:
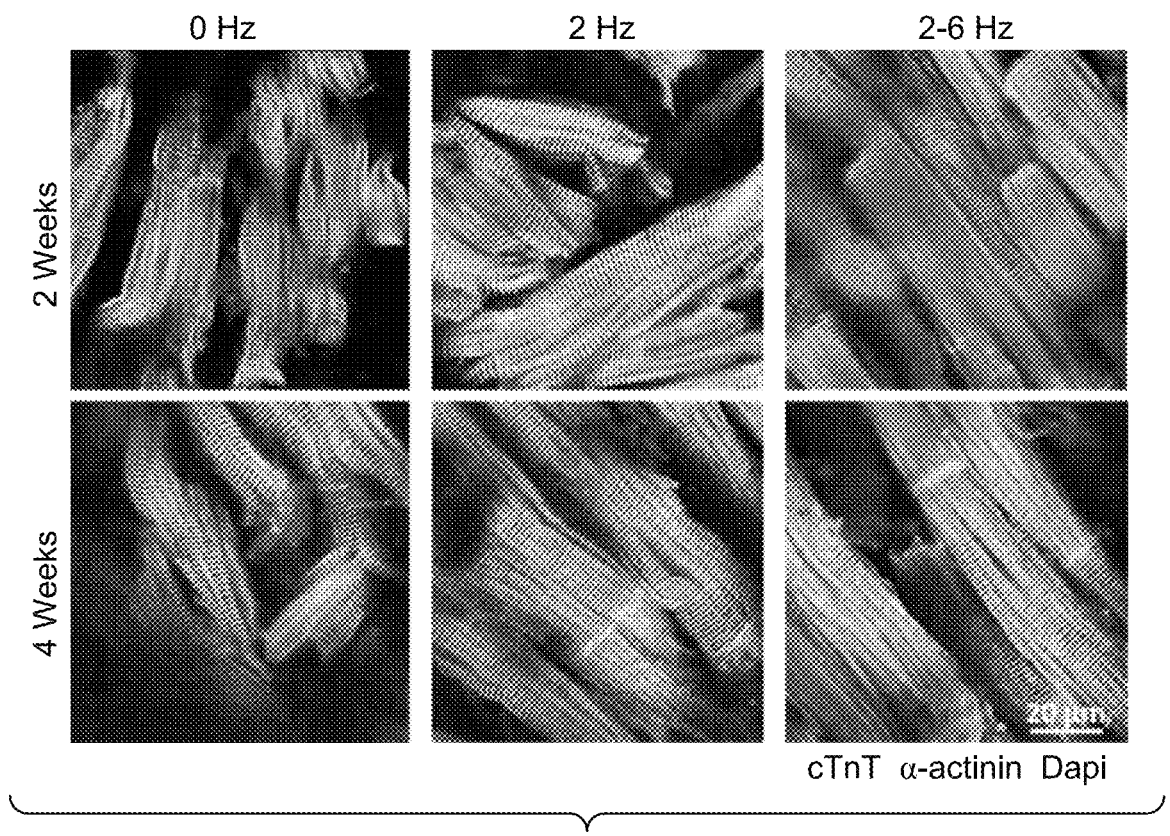
FIG. 7 shows that electromechanical conditioning progressively promoted maturation of cardiac ultrastructures.
Figure 8:
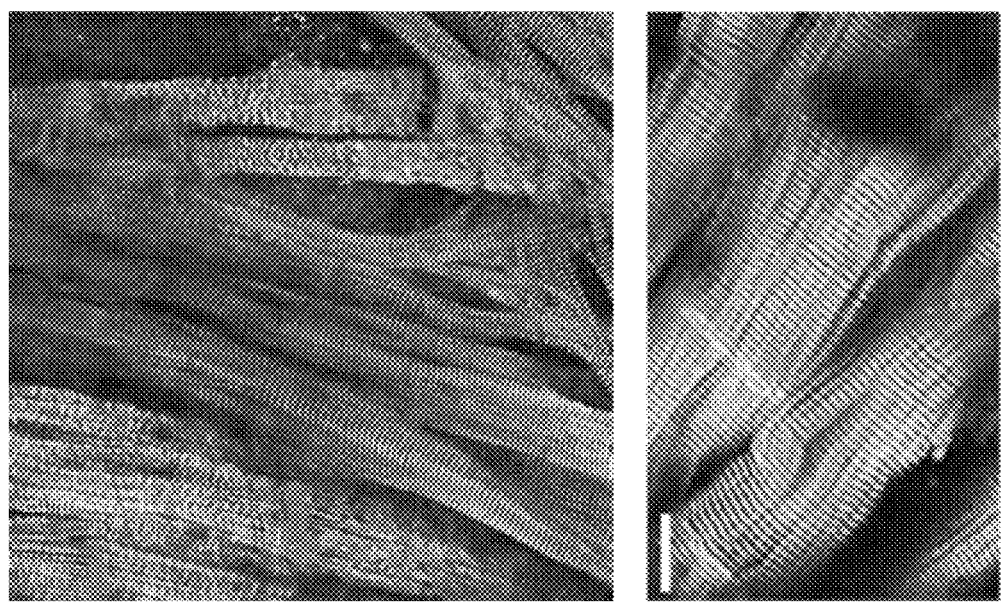
FIG. 8 shows additional ultrastructures after four weeks of culture with electrical stimulation.

It was found that electromechanical conditioning progressively promoted maturation of cardiac ultrastructures as shown in FIG. 7, in a manner dependent on the regime of electromechanical conditioning. Immunofluorescence images of tissue constructs are stained for alpha-actinin (green), cardiac Troponin I (red), and DAPI (blue) (scale bar=10 μm). FIG. 8 shows additional ultrastructures after four weeks of culture with electrical stimulation.

Figure 9:
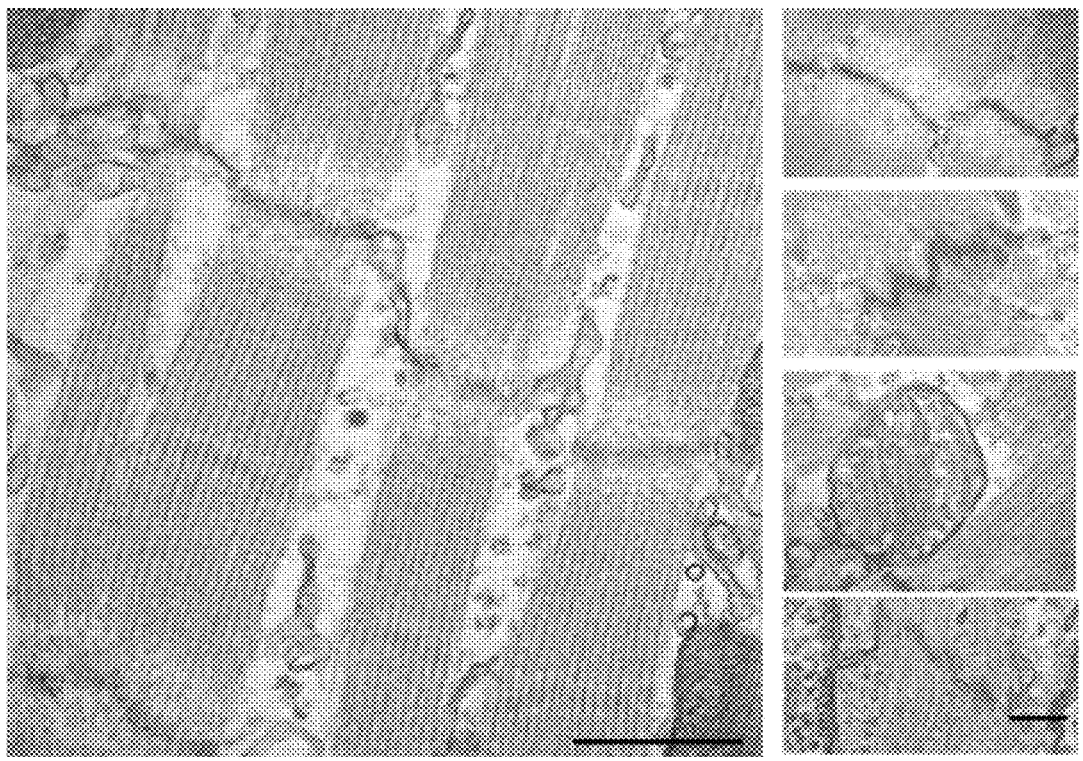
FIG. 9 is a TEM image showing that electromechanical conditioning promotes ultrastructure maturation.
Figure 10:
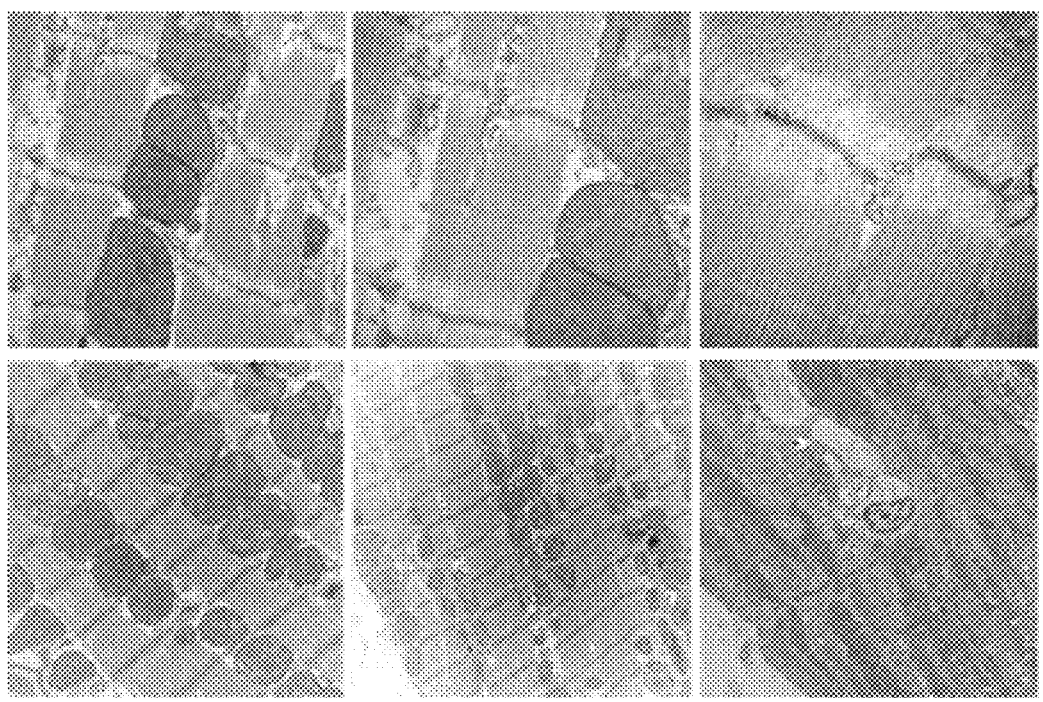
FIG. 10 shows the ultrastructures of the 3D tissue formed by the described method.

FIG. 9 is a TEM image showing that electromechanical conditioning promotes ultrastructure maturation. FIG. 9 shows representative TEM images for cardiac micro-tissues after 4 weeks of culture, and representative TEM images of ultrastructure after 4 weeks of culture under the 2-6 Hz electrical stimulation regimen. (scale bar=1 μm). Z=Z disc; ID=intercalated disc; M=M-line; TT=T-tubules. The ultrastructures of the 3D tissue formed by the described method can be seen in FIG. 10. The micro-tissue includes well-developed registers of sarcomeres, abundant mitochondria, transverse (T) tubules and other ultrastructural features representative of maturing human cardiomyocytes.

Figure 11:
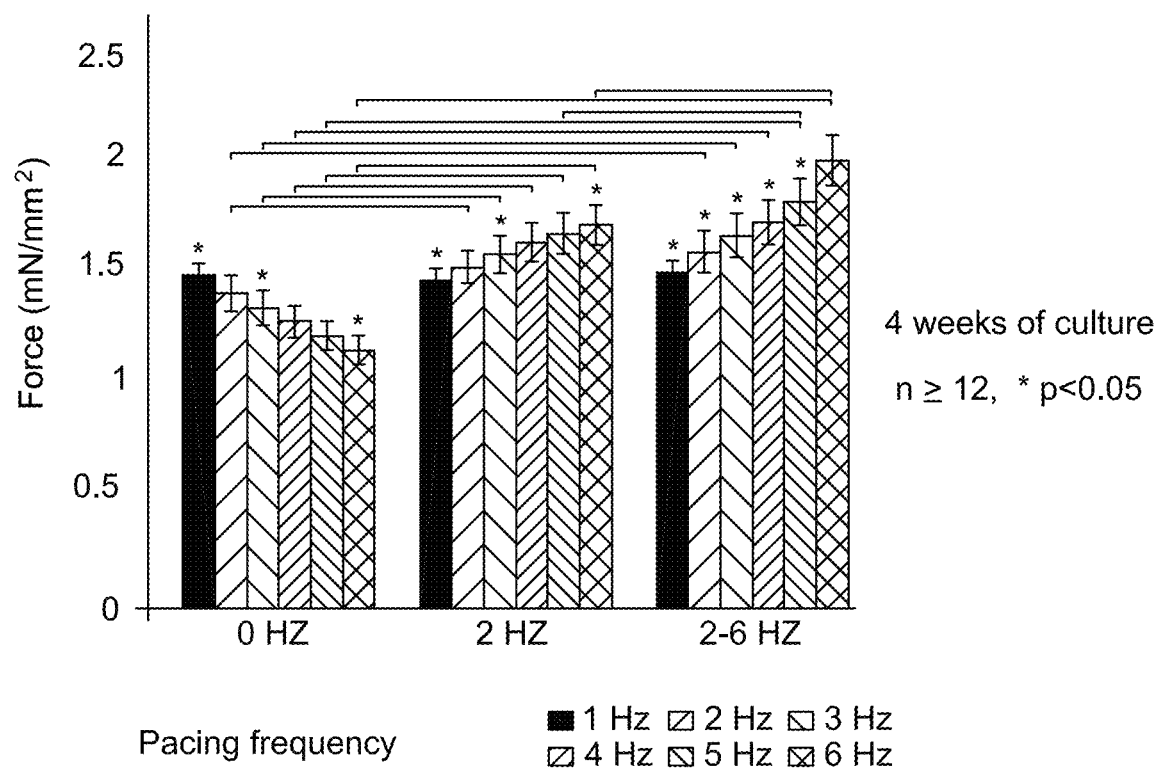
FIG. 11 shows that the cardiac tissue formed according to the disclosed method exhibits a positive force-frequency relationship.

Critically, and not shown before, the cardiac tissue formed according to the disclosed method exhibits a positive force-frequency relationship, as depicted in FIG. 11. This well-established property of healthy adult heart muscle is exhibited in the engineered tissues over both time and, even more so, when electrically stimulated. These tissues can be used for drug screening (e.g., predictive drug screening), disease modeling, and translational medicine since the tissues described herein lack the immature fetal-like phenotype and exhibit a phenotype that is sufficiently similar to the adult-like phenotype, especially with the positive force-frequency relationship it exhibits. Prior efforts to generate cardiac micro-tissues in vitro to date have not been able to recapitulate this effect.

Figure 12:
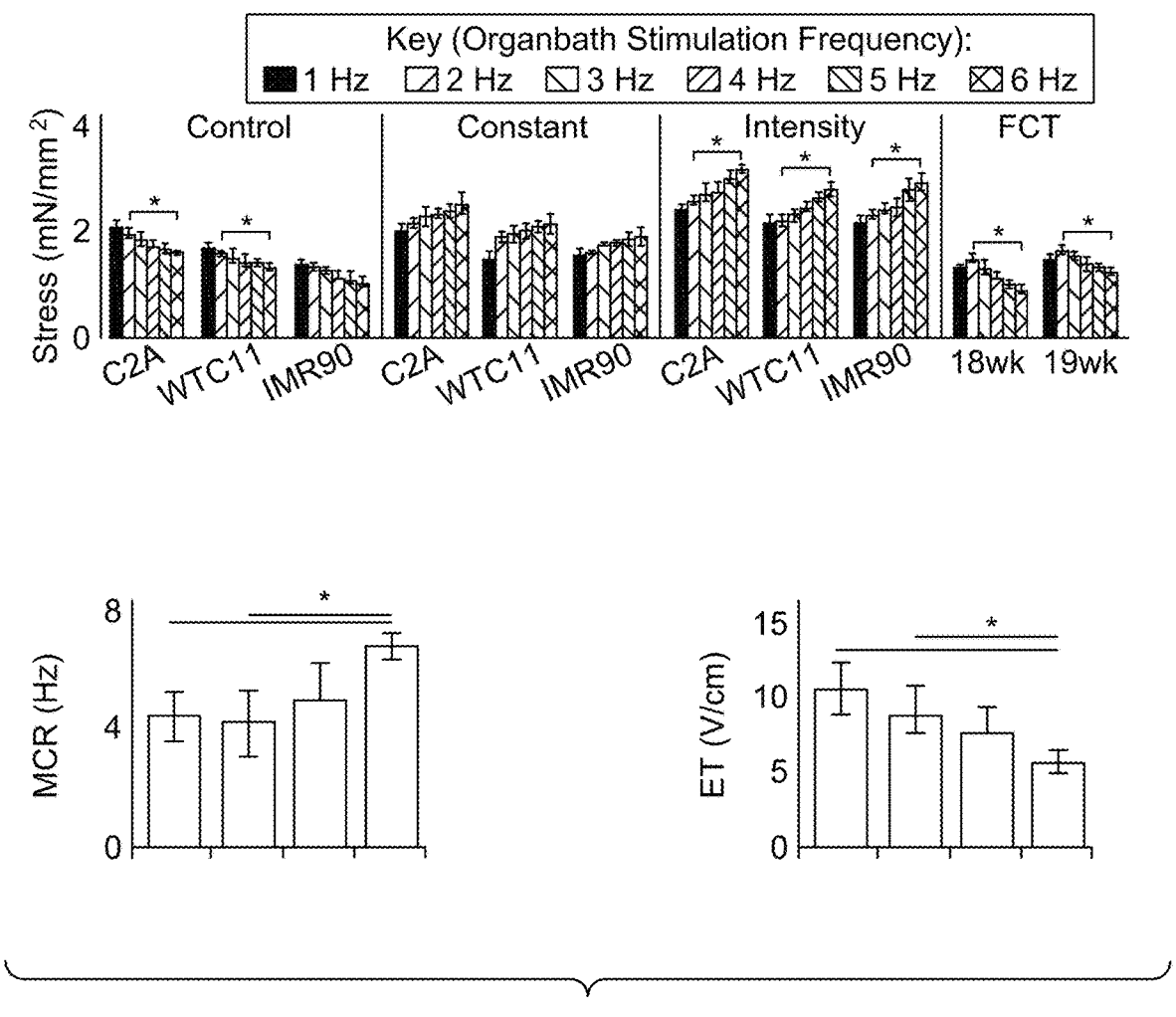
FIG. 12 shows the effects of the described training regimen.

FIG. 12 shows the effects of the described training regimen. The force frequency relationship of organoids grown from three iPS lines (C2A, WTC11, IMR90) over time of culture is depicted. Remarkably, for all three lines of iPS cells, the intensity training regimen resulted in significant increases in the force generated by the engineered heart muscle per unit cross-sectional area (stress) with the increase in stimulation frequency (1-6 Hz). Frequency had no effect on force generation in the constant stimulation group, and had negative effect in the unstimulated control group and human fetal heart muscle. This is the first evidence that the positive force-frequency relationship, which is physiological for healthy adult human heart muscle, can be achieved in human tissues engineered in vitro from iPS cells.

Figure 13A:
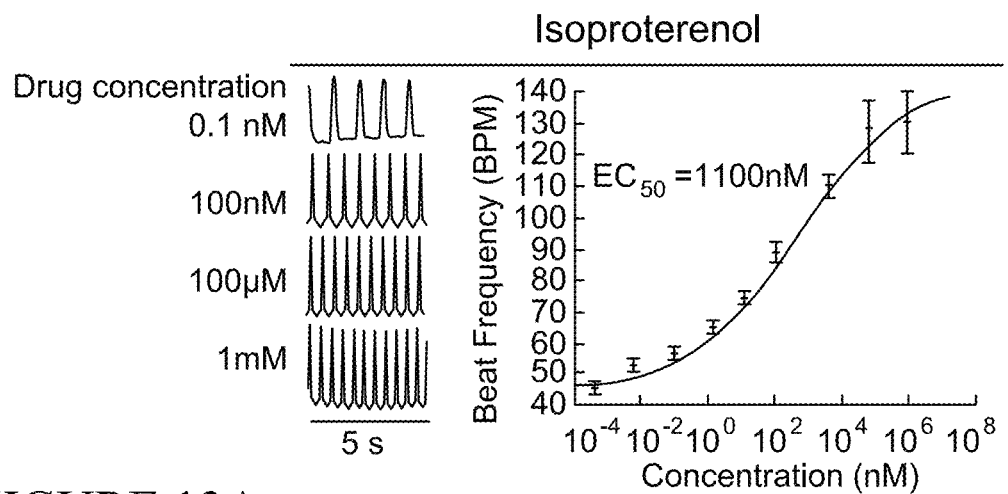
Figure 13B:
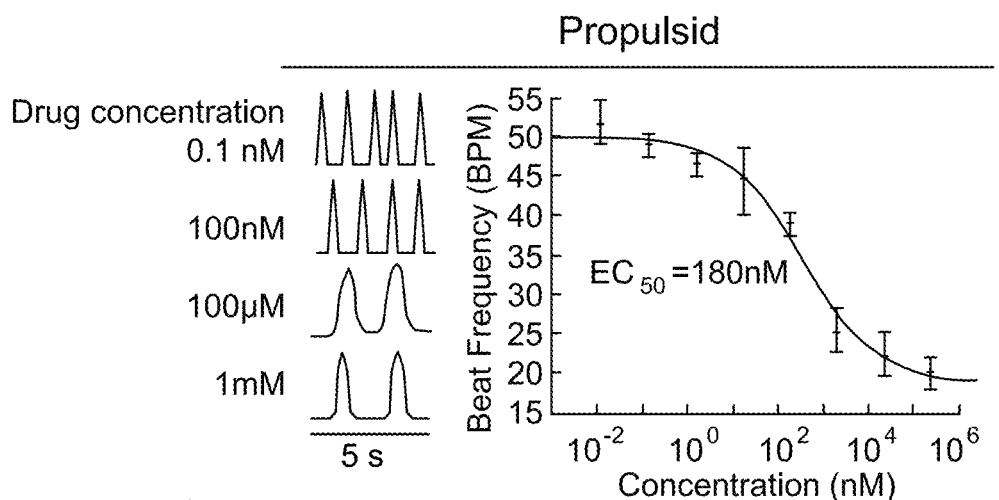
Figure 13C:
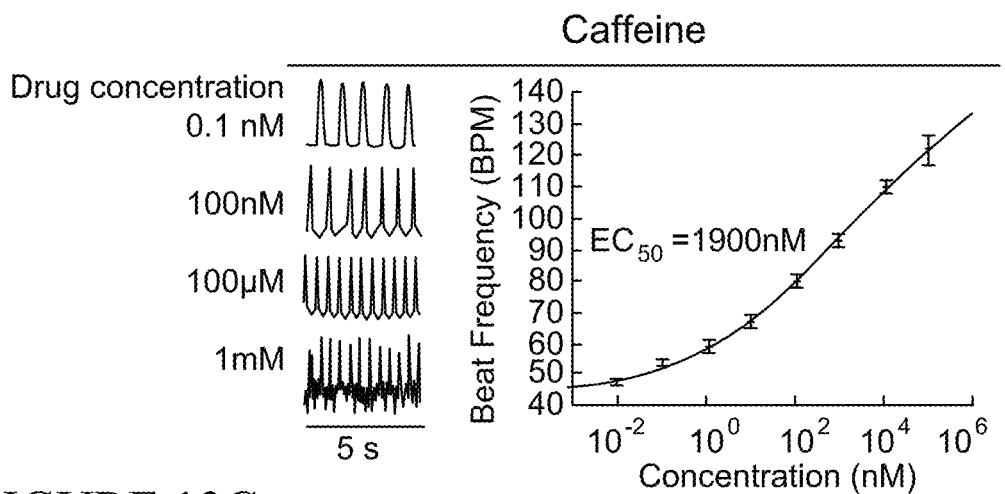
Figure 13D:
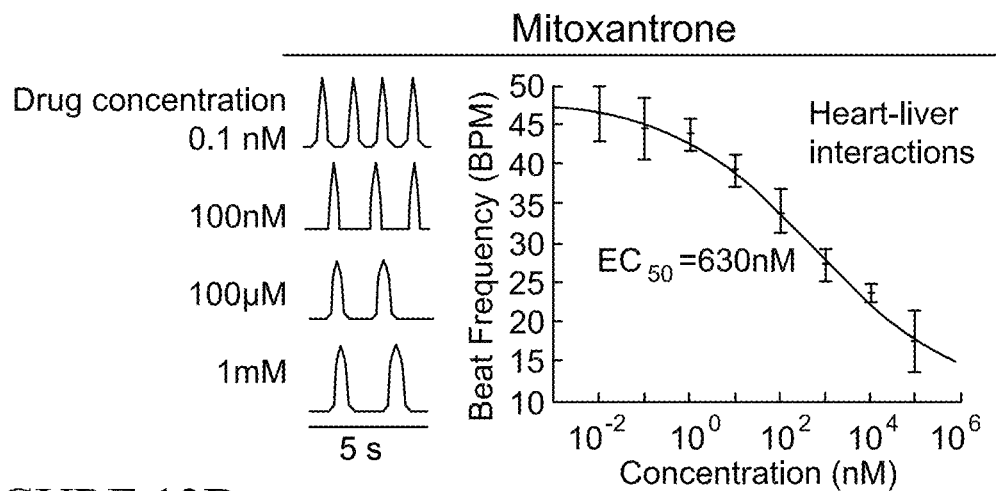
Figure 13E:
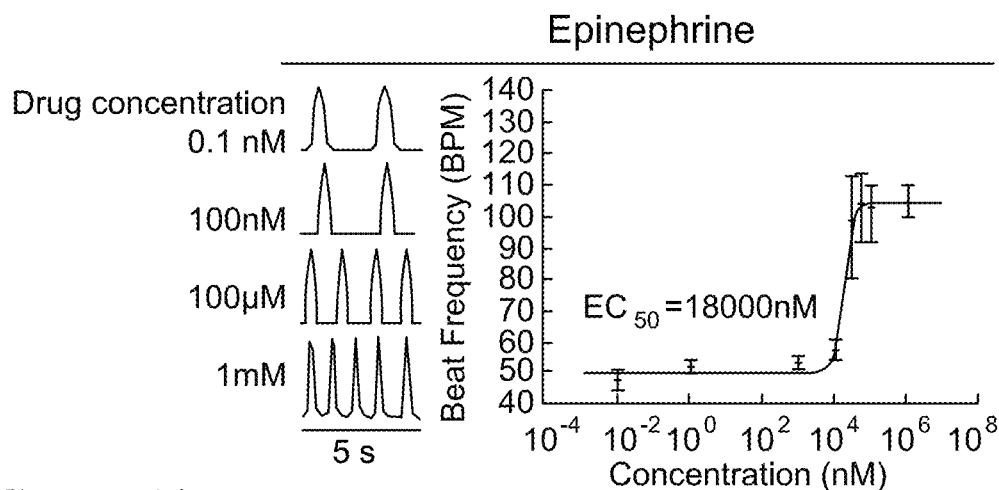
Figure 13F:
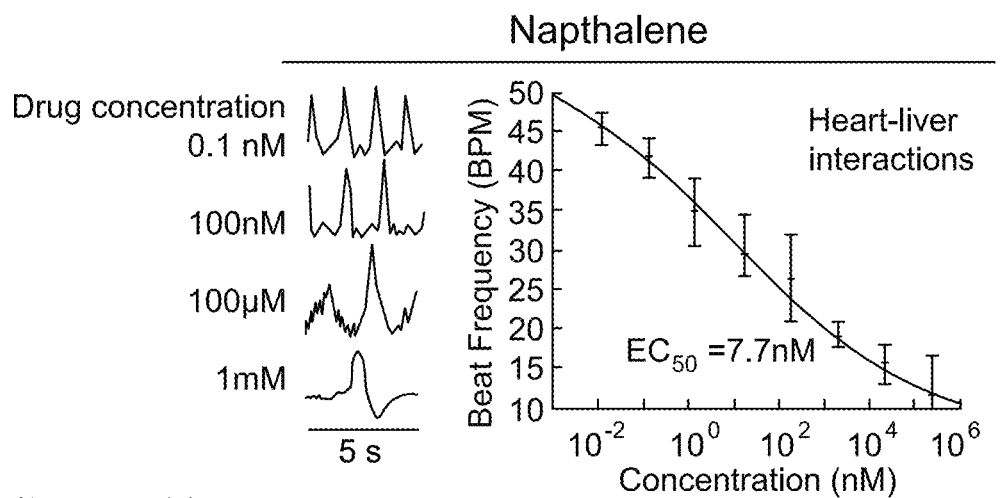

In another aspect, a predictive preclinical cardiac assay comprising the engineered cardiac tissue is provided. Referring to FIGS. 13A to 13D, predictive $EC_{50}$ values were found for various drugs: Isoproterenol, Propulsid, caffeine, and mitoxantrone. FIG. 13A depicts a graph for isoproterenol, the beat frequency (BPM) increases with increasing concentrations of isoproterenol and caffeine, and the BPM has the opposite effect by Propulsid and mitoxantrone. Accordingly, the effect of these compounds (or metabolites thereof) on adult cardiac micro-tissue can be evaluated, which provides a clinical relevance to the micro-tissues described herein that has not been available with other tissues to date.

Referring to FIG. 14, gene expression data for cardiac organoids of the described subject matter is showing adult-like contractile behavior and gene expression.

In another aspect, clinically relevant human tissue models are provided. Different cell types desired for tissue construction can be generated from the same batch of iPS cells. In some embodiments, where molecular and functional imaging and study physiological processes at multiple hierarchical levels and in real time is desired, biosensors (reporters) can be incorporated into the iPS cells to monitor specific cell phenotypes in culture (for example, distinguish between endothelial cells and cardiomyocytes), and to monitor functional readouts for tissue cells.

In accordance with one embodiment, a fibrin hydrogel containing a cell suspension, including a ratio of 75% of iPS derived cardiomyocytes and 25% of fibroblasts is injected into each well of a bioreactor and allowed to polymerize. After adding media, the tissue shrinks around the posts, which provide passive tension, ultimately forming a functional cardiac microtissue on which to perform studies or screens.

To facilitate assembly of the platform, a mechanism is provided that allows easy plug-in of input and output micro fluidic tubing to ultimately drive the perfusion within the vascular bed and connect multiple organ systems. In parallel, methods are provided to integrate the vascular perfusion approaches with the cardiac micro-tissue platform.

In another embodiment, the generation of 3D cardiac constructs from hiPS derived cells result in cardiac micro-tissues that are phenotypically matured over time is taught. The drug testing data as the measured EC50 values fall into the range of reported values from both clinical and experimental studies and further support that the matured iPS cardiac micro-tissues can serve as a predictive model of human physiology.

The disclosed subject matter further relates to dynamic anisotropic loading of cell-hydrogel constructs induced to work against force at a gradually increasing intensity enabled the formation of adult-like heart muscle. An advanced biomimetic system is provided that integrates, inter alia, three biophysical cues: (i) co-culture of hiPS-CMs with supporting cells (to enable formation of mechanically robust tissue), (ii) anisotropic alignment within a hydrogel constrained between two flexible posts (to induce auxotonic contractions), and (iii) dynamic electromechanical training with a gradual increase in intensity (to induce maturation).

In accordance with another aspect, a bioreactor platform for engineering the described micro-tissue is provided. One embodiment of the bioreactor is depicted in FIGS. 15A to 15D. The bioreactor may include a plurality of platforms for scalable control of tissue architectures. Referring back to FIGS. 15A and 15B, an exploded view of a bioreactor is used to make the 3D functional micro-tissue is shown. The bioreactor includes components for an interlocking arrangement, including a microspecific media reservoir array, such as a standard 48 or 96 well plate can be used. The bioreactor can be microtissue specific and include a microtissue specific perfusate manifold for routing of perfusate, such as for cardiac, bone, liver or skin. A microspecific support structure is included, e.g., cardiac, bone, liver and skin, a multi-perfusate routing manifold, and electrodes for cardiac tissue. The tissue reservoir array may follow standard well plate patterns and spacings, including a) top-level access to media exchange (in/out ports) for individual wells, b) two fluidic paths at different heights within each well for constant-volume/height media exchange within an open platform, c) alignment features for installing modular microtissue manifolds, d) alternate split design can accommodate carbon electrodes for electrical stimulation, and e) thin window at bottom allows imaging of microtissues.

Various reservoir approaches can be used, each having different methods of routing reservoir media, such as the bioreactor including integrated ports, integrated routing manifold, and separate ports, as shown in FIGS. 15C and 15D.

Figure 37A:
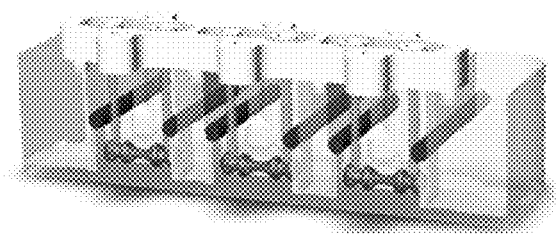
Figure 37B:
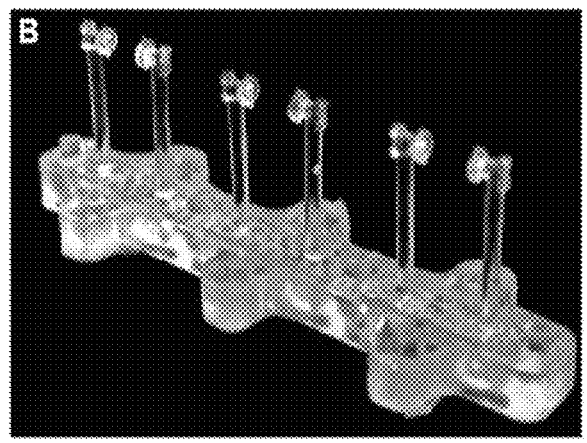
Figure 37C:
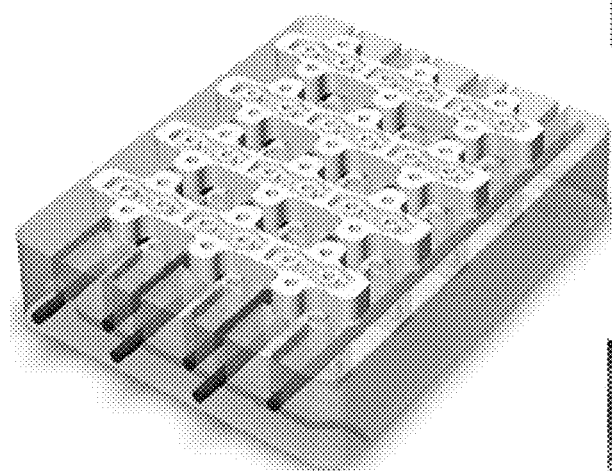
Figure 37E:
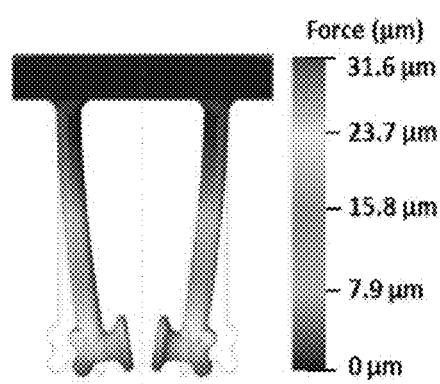
Figure 37D:
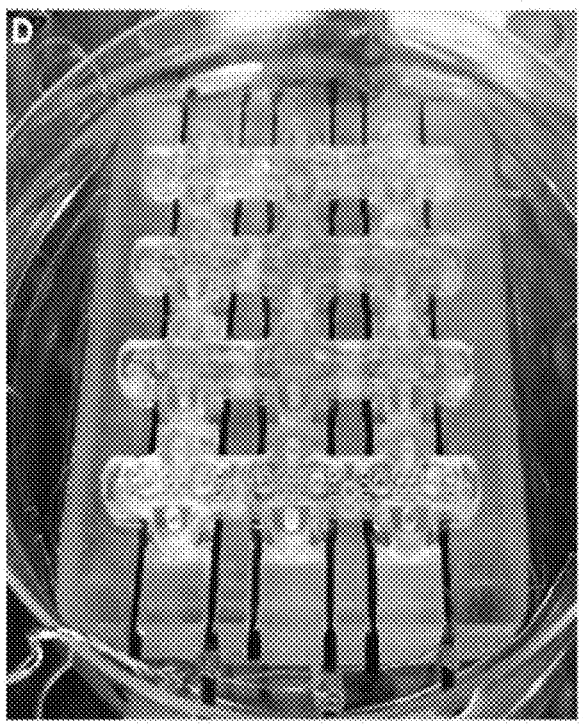
Figure 37F:
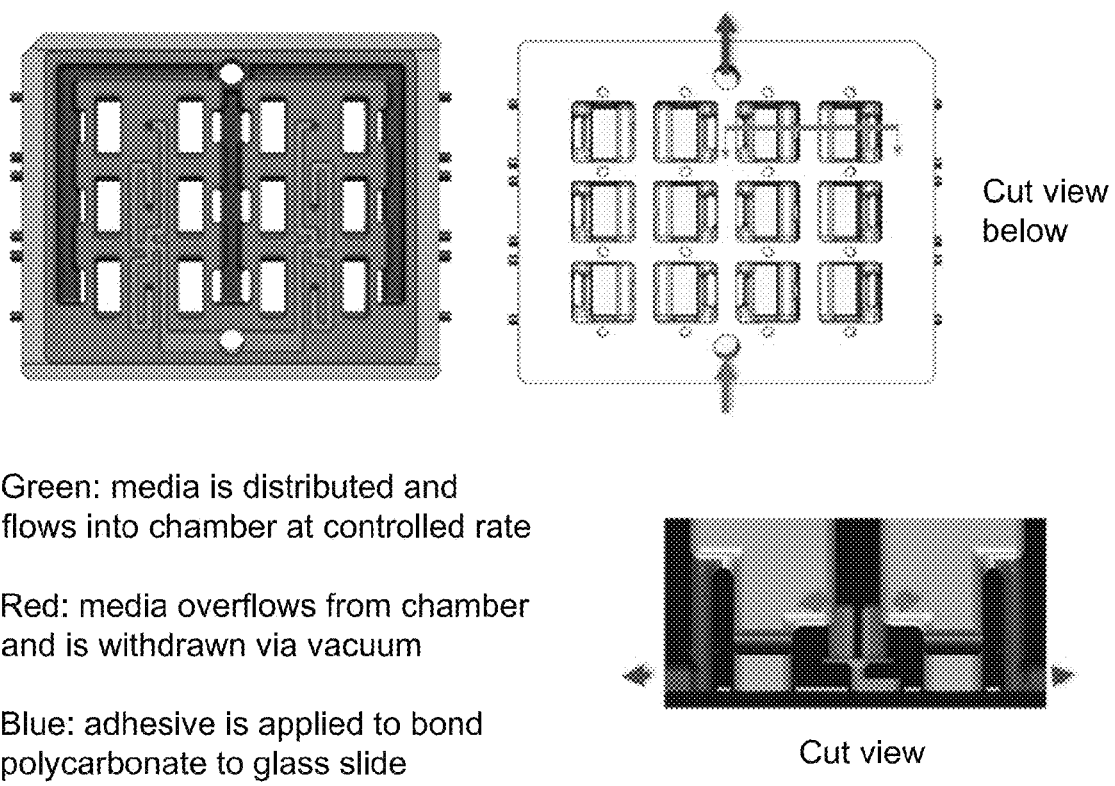

A slide (e.g., a glass slide, a transparent plastic such as polycarbonate) attached to the bottom of the bioreactor enables optical analysis, while the wells are designed to facilitate tissue formation so that the hydrogel can form around the subsequently inserted tubular members, e.g., posts/pillars. It should be noted that posts and pillars are used interchangeably. The posts are composed of flexible material, such that they can move during electromechanical conditioning. FIG. 37E shows the posts undergoing electromechanical simulation as described above. The stimulation causes the posts to oscillate therefore causing the tissue securely fasted in a fixed vertical position to stretch over time. In other words, the stimulation acts on the tissue, which bends the posts an amount commensurate with the contractile force.

Within each well there is both an inlet and an outlet to facilitate automated media exchanges. In one embodiment, this is done by extending ports into the wells. In another embodiment, a multi-well plate incorporates a flow distribution manifold to deliver media to multiple wells from a single port, and to drain media from multiple wells into a separate single port. The tubular posts are hollow and provide a passageway for the flow of a common media (a blood substitute, mimicking the role of blood connecting organs in our body) through the bioreactor. The bioreactor may be scaled-up to include, for example, 48 or 96 wells for development of the micro-tissue for scaled up screens.

Referring to FIG. 16 through FIG. 18, the components are integrated into a bioreactor. The platform is operatively engaged to a pair of opposing first and second downwardly extending posts (FIG. 16B). Each post is a hollow tubular member has a longitudinal axis that extends downwardly from the microwell platform. The hollow tubular member includes a lateral stopper along its length. The pair of opposing first and second tubular members has corresponding stoppers that facing towards each other. This post construction maintains the micro-tissue in a fixed vertical position when disposed about a pair of corresponding tubular members. Thus, the stoppers along the length of first and second hollow posts prevent migration of the tissue and allow the tissue to be in focus.

The posts typically are composed of flexible material such as, without limitation, a silicone mixture, the composition of which can be altered to change (e.g., soften, stiffen) the flexibility. Alternatively, a urethane material can be used (e.g., Hapco, Inc., AdvanSource Biomaterials). Approximate (but not limiting) dimensions of organoids are 1 mm diameter, 10 mm length, and an inner lumen of approximately 0.4 mm. The stiffness of the elastomer measured as a durometer is approximately 40 A on shore A scale.

The bioreactor platform is suitable for assembly and perfusion of cardiac micro-tissues formed from iPS C2a and for iPS hepatocytes and other iPS cells (FIGS. 16A to 16J). For example, the culture chambers have a space for the formation of cardiac micro-tissues from a suspension of iPS cardiomyocyte micro-aggregates in hydrogel. In operation, the hydrogel forms around the lattice (if incorporated), between two electrodes, and around two posts that, at the same time, provide passive tension to the micro-tissues. Stimulation causes the tissue to contract, which in turn deflects the elastic posts to which it is attached. The posts are deflected from their natural state by forces from the cardiac micro-tissues, which enables optical measurements of the force generated by the cells. The posts material composition and geometry are determined by the strain distribution in contracting cardiac organoids. The stretching of the forming tissue occurs as the hydrogel around the pillars shrinks over time, primarily due to loss of water, providing a passive stretch that leads to tension and elongation in cardiac tissues, even without electrical stimulation.

In another aspect, clinically relevant human tissue models are provided. Different cell types desired for tissue construction can be generated from the same batch of iPS cells. In some embodiments, where molecular and functional imaging and study physiological processes at multiple hierarchical levels and in real time is desired, biosensors (reporters) can be incorporated into the iPS cells to monitor specific cell phenotypes in culture (for example, distinguish between endothelial cells and cardiomyocytes), and to monitor functional readouts for tissue cells.

Culture conditions are established for routine and robust generation of endothelial cells that exhibit co-expression of cell surface markers (e.g., CD31, VE-cadherin) and functional properties (e.g., endothelial nitric oxide synthase production, tube formation) from multiple iPS cell lines with at least 10 to 40% efficiency.

The present teaching provides a general approach to rapidly construct perfusable vascular networks lined with endothelial cells and perfused with blood under high-pressure pulsatile flow. Several methods are provided to generate channel architectures within matrix scaffolds using either sacrificial filaments or created by casting. In all of these cases, seeding human endothelial cells into these channels results in the formation of well-developed endothelium that exhibits characteristics of functional endothelium. Intraluminal flows are observed at high rates relative to extraluminal flow, tight junctions are identified that are permeable to trans luminal leakage only when cells are exposed to vasoactive permeating factors. To facilitate assembly of the platform, a mechanism is provided that allows easy plug-in of input and output micro fluidic tubing to ultimately drive the perfusion within the vascular bed and connect multiple organ systems. In parallel, methods are provided to integrate the vascular perfusion approaches with the cardiac microtissue platform.

The presently described subject matter provides the generation of 3D cardiac constructs from hiPS derived cells result in cardiac microtissues that are superior to 2D models and can be phenotypically matured within the described bioreactor over time and with the application of electromechanical conditioning regimens. The drug testing data collected, as the measured EC50 values fall into the range of reported values from both clinical and experimental studies and further support that the matured iPS cardiac microtissues indeed serve as a predictive model of human physiology.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

EXAMPLES

Example 1

Materials and Methods

Cardiac Differentiation of Human iPS Cells.

Human induced pluripotent stem cells (hiPSC) were obtained from Stephen Duncan, University of Wisconsin (C2A line, #1), Bruce Conklin, Gladstone Institute (WT11 line, #2), and Masayuki Yazawa (iPS cells from a patient afflicted with Timothy Syndrome, TS line; iPS cells from a healthy family member, #3) through Material Transfer Agreements. hiPS cells were expanded on growth factor reduced Matrigel-coated plates (Corning) in mTeSR1 media (Stemcell Technologies) that was changed on a daily basis. Cells were passaged upon reaching 85-95% confluence utilizing Accutase (Life Technologies), and split at a 1:6 ratio. During the first 24 hours after passaging, 5 µM Y-27632 dihydrochloride (Tocris, 1254) was supplemented to culture medium.

Cardiac differentiation of iPS cells was initiated in confluent monolayers by replacing the mTeSR1 media with RPMI+B27-ins media, consisting of RPMI-1640 (Life Technologies), 1×B27 supplement without insulin (Life Technologies), 100 U penicillin (Life Technologies), 0.1 mg/mL streptomycin (Life Technologies), and 50 µg/mL ascorbic acid (Sigma, A4544). During the first 24 hours, the medium was further supplemented with activin A (50 ng/mL, R&D Systems) and bone morphogenetic protein 4 (BMP4, 25 ng/mL, R&D systems). From 24 hrs to 72 hrs, the RPMI+B27-ins media were supplemented with vascular endothelial growth factor (10 ng/mL VEGF, R&D systems). Beyond 72 hours, through the end of differentiation process (up to 12 days), RPMI+B27 media consisting of RPMI-1640, 1×B27 supplement with insulin (Life Technologies), 100 U penicillin, 0.1 mg/mL streptomycin, and 50 µg/mL ascorbic acid, was used and replaced every 2 days.

At day 12, the cells were characterized by flow cytometry using the cardiomyocyte-specific marker cTnT (clone 13-11, NeoMarkers). Differentiation resulted in cell populations containing 80-90% cTnT-positive cells at day 12. These cell populations were subsequently used in experiments, without selection for cardiomyocytes.

Cardiac Differentiation of Human Timothy Syndrome hiPS Cells

Timothy Syndrome hiPSCs were generated and differentiated into CMs as previously described. Briefly, fibroblasts were isolated from patients with Timothy Syndrome (TS line) and a control healthy fibroblast line (#3, IMR90 cell line) and transduced by lipofection using established episomal vectors. The resulting iPSC lines (TS line and #3) were cultured in Essential 8 (E8) medium with penicillin and streptomycin (Life Technologies, Carlsbad, Calif.) on Geltrex (Life Technologies, Carlsbad, Calif.)—coated plates or dishes (Corning Enterprises, Corning, N.Y.). hiPSC-CMs were generated in monolayer cultures by switching to DF20 (with supplemental glucose to 4.5 g/L) on days 1-4 with application of CHIR99021 (CHIR, GSK3 inhibitor, #1386, Lot #6 and #7, Axon MedChem) and BIO (GSK3 inhibitor IX, #361550, Lot #D00148116, Calbiochem) between days 2-3. 2 µM IWP-3 (Wnt inhibitor, #SML0533, Lot #102m4613V, Sigma-Aldrich) was added for days 5-11, in DF20 for days 5-7 and DF5 for day 7 onwards. Spontaneous beating was observed on day 11, and the cells were used in experiments on day 12.

Human Fetal Cardiac Tissues

Fetal hearts were purchased as surgical waste from Advanced Bioscience Resources (Alameda, Calif.). Following surgery, fetal hearts were delivered on ice within 2.5 hours. Left ventricles were sectioned from the apex towards the atria into 7 mm long×2 mm wide strips, washed 3 times in Hanks Balanced Salt Solution (Gibco), and then transferred to low attachment 6-well plates (NUNC) containing RPMI+B27 media and placed into the incubator for 1 hour before the measurements. The strips of FCT were analyzed in a similar manner to the ORGANOIDs for contractile behavior, force generation, gene expression, cardiac proteins, ultrastructure and histomorphology, as detailed below.

Micro-Tissue Platform

The platform was assembled from two separate components: the wells for tissue culture, and an array of support structures with integrated elastomeric pillars for tissue attachment. Both components were fabricated out of polycarbonate (PC) utilizing a Computer Numerical Control (CNC) milling machine and with mating features for stability and repeatable positioning.

The pillars were designed to subject the cell-hydrogel construct to mechanical loading designed to mimic that in the native heart muscle. Hydrogel compaction caused passive tension in the cell-hydrogel constructs as they were stretched between the two pillars, inducing anisotropic elongation and alignment. Synchronous contractions induced by electrical stimulation generated dynamic forces in the contracting tissue constructs that were forced to work against the pillars.

The pillars were formed by centrifugal casting of polydimethylsiloxane (PDMS, Dow Corning Sylgard 184), through and extending from the PC support structures. The supports were first inserted into Delrin (polyoxymethylene) molds fabricated by CNC machining and PDMS (10:1 ratio PDMS to curing agent) was centrifugally cast at 400 RCF for 5 minutes and cured in an oven at 60° C. for one hour. The resulting component consisted of three pairs of pillars to support the formation of three tissues. Pillars were 1 mm in diameter, 9 mm in length, and spaced 6 mm center-to-center.

The platform contained 12 wells for tissue culture that were patterned with the exact 48-well plate spacing, such that the platform corresponded to one quarter of the 48-well plate. Each well had a bottom portion measuring 10×4×4 mm where the hydrogel for the formation of tissues was introduced, and a wider top portion measuring 10×7×4 mm for culture media. A glass slide was bonded to the bottom of the platform to allow for facile microscopic observation of the tissue.

Electrical stimulation of the cell-hydrogel tissue constructs was provided via carbon rods (Ladd Research Industries) that served as electrodes. The carbon rods were placed into slots machined on either side of the culture well so that the electrodes were in parallel and positioned normal to the long axis of both the culture well and the tissue construct. The electrodes were connected to a cardiac stimulator (Grass s88x) via platinum wires (Ladd Research Industries). Electrical stimulation was generated in a spatially uniform, pulsatile electrical field (4.5 mV intensity, 2 ms in duration, monophasic square waveform), in the direction perpendicular to the long axis of the ORGANOID. The parameter settings (amplitude, duration, frequency, and waveform) were controlled by the Grass s88x cardiac stimulator.

Culture of Bioengineered Cardiac Organoids

The differentiated hiPS-CMs were combined with supporting human dermal fibroblasts (Lonza), at a ratio of 75% iPS-CMs and 25% fibroblasts, in Dulbecco's Modified Eagle Medium supplemented with 10% v/v fetal bovine serum, 100 U penicillin, and 0.1 mg/mL streptomycin, at a final concentration of 5M cells/mL. The cells were encapsulated into the fibrin hydrogel by mixing 20 mg/mL human fibrinogen (Sigma), 100 U/mL human thrombin (Sigma), and cell suspension at a 3:1:1 ratio.

The hydrogel solution (200 μL containing 1 million cells) was injected into each well of the platform and allowed to polymerize at 37° C. for 30 minutes, so that the organoids were formed around the pillars. Then, 800 μL of RPMI+B27 media containing 0.2 mg/mL aprotinin (Sigma, A3428) was added into each well. Subsequent media changes occurred every other day and consisted of 800 μL of RPMI+B27 media containing 0.2 mg/mL aprotinin (Sigma, A3428) for the first 7 days, and 800 μL of RPMI+B27 media for the remainder of culture time (either day 7-28 or day 7-84).

Electrical stimulation was initiated on day 7, according to one of three training regimens: "control" (no electrical stimulation, 0 Hz), "constant training" (constant stimulation at 2 Hz), and "intensity training" (a ramped stimulation protocol that increases in intensity 0.33 Hz daily from 2 Hz at Day 7 to 6 Hz at Day 19).

In most experiments, tissues were cultured for a period of 4 weeks, and in some experiments for up to 3 months. Data reported herein have been generated in 16 independent experiments using cells from 4 separate lines of iPS cells, and the following total numbers of organoids used as detailed in Table 1. Tissue properties were evaluated using real time assessment of: amplitude and frequency of contractions, calcium handling, force generation, excitation threshold, and maximum capture rate. In addition, real time data were generated form tissue responses to an array of chonotropic, ionotropic and cardiotoxic drugs. The following drugs and concentration ranges were used as detailed in Table 2. The corresponding endpoint assays were conducted to determine cell and tissue morphology (histologically), ultrastructure (by transmission electron microscopy), gene expression (real-time PCR), and the presence and distribution of cardiac proteins (immunohistochemistry).

Contractility Analysis

Tissue contractility was measured by tracking the change in the projected tissue area as a function of time. Live cell, bright field videos were acquired at rates of 150 frames per second using a Pike F-032b (Allied Vision Technologies) camera controlled with the custom SPLASSH software. Acquired video frames were inverted and an automated intensity threshold was used to identify cell location in the video frame.

First, a baseline time point in the video corresponding to a relaxed tissue state was selected. Absolute differences in cell area from the baseline frame were then calculated to create a time course of cell area dynamics as a function of time. The resulting time courses were analyzed with a native MATLAB automated peak finding algorithm to determine locations of maximum cell contraction indicated by the locations of local maxima in the time courses.

Beat period lengths were determined from the length of time between pairs of local maxima. Beat frequencies were determined by inverting beat periods. Contraction amplitude relaxation times were measured from the length of time required for the time course to relax in amplitude from the peak contraction amplitude of the local maxima to the calculated relaxation amplitude (e.g. the R90 time was the length of time elapsed from the local maxima until the contraction time course reached 10% of the local maximum contraction difference amplitude).

Calcium Handling

Tissues (organoids and FCTs) within culture platforms were loaded with Fluo-4 NW (50% v/v, Life Technologies) in RPMI+B27 media containing 5 μM blebbistatin (Sigma) to reduce movement artifacts, for 30 minutes at 37° C. Videos were acquired at a rate of 150 frames per second using a Pike F-032 camera (Allied Vision Technologies) controlled by the custom designed, free-source SPLASSH software. Videos were analyzed in MATLAB using a custom script that calculated the temporal changes in calcium fluorescence intensity. Specifically, each frame was normalized to a baseline background region to give baseline-corrected changes in minimum and maximum fluorescence values for each frame. This temporal change in fluorescence intensity was presented as a calcium transient trace from which measurements were obtained.

Calcium transients were analyzed to measure the irregularity of various parameters as previously described. Briefly, the calcium transient "timing" was determined as the peak-to peak value of two successive beats as defined by the peak maxima. Calcium transient "amplitude" was determined by numerically integrating the area below the peak maxima relative to the baseline. Calcium transient traces were analyzed during 5 mM caffeine stimulation of tissue constructs previously treated with either 1 mM verapamil (Sigma) or 0.002 mM thapsigargin (Sigma). Quantitative measurements of the caffeine response were obtained by comparing the calcium transient amplitude before and after the addition of 5 mM caffeine (Sigma). The average rhythmicity was defined as the ratio of the parameter standard deviation to the parameter mean of the corresponding (control, constant, intensity) tissue group. Beats with parameter measurements falling outside two standard deviations from the average rhythmicity were classified as irregular.

Force Measurements

Tissues (organoids and FCTs) were transferred to a commercial organ bath system (DMT Myograph) containing oxygenated modified Tyrode's solution (129 mM NaCl, 5 mM KCl, 2 mM CaCl2, 1 mM MgCl2, 30 mM Glucose, 25 mM HEPES, (pH 7.4 with NaOH) supplemented with 2% B27 and maintained at a constant temperature of 37° C. without electrical stimulation. All data were obtained using LabChart software (ADInstruments). The tissues were allowed to equilibrate for 15 minutes without electrical stimulation and the spontaneous beating measurements were recorded. The tissues were then allowed to equilibrate for 15 minutes under electrical stimulation (1 Hz, 5 ms, 80-100 mA, rectangular pulses) in order to preload the tissues by manual stepwise adjustment of the tissue length to that of the maximal force generated, which assumes the optimal sarcomere length is attained.

Twitch tension measurements were obtained by increasing the organ bath $[Ca^{2+}]$ concentration from 0.2 to 2.8 mmol/L, by changing the concentration of $CaCl_2$ used in the Tyrode's solution. The tissues were subjected to electrical stimulation for 3 minutes, and an average of 10 contractions were measured. The stimulation was then discontinued for 10, 20, or 30 seconds, and the tissues were allowed to recover for 2 minutes. Post-rest potentiation measurements were obtained by analyzing the change in twitch tension from the first beat upon re-initiation of electrical stimulus.

Contractility and twitch parameters were further investigated in response to changes in tissue construct length (Frank-Starling response) and to the increasing electrical stimulation. Twitch forces were calculated as the average of the difference between maximum and minimum cyclic force. Force-length relationships to determine the Frank-Starling relationship were determined by incrementally increasing the distance between pillars in the organ bath, and then allowing the tissue to recover before the force measurement was made. The Frank-Starling responses were recorded by increasing the length of the tissue in step-wise increments until increases in length no longer elicited increases in force generation. The force-frequency relationship (FFR) was measured by increasing the electrical stimulation frequency from 1 Hz to 6 Hz, in 1 Hz intervals and statistically analyzed to evaluate the changes in response normalized to the 1 Hz baseline frequency. The tissues were exposed to each stimulation frequency for 30 seconds and allowed to rest for 60 seconds before increasing the stimulation frequency to the next level.

Excitation Threshold and Maximum Capture Rate

To determine the ET, tissues were paced at 2 Hz at a gradually increasing field strength (up to 25 mV) until the tissue was observed under bright field microscopy to beat macroscopically and in sync with the pacing stimulus. To determine the MCR, tissues were paced at 2 Hz at the field strength twice the ET, and the rate was gradually increased in 0.1 Hz increments up to a maximum of 10 Hz, until the tissue stopped responding to the pacing stimulus. We determined that the tissues were capturing at the stimulation frequency by analyzing videos acquired during stimulation, and confirming that the beat frequency of the tissue construct corresponded to the stimulation frequency.

Immunofluorescent Staining

For morphological analysis, tissues (organoids and FCTs) were fixed by using gradually increasing concentrations of paraformaldehyde (1, 2, 3 and 4%) for 1 hour each. FCTs were immediately used in immunostaining protocols, while organoids were paraffin embedded and sectioned at 5 µm thick. The tissues were quenched in 0.5 M NH4Cl for 30 minutes, permeabilized with 0.2% Triton X-100 in PBS for 15 minutes, and incubated in blocking solution (1% bovine serum albumin [BSA], 2% goat serum in PBS) for 2 hours.

The following primary antibodies were incubated for 2 hours in 1% BSA: anti-α-actinin (1:200, Abcam, ab9465), anti-cardiac troponin T (1:100, Thermo Scientific; MS-295-P1), antiryanodine (1:100, abcam, ab2827), anti-Bin1 (1:100, Abcam, ab137459).

Tissues were washed 3 times in 0.2% Triton X-100 for 5 minutes and incubated with the corresponding secondary antibodies for 2 hours: anti-mouse—Alexa Fluor 488 (1:400, Invitrogen, A21202), anti-rabbit—Alexa Fluor 568 (1:400, Invitrogen, 81-6114), anti-mouse Alexa Fluor 635 (1:400, Invitrogen, A31574). The tissues were washed and subsequently incubated with NucBlue (Molecular Probes, R37606) for nuclei counterstaining. The immunostained tissues were visualized using a confocal microscope (Olympus Fluoview FV1000).

For T-tubule immunostaining, the tissues were incubated with Wheat Germ Agglutinin fluorescently conjugated to Alexa Fluor 488 (Life Technologies, W11261) or Di-8-ANEPPS (Life Technologies, D-3167) for 20 minutes before permeabilization and subsequent staining with the antibodies listed above.

Transmission Electron Microscopy

Tissues (organoids and FCTs) were fixed with 2.5% glutaraldehyde in 0.1 M Sorenson's buffer (pH 7.2) for 1 hour and sent to the Electron Microscopy and Histology (EM&H) Core Facility at Weill Cornell Medical College for sample preparation, imaging, and data analysis in a blinded fashion. Samples were post-fixed for an additional hour with 1% $OsO_4$ in Sorenson's buffer, dehydrated, embedded, sectioned, stained with Toluidine Blue, and examined under a JEM-1400 electron microscope.

Sarcomere Length

Sarcomere length was determined by measuring the distance between intensity peaks along the long axis of designated cell areas containing clear striations, in images of tissues (organoids and FCTs) immunoflourescently stained with α-actinin. A minimum of 3 sarcomere lengths per cell were obtained.

Fractional Shortening

The fractional shortening was measured within the tissues as the decrease in CM length, as the CM transitions from a relaxed state to a contracted state, and expressed as a percent of the CM length in the relaxed state. The measurements were done using a custom MATLAB code that utilizes video edge-detection based on the contrast between the tissue sample (dark) and the surrounding area (light).

Cell Morphology

Cells were enzymatically digested using serial digestions of collagenases type 1 and 2 (Worthington), and plated onto 8 well chamber slides (Lab-Tek, Sigma-Aldrich). The cells were allowed to attach for 72 hrs and imaged using phase contrast microscopy. Cell area was quantified from these images using the "% Area" function in Image J software after thresholding for the cells within each image. Cell aspect ratio was calculated from these images using the "Roundness" function in Image J where the final aspect ratio is obtained through the equation: 1−Roundness, with 0 corresponding to a perfect circle and 1 corresponding to a completely elongated object.

Quantitative PCR

Total RNA was purified from the tissues according to the manufacturer's instructions using TRIzol (Life Technologies). Reverse transcription was achieved using Ready-To-Go You-Prime First-Strand Beads (GE Healthcare, 27-9264-01), according to the manufacturer's instructions. Genes were quantified by real-time PCR using SYBR Green primers (Life Technologies) and was carried out on Applied Biosystems Step One Plus. The integrity of the primers used were confirmed and are listed in Table 3. Data analysis was carried out using the ΔΔCt method for samples normalized to glyceraldehyde-3-phosphate dehydrogenase (GAPDH) gene expression.

Dose Response Curves

Drugs were diluted in standard media (RPMI+B27). Successively higher doses of each drug were administered at concentrations of $10^{-11}$M to $10^{-5}$M, in decigram increments. Tissue videos were captured ≥5 minutes after each dose was administered, and processed using custom image processing software as discussed above. For chronotropic drugs, bright field videos were taken at each drug concentration so that measurements of the beat frequency could be determined as a function of drug concentration. For ionotropic drugs, tissues were placed in the organ bath and force measurements were recorded as previously described at each drug concentration so that the measurements of the change in force generated could be determined as a function of drug concentration. Dose-response curves for these parameters could be constructed by using Matlab to fit the Hill Equation for sigmoid curves to the data, to determine the corresponding $EC_{50}$ value.

Statistics

Statistical analysis was performed using custom MATLAB functions. Differences between experimental groups were analyzed using two-way ANOVA. Post-hoc pairwise analysis was done using Tukey's Honest Significant Difference. P<0.05 was considered significant for all statistical tests.

Computer Vision

Video data from a variety of drug response experiments were analyzed using image processing software, including those taken using brightfield imaging and calcium imaging as discussed above. These videos were analyzed through a variety of means. Commonly, time courses were created from these videos using a combination of methods: pixel-by-pixel differences compared to a reference frame (as described in contractility analysis above), frame-by-frame brightness differences compared to a reference frame (as described in calcium handling above), strain/motion mapping through the use of image registration techniques and/or optical flow (performed on brightfield videos), force traces through the application of strain/motion mapping techniques to the PDMS pillars, etc. Features were then extracted from these time courses (as well as the raw videos for parameters such as conduction velocity or spiral wave detection) to create a vector of values parameterizing each video. These vectors described the state of the tissue at the time of the video, and were then linked to labels of interest for that video, such as drug type, concentration, in vivo arrhythmogenicity, etc. This feature space was then analyzed using machine learning algorithms (SVMs, decision trees, etc.) to build regressors and classifiers on the relevant labels. The algorithms and data preprocessing were optimized using cross-validation techniques.

TABLE 1

Overview of the number of organoids used within experiments

| | | |
|---|---|---|
| Line #1 (C2A): n = 23 (control) | n = 19 (constant training) | n = 34 (intensity training) |
| Line #2 (WTC11): n = 15 (control) | n = 12 (constant training) | n = 13 (intensity training) |
| Line #3 (IMR90): n = 15 (control) | n = 16 (constant training) | n = 10 (intensity training) |
| Line #4 (TS): n = 12 (control) | n = 13 (constant training) | n = 12 (intensity training) |

TABLE 2

Overview of drugs used within experiments

| Drug | Drug Mechanism | Concentrations used |
|---|---|---|
| Ivadrabrine | Block If pacemaker channel | 3 μM |
| SEA0400 | Block NCX | 2 μM |
| Ryanodine | Block calcium mediated calcium release | 1 μM |
| Caffeine | Opens sarcoplasmic reticulum RyR2 channels | 5 mM, $10^{-11}$ M-$10^{-5}$ M |
| Verapamil | Block L-type Ca channels | 1 mM |
| Thapsigargin | Block SERCA | 0.002 mM |
| Nifedipine | Block L-type Ca channels | 10 nM-10 μM |
| Isoproterenol | b-adrenergic agonist, similar to adrenaline | 10−11 M-10−5 M |
| Epinephrine | b-adrenergic agonist, similar to adrenaline | 10−11 M-10−5 M |
| Propranolol | Nonselective beta blocker | 10−11 M-10−5 M |
| E4031 | Block hERG channel | 10−11 M-10−5 M |
| Cisapride | Block hERG channel | 10−11 M-10−5 M |
| CaCl2 | Elicit calcium induced calcium response | 0.2-2.8 mM |

TABLE 3

Oligonucleotide sequences used for real-time quantitative PCR experiments.

| Gene | Forward 5'-3' | Reverse 5'-3' | SEQ ID NO |
|---|---|---|---|
| cTnT | ACAGAGCGGAAAAGTGGGAAG | TCGTTGATCCTGTTTCGGAGA | 1, 2 |
| Cx43 | GGTGACTGGAGCGCCTTAG | GCGCACATGAGAGATTGGGA | 3, 4 |
| MYH6 | GATAGAGAGACTCCTGCGGC | CCGTCTTCCCATTCTCGGTT | 5, 6 |
| MYH7 | TCGTGCCTGATGACAAACAGGAGT | ATACTCGGTCTCGGCAGTGACTTT | 7, 8 |
| MYL2 | TTGGGCGAGTGAACGTGAAAA | CCGAACGTAATCAGCCTTCAG | 9, 10 |
| MYL7 | GCCCAACGTGGTTCTTCCAA | CTCCTCCTCTGGGACACTC | 11, 12 |
| AKAP6 | AGTTCTCCCTAAAGCTGCTGT | TCTGCCTAGTGTAGTTGCCATT | 13, 14 |
| GJA5 | AGAGTGTGAAGAAGCCCACG | AACAGATGCCAAAACTTCTGCT | 15, 16 |
| JPH2 | ACTCTGGCTCCTGGAACTTTG | GCGCCCCTTGGTCTCTATG | 17, 18 |
| SLC8A1 | TCATAGCTGATCGGTTCATGTCC | CAGTTGTCTTGGTGGTCTCTC | 19, 20 |
| ATP2A2 | CATCAAGCACACTGATCCCGT | CCACTCCCATAGCTTTCCCAG | 21, 22 |
| CACNA1C | TGATTCCAACGCCACCAATTC | GAGGAGTCCATAGGCGATTACT | 23, 24 |
| RYR2 | CATCGAACACTCCTCTACGGA | GGACACGCTAACTAAGATGAGGT | 25, 26 |
| CASQ2 | CATTGCCATCCCCAACAAACC | AGAGTGGGTCTTTGGTGTTCC | 27, 28 |
| PLN | ACCTCACTCGCTCAGCTATAA | CATCACGATGATACAGATCAGCA | 29, 30 |
| CAMK2B | GCACACCAGGCTACCTGTC | CATACGCCTCTTTGCGAAGG | 31, 32 |
| TRDN | TCACAGAAGACATAGTGACGACG | TGGCAATAGAGCTTGCTGAAA | 33, 34 |
| CAV3 | GACCCCAAGAACATTAACGAGG | GGACAACAGACGGTAGCACC | 35, 36 |
| BIN1 | ATGAGGCAAACAAGATCGCAG | CGTGACTTGATGTCGGGGAA | 37, 38 |
| AMP2 | TGAGCAGTGCGTCCAGAATTT | CGATCTTGTTTGCCTCATCCC | 39, 40 |
| SCN5A | AGCTGGCTGATGTGATGGTC | CACTTGTGCCTTAGGTTGCC | 41, 42 |
| KIR2.1 | GTGCGAACCAACCGCTACA | CCAGCGAATGTCCACACAC | 43, 44 |
| ITPR3 | CCAAGCAGACTAAGCAGGACA | ACACTGCCATACTTCACGACA | 45, 46 |
| HCN2 | AGAAGGGCATTGACTCCGAG | TAGCGGATCAGGCGTGAGA | 47, 48 |
| SCN1B | TCCTGCGCTATGAGAATGAGG | TGGTGTTGTGCTCGTAGTTTTC | 49, 50 |
| HCN1 | CATGCCACCGCTTTAATCCAG | ATTGTAGCCACCAGTTTCCGA | 51, 52 |
| KCNJ8 | GTGATTGCCGTCCGAAATGG | AGTTGGTGAATAGGAACCACCT | 53, 54 |
| KCNH2 | CAACCTGGGCGACCAGATAG | GGTGTTGGGAGAGACGTTGC | 55, 56 |
| PRKAA1 | TTGAAACCTGAAAATGTCCTGCT | GGTGAGCCACAACTTGTTCTT | 57, 58 |
| TFAM | ATGGCGTTTCTCCGAAGCAT | TCCGCCCTATAAGCATCTTGA | 59, 60 |
| PPARGC1A | GCTTTCTGGGTGGACTCAAGT | GAGGGCAATCCGTCTTCATCC | 61, 62 |
| PPA1 | CCCTGGAGTACCGAGTCTTCC | CATTTTTGCATTAGACCAGCGTG | 63, 64 |
| PPP2R4 | TCTCAGGCATACGCTGACTAC | GGAGACTCTGTACTCGAAGGT | 65, 66 |
| SLC2A4 | ATCCTTGGACGATTCCTCATTGG | CAGGTGAGTGGGAGCAATCT | 67, 68 |
| NKX2.5 | CCAAGGACCCTAGAGCCGAA | ATAGGCGGGGTAGGCGTTAT | 69, 70 |
| NPPA | CAACGCAGACCTGATGGATTT | AGCCCCCGCTTCTTCATTC | 71, 72 |
| NPPB | TGGAAACGTCCGGGTTACAG | CTGATCCGGTCCATCTTCCT | 73, 74 |

TABLE 3-continued

Oligonucleotide sequences used for real-time quantitative PCR experiments.

| Gene | Forward 5'-3' | Reverse 5'-3' | SEQ ID NO |
|---|---|---|---|
| PRKCA | TGGACTTATCCATCAAGGGATGA | AGTGTGATCCATTCCGCAGAG | 75, 76 |
| MAPK1 | TCTGGAGCAGTATTACGACCC | CTGGCTGGAATCTAGCAGTCT | 77, 78 |
| SIRT1 | TAGCCTTGTCAGATAAGGAAGGA | ACAGCTTCACAGTCAACTTTGT | 79, 80 |
| PRKACA | CAAGGAGACCGGGAACCACTA | CATTCAGGGTGTGTTCGATCTG | 81, 82 |

Example 2

Results

Organoids were formed using hiPS-CMs derived from three healthy human donors (FIG. 19A, FIG. 19B) by encapsulating cells in fibrin hydrogel (200 μL; 1M cells; 75% hiPS-CMs/25% human fibroblasts) in the wells of a micro-tissue platform (FIG. 20A, FIG. 21A-E; FIG. 37). To promote tissue maturation, 4 weeks of electromechanical conditioning, where electrical signals (4.5 mV, 2 ms duration, monophasic square waveform) was applied, and which forced the tissues to pull the posts as they contracted. Three different training regimens were studied: control (no stimulation, 0 Hz), constant frequency stimulation (constant training: 2 Hz, day 7-day 28), and interval intensity stimulation (intensity training: 2 Hz on day 7 increased by 0.33 Hz each day to a maximum of 6 Hz from day 19 to day 28) (FIG. 21F, FIG. 21G). Engineered organoids were benchmarked against strips of 18-19 week old human fetal cardiac tissue (FCT) from left heart ventricles. After confirming the development of an adult-liked phenotype, organoids were studied for their responses to a range of drugs and their ability to recapitulate the phenotype of an inherited cardiomyopathy using patient-specific iPS-CMs.

Organoid maturation was evidenced by increasingly regular contraction profiles (FIG. 20B, FIG. 25 A). During the 4-weeks of training, organoids acquired increasingly regular contraction profiles at frequencies determined by each of the 3 regimens (FIG. 20B, 25A). Following the 4-week training regimen through at least 12 weeks, ORGANOIDs gradually assumed a physiological beating frequency of 1 Hz, as during the transition from the fetal to adult cardiac phenotype, and maintained it for up to 3 months of in vitro culture (FIG. 20B). In the absence of electrical stimulation, organoid contractility may become controlled by an internal $Ca^{2+}$ clock, physiologically entrained by the training regime, and initiated via calcium-induced calcium release (FIGS. 27A-27C). By constantly increasing the stimulation rate, the ORGANOIDs responded by frequency-dependent acceleration of relaxation (FDAR, FIGS. 30G-30I), an intrinsic property of adult myocardium. Accordingly, contraction time, beat-to-beat variability and relaxation time were all lower in organoids than in other organoids or FCTs, decreasing as a function of time and training intensity (FIGS. 25B-25E).

Figure 20D:
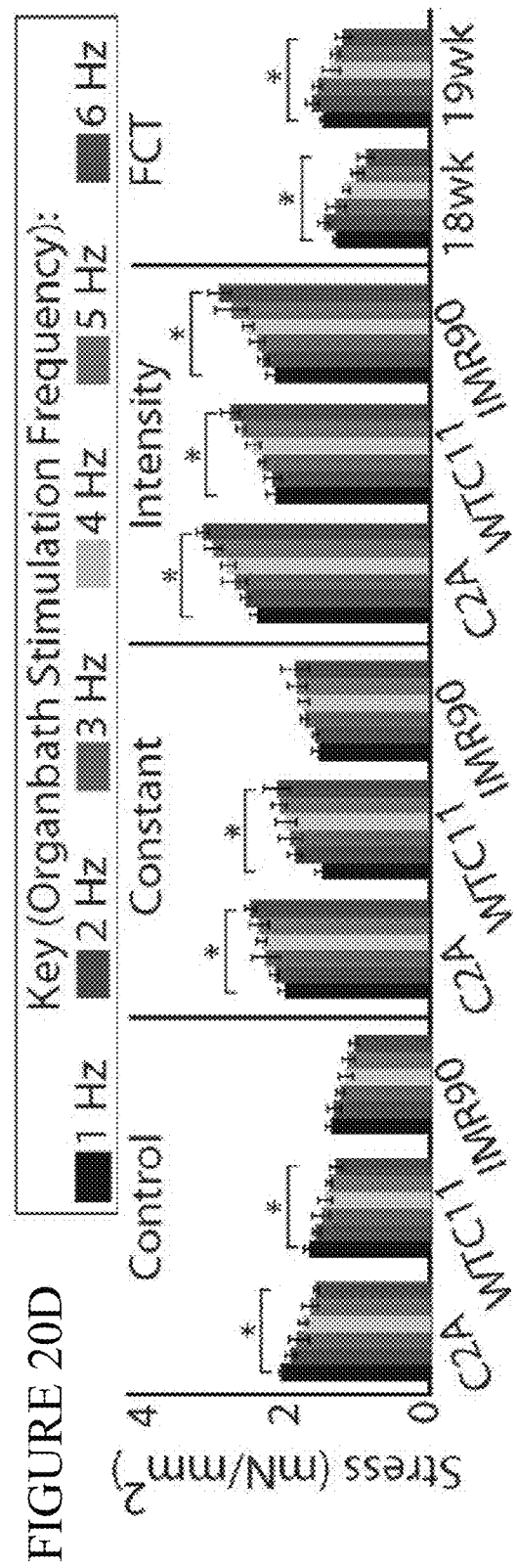
Figure 20E:
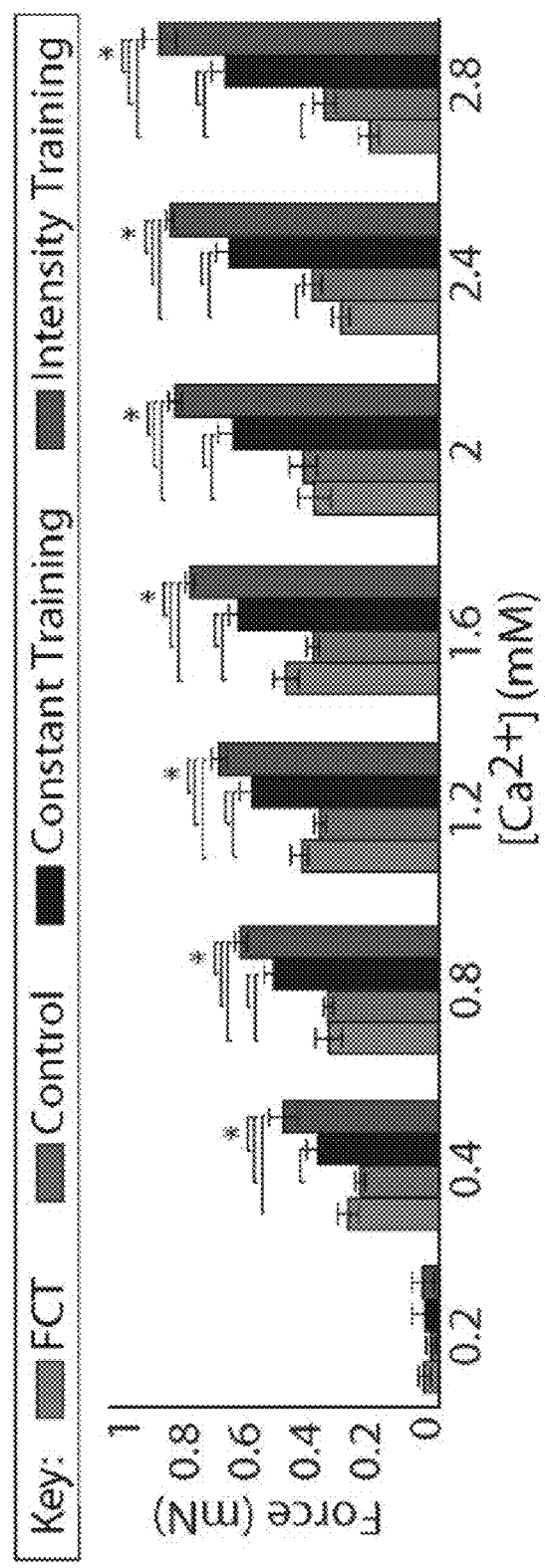
Figure 21G:
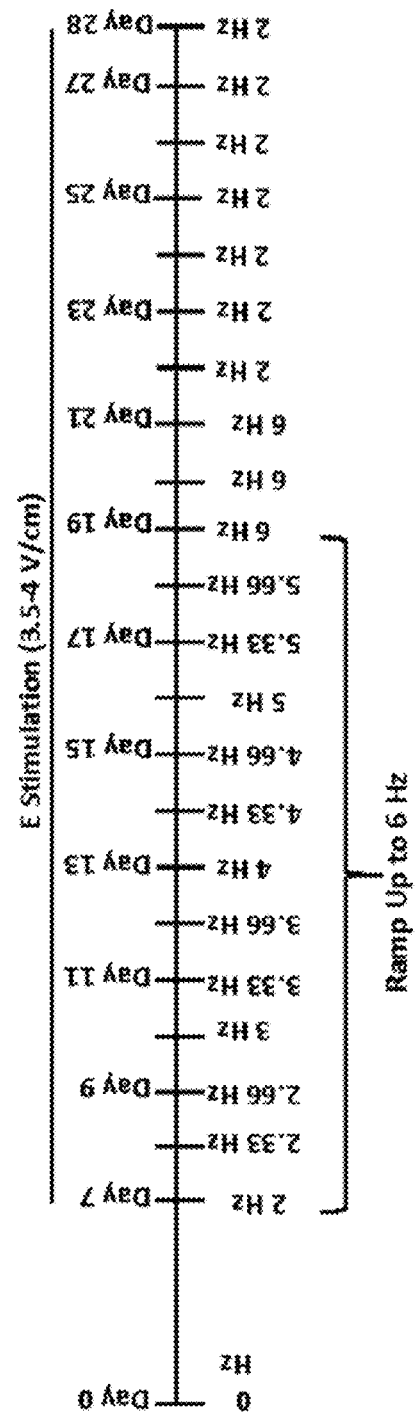
Figure 25A:
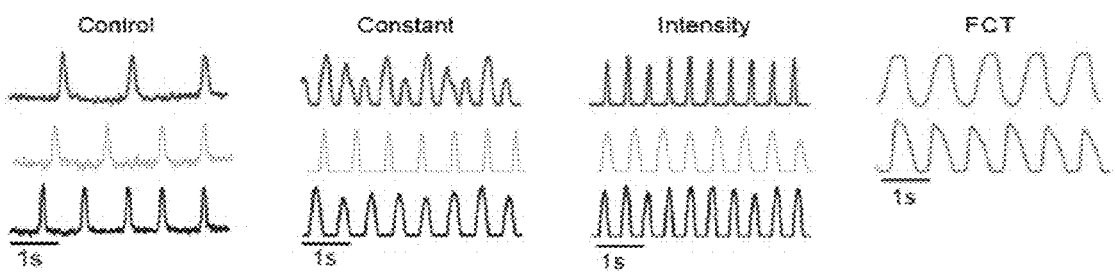
Figure 25B:
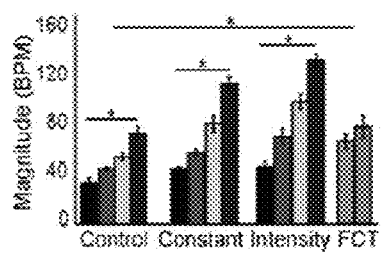
Figure 25C:
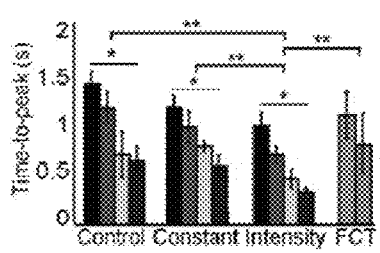
Figure 25D:
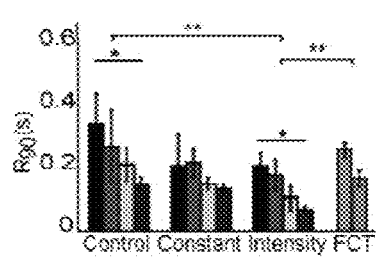
Figure 25E:
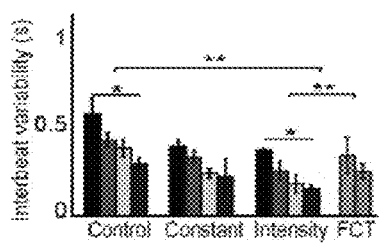
Figure 25F:
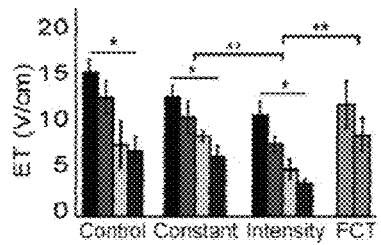
Figure 25G:
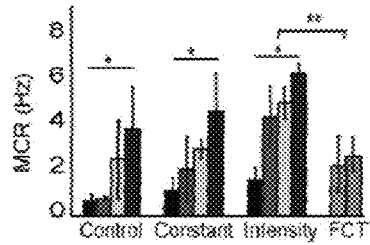
Figure 25H:
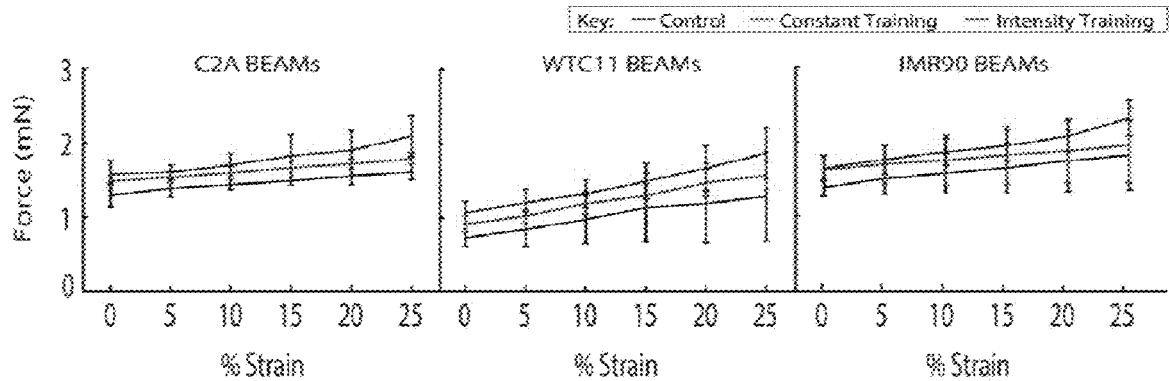
Figures 26A, 26B:
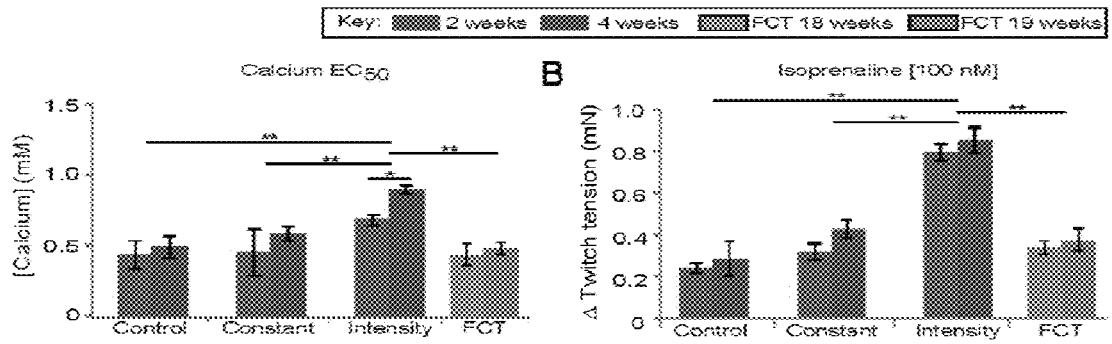
Figure 26C:
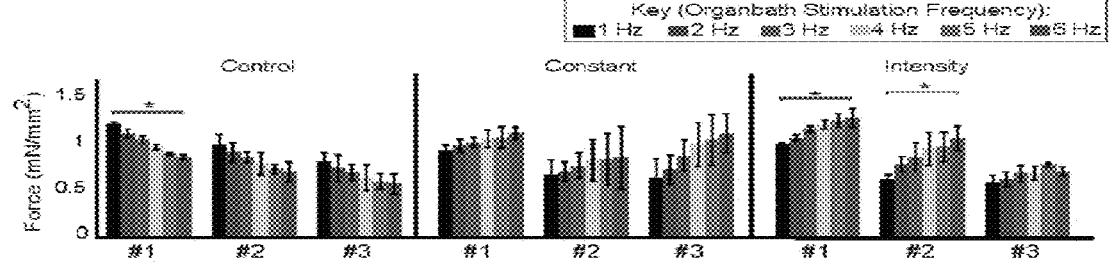
Figure 30A:
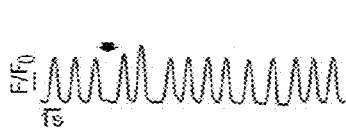
Figure 30B:
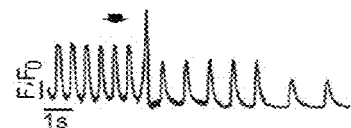
Figure 30C:
Figure 30D:
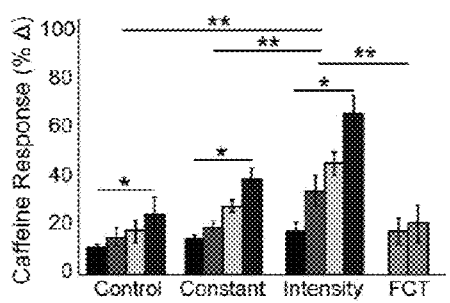
Figure 30E:
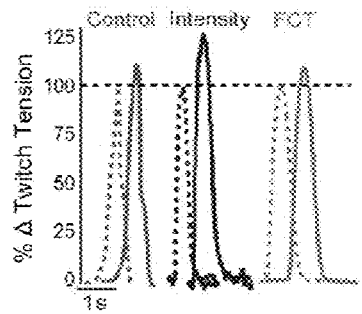
Figure 30F:
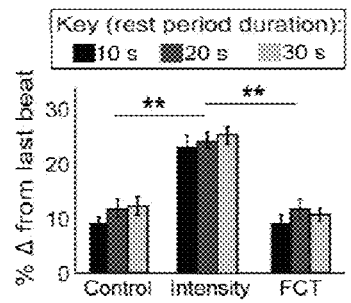
Figure 30G:
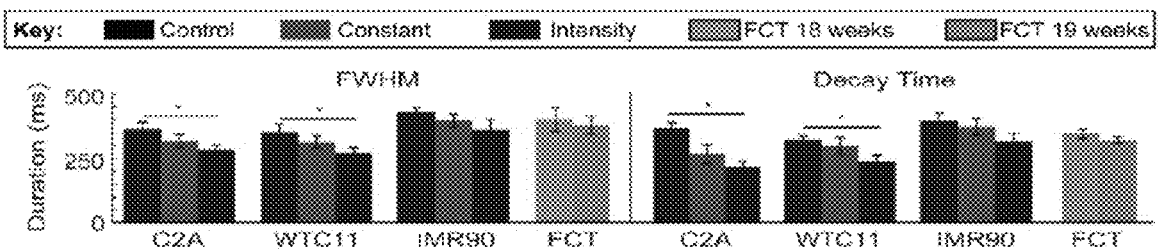
Figure 30H:
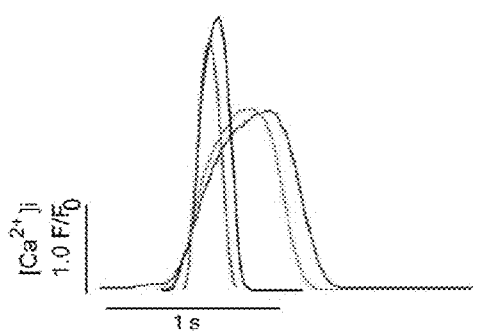
Figure 30I:
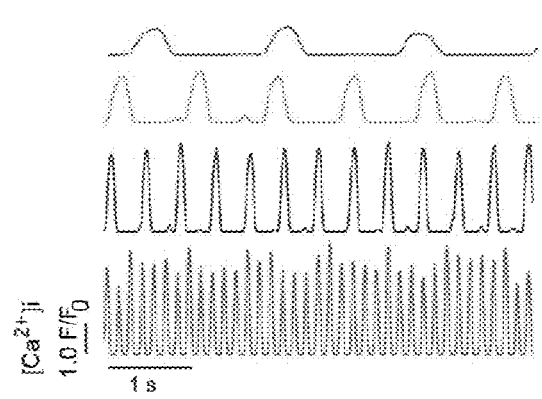

A positive Frank-Starling response (increased twitch tension with increased length) was observed after 4 weeks of cultivation under all conditions as well as in FCTs (FIG. 20C; FIG. 25H), but only organoids, the organoids that experienced intensity training, exhibited mature calcium handling (FIGS. 27A-27C, FIG. 30G) and FDAR (FIGS. 30H-30I). While both FDAR and Frank-Starling responses have been demonstrated for hiPS-CMs, their immature phenotype prevented the functional convergence of lusitropic and ionotropic responses into a positive force-frequency relationship (FFR). When treated with the beta-adrenergic stimulus Isoprenaline, the organoids significantly increased their twitch tension (FIG. 26B), a response not seen in fetal cardiac tissues. These results correlated to the organoid's calcium sensitivity, as measured by the Calcium EC50 (FIG. 26A). Unstimulated organoids and FCTs lack a positive FFR (FIG. 20D), despite displaying FDAR and Frank-Starling response. In contrast, electromechanically trained organoids established a positive FFR after only 2 weeks of intensity training or 4 weeks of constant training (FIG. 20D, FIG. 26C). In contrast, control and constant training organoids and FCTs lacked a positive FFR despite their Frank-Starling responses. The dose-dependent response of contractile force to extracellular calcium was increased with intensity training (FIG. 20E). The measured increase in the maximum capture rate (MCR) and decrease in the excitation threshold (ET) (FIG. 20F, FIG. 20G) support the role of electromechanical training in functionally maturing hiPS-CMs.

When treated with the beta-adrenergic drug isoproterenol, organoids—but not the other organoids or FCTs—responded by increasing twitch tension (FIG. 26B). These results correlated to calcium sensitivity measured by the calcium EC50 (FIG. 26A). To further investigate functional calcium storage in the sarcoplasmic reticulum, organoids, controls and FCTs were exposed to caffeine, but only organoids were seen to release intracellular calcium (FIG. 30A-D).

Blocking the Cav1.2 calcium channels by verapamil resulted in cessation of calcium transients in all tissues (FIG. 38A). Addition of caffeine released intracellular calcium in intensity-trained organoids but not in other groups (FIG. 20H), suggesting that only intensity-trained organoids have functional intracellular calcium stores. When the ion-transport activity of the SR $Ca^{2+}ATPase$ (SERCA) was blocked by thapsigargin, the calcium transients ceased quickly in intensity-trained organoids, as calcium was depleted from the SR. Subsequent addition of caffeine had no effect on either group (FIG. 20I; FIG. 38B). The lack of this response in unstimulated organoids and FCTs (FIG. 20I) further confirmed that their calcium handling is largely dependent on extracellular calcium supplies. The ability to release calcium from SR stores when needed was further demonstrated by the increased force generation after post-rest potentiation measurements in organoids (FIGS. 30E-30F).

Consistent with the calcium handling data, the transcription of two genes responsible for clearing cytosolic calcium: SLC8A1 (encoding for the Na—Ca Exchange Pump NCX), and ATP2A2 (encoding for SERCA), increased over time in the intensity-trained ORGANOIDs (FIG. 39). Intensity-driven expression of SERCA and NCX enhanced sequestration and extrusion of calcium, enabling the iPS-CMs to relax more quickly and respond to subsequent contractile triggers. Overall, intensity training enhanced transcription levels of genes encoding for cardiac structure, calcium handling, energetics, and maturation (FIG. 21A, FIG. 22A, FIG. 28).

Figure 29A:
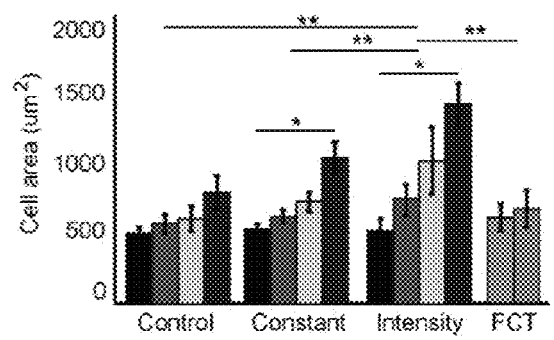
Figure 29B:
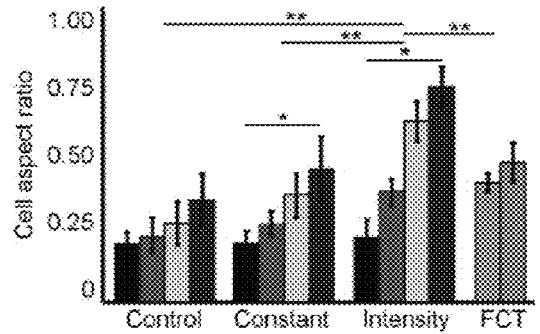

Constantly increasing the contractile demand within intensity trained organoids resulted in the maturation of CM morphology, to increase force production. Overall, intensity training resulted in increased cell size (twice as large as fetal cells), an indicator of physiological hypertrophy, and cell elongation, an indicator of maturation (FIG. 29A, FIG. 29B). The sarcomere length of ~2.2-2.3 µm that was achieved after 4 weeks of intensity training (FIG. 29C) corresponds to that seen in the adult human myocardium. As evidenced by fractional shortening data (FIG. 29D), the physiological sarcomere length correlated with the contractile capacity. Consistently, the dose-dependent response of contractile force to extracellular calcium, the maximum capture rate (MCR) and the excitation threshold (ET) all improved in the organoids (FIGS. 20E-20G, FIGS. 25F-25G), consistent with their functional maturity.

Functional properties of the organoids were associated with remarkably mature ultrastructural features (FIG. 40A). Networks of T-tubules were clearly present in both the longitudinal and axial orientation (FIGS. 22B-22F; FIGS. 31A-31C, FIG. 41 images C-E, FIG. 42), beginning at 2 weeks in intensity-trained ORGANOIDS and continuing to develop over time (FIG. 34). Intensity-trained ORGANOIDs showed high expression of calcium-induced calcium release modulators: the ryanodine receptor 2 (RyR2), responsible for releasing calcium from the SR, and junctophillin-2 (JPH2), responsible for approximating RyR2 with Cav1.2 channels by mediating the junction between the SR and T-tubules (FIG. 21E; FIG. 40B).

Figure 29C:
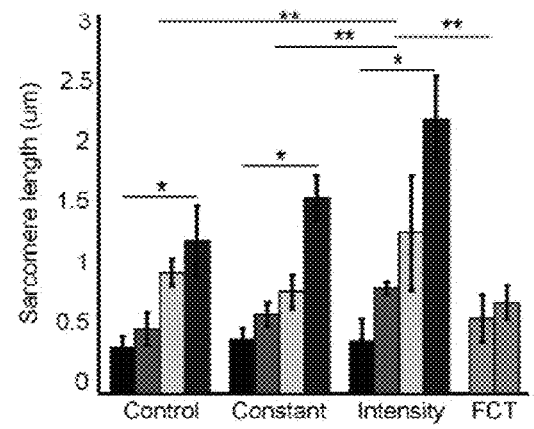
Figure 29D:
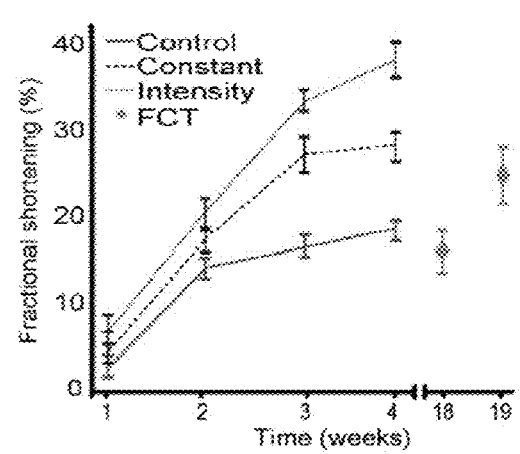

Transmission electron microscopy (TEM) sections of intensity-trained organoids revealed long and orderly registers of sarcomeres with well-developed striations, z-bands, m-lines, desmosomes, intercalated discs, and high density of mitochondria positioned near the contractile machinery (FIG. 41 images F-H, see also, FIG. 34 images A-H). The abundance of mitochondria is consistent with upregulation of SLC2A4 (encoding for Glut4) (FIG. 22A). The ultrastructure was significantly less developed for the unstimulated, constantly trained, and fetal tissues (FIG. 33). The formation of T-tubules in the organoids was evident at 2 weeks and continued to develop over time. Additionally organoids displayed enhanced mitochondria density (FIG. 34 images A-C, FIG. 34 image E), and the m- and z-lines (FIG. 34 images E-H), indicating sarcomeric maturation. The contractile demand resulted in increased cell size (by a factor of two compared to fetal cells (FIG. 29A, FIG. 29B), an indicator of physiological hypertrophy and cell elongation, an indicator of maturation. The sarcomere length of ~2.2-2.3 µm achieved after 4 weeks of intensity training corresponds to that seen in adult human heart (FIG. 29C). As evidenced by fractional shortening data (FIG. 29D), the physiological sarcomere length corresponded to improved contractile capacity.

Figure 23A:
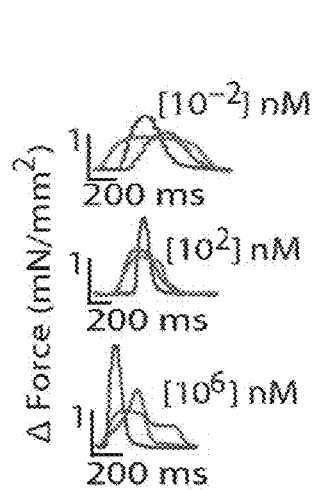
Figure 23B:
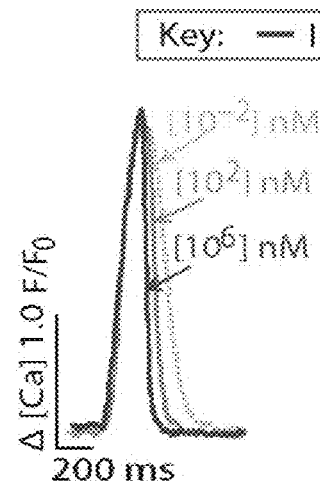
Figure 23C:
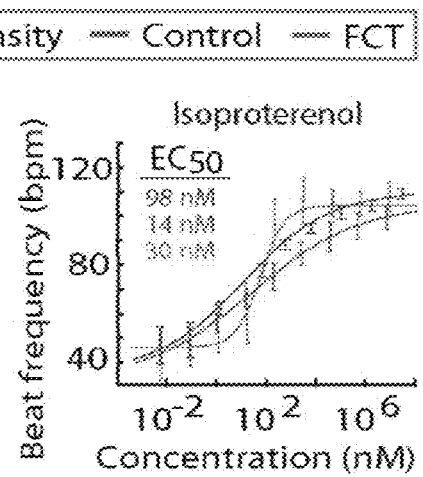
Figure 23D:
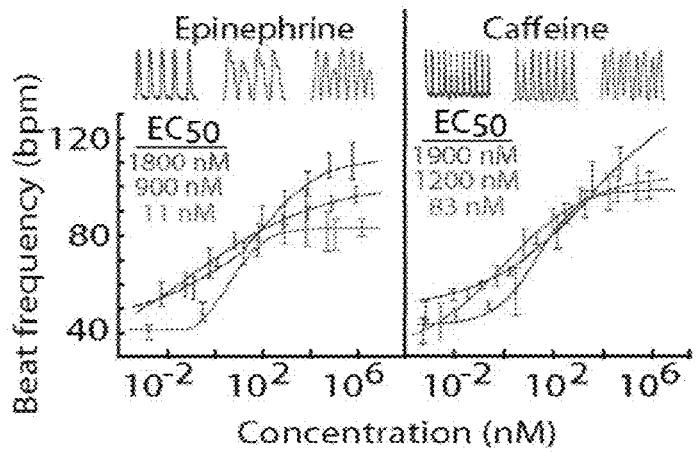
Figure 23E:
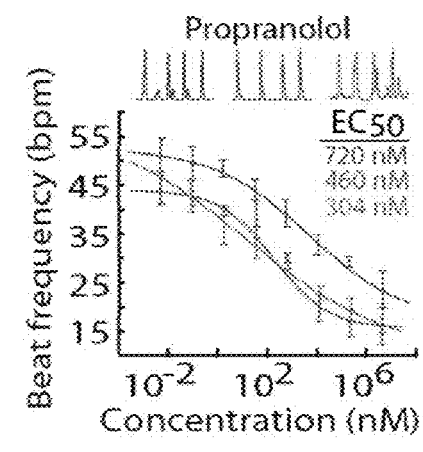
Figures 23F, 23G:
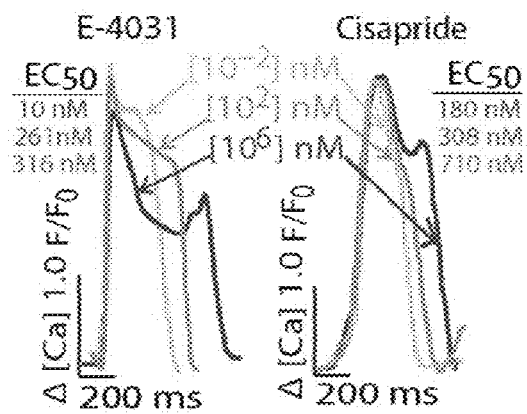
Figure 23H:
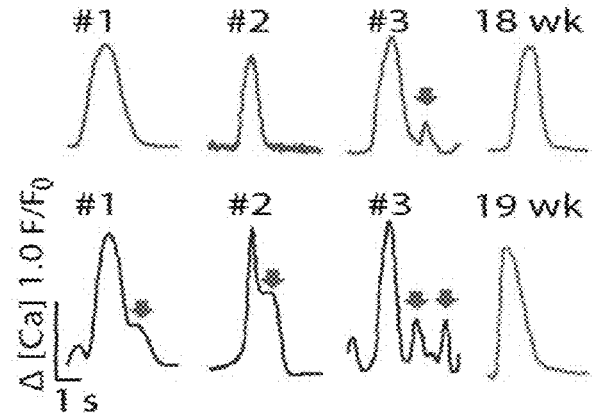

The functionally matured organoids were validated as physiologically relevant predictors of drug responses. The electromechanical induction of mature calcium homeostasis and ultrastructural maturation enabled positive ionotropic (FIG. 23A), lusitropic (FIG. 23B), and chronotropic (FIG. 23C) responses to the β-adrenergic agonist isoproterenol, a phosphorylator of multiple SR-related targets whose functional response is greatly diminished in detubulated CMs (Orchard). Since the functional β-adrenoceptor system is dependent on the proximity of Cav1.2 channels and T-tubules, comprehensive responses to β-adrenergic agonists are an important indicator of phenotypic maturation. Also, predictable changes in beating frequency were measured for positive (FIG. 23D) and negative (FIG. 23E) chronotropic drugs. Overall, the measured EC50 values—drug concentrations corresponding to a 50% change in tissue function—were within the ranges of blood plasma levels measured in clinical studies. For comparison, unstimulated organoids and fetal tissues showed lower EC50 values, a result of increased drug sensitivity of functionally immature CMs (FIGS. 23C-23E).

Beyond demonstrating pharmacologically tunable changes in force and frequency, intensity-trained organoids displayed excellent predictability of clinically reported EC50 values for drugs inhibiting the hERG potassium channel, a frequent cause of arrhythmogenic side effects. The intracellular calcium transients were prolonged as the concentrations of E-4031 (FIG. 23F) and cisapride (FIG. 23G) increased, leading to early after-depolarizations (EADs) (FIG. 23H), which can trigger lethal arrhythmias. The other organoids and FCTs did not recapitulate proarrythmic tendencies when exposed to cisapride, resulting in poor predictive power for drug screening. Overall, the formation of T-tubules and proper calcium homeostasis within organoids enables studies of drug-induced changes in ion channels and macroscale handling in calcium, and of the contractile and functional dynamics, which, when disrupted, may cause arrhythmia.

The enhanced functional maturation of intensity-trained organoids enabled phenotypic recapitulation of Timothy Syndrome (TS), by using iPS cells obtained from an affected patient and a healthy family member. Patients with TS carry an autosomal dominant gain-of-function mutation within the DNA encoding for the Cav1.2 channel (CACNA1C), which is critical for EC coupling. This mutation causes the Cav1.2 channel to remain open longer than normal, resulting in depletion of calcium from the SR, accumulation of calcium in the cytosol, prolongation of the QT interval, and cardiac arrhythmia that can lead to sudden cardiac death. The TS phenotype in vitro was evidenced by slow, irregular contractions (30 bpm for TS organoids compared to 60 bpm for healthy controls, FIGS. 24A, 35A), consistent with bradycardia found in TS patients. Representative calcium transients in TS organoids (FIG. 24B, FIG. 35B) revealed skipped beats and other beating irregularities, which were partially ameliorated through electromechanical stimulation (FIG. 24C).

Figure 35A:
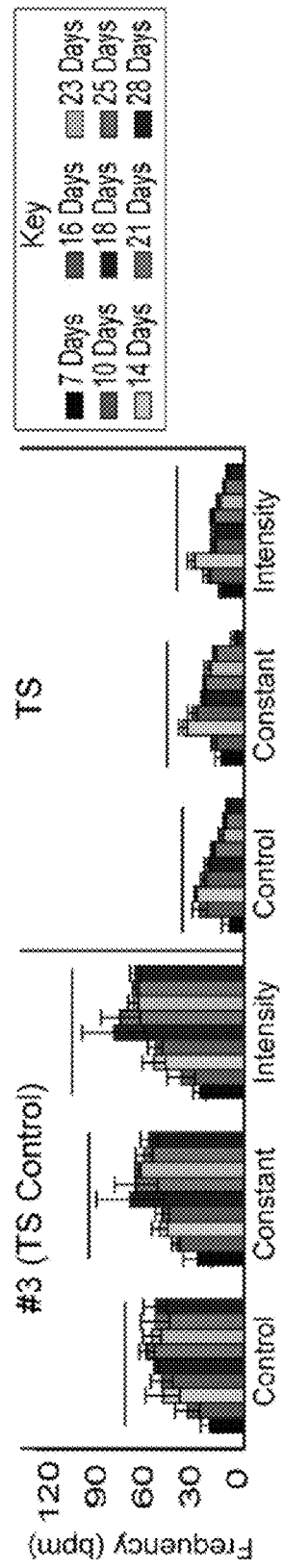
Figure 35B:
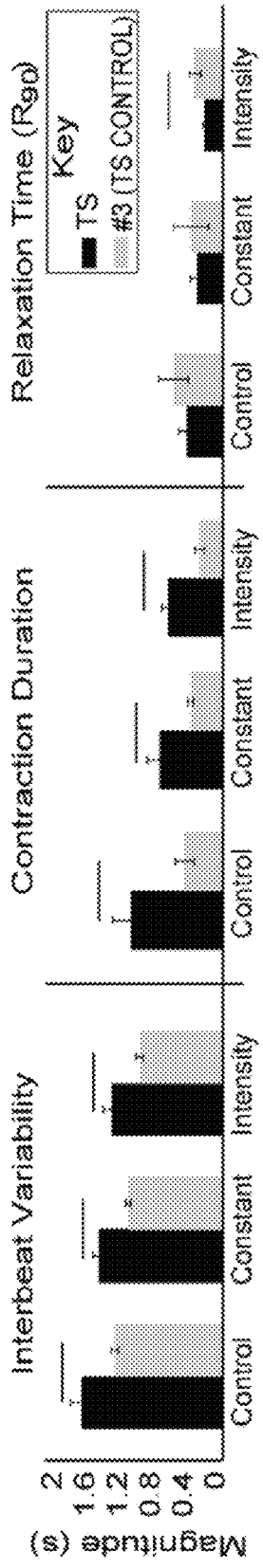
Figure 35H:
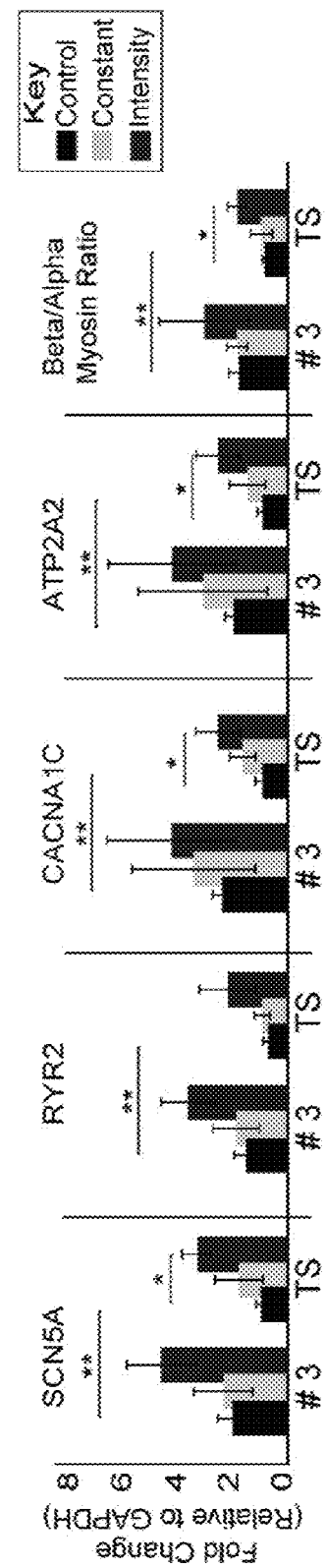

One important aspect of modeling TS is to recapitulate arrhythmic conditions arising from calcium accumulation in cytosol. In contrast to healthy organoids, the calcium transient amplitudes in TS organoids decreased in a frequency-dependent manner as calcium was depleted from the SR (FIG. 24D). The application of nifedipine to block the Cav1.2 channel resulted in decreased Ca2+ transient amplitudes, until the addition of caffeine released Ca2+ back into the cytosol (FIG. 35D). TS organoids also displayed increased contraction duration (FIG. 35E), which is a proxy for impaired calcium handling and prolonged action potentials (FIGS. 35F-35G), that increases the risk of long QT, torsades de pointes, and ventricular fibrillation. Genes associated with calcium handling were upregulated via intensity training, but to a lesser extent in the TS organoids model (FIG. 35H). Upregulation of calcium handling suggests a possible mechanism for the observed functional improvements. Consistently, TS organoids demonstrated negative force-frequency relationships for all training regimens (FIG. 24E), despite displaying similar morphological ultrastructure (FIGS. 43A and 43B).

Because TS patients experience increased proarrhythmic events under increased cardiac demand, β-adrenergic stimulation was used to mimic the clinical stress tests. Isoproterenol treatment of TS organoids resulted in increased calcium transients, prolonged QT intervals, and led to proarrhythmic EADs, as seen in TS patients undergoing a stress test. Exposure of TS organoids to therapeutic concentrations of verapamil, a calcium channel blocker, rescued the phenotype (FIG. 24G), supporting its use in TS patients. An increased incidence of EADs under the effects of cisapride (FIG. 24F) and epinephrine (FIG. 35C) also was demonstrated. To test the mechanical effect of increased intracellular [Ca2+] in TS, the force generation in response to extracellular calcium was measured. Healthy controls increased force generation with increasing [Ca2+], a response that was enhanced by intensity training, whereas TS organoids displayed Ca2+ overload, resulting in decreased force (FIG. 24H). Notably, propranolol, a β-adrenergic blocker used to manage TS, reversed some of these effects (FIG. 24H).

Figure 45D:
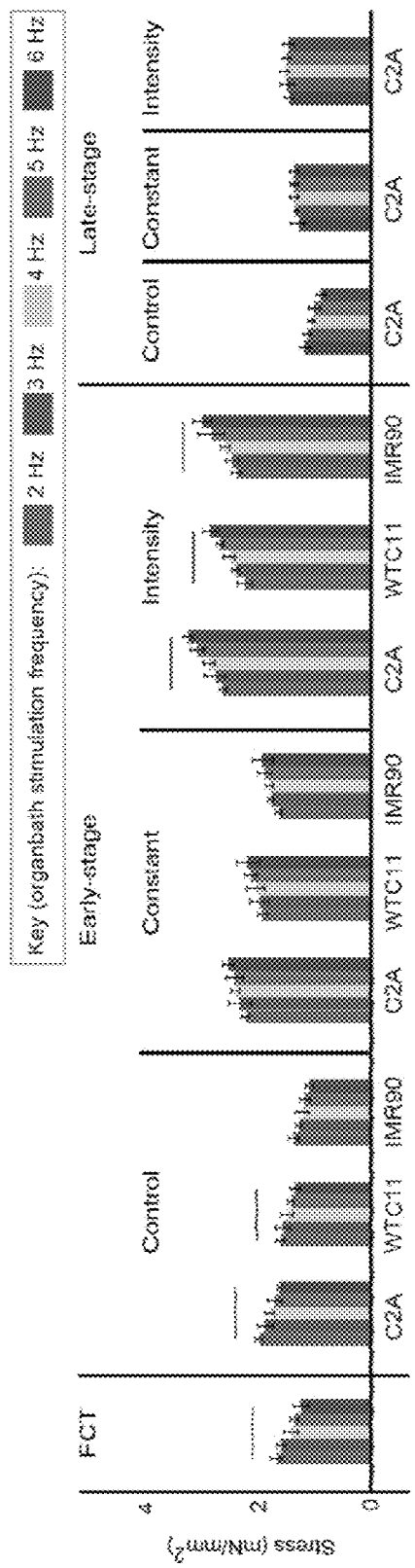
Figure 45E:
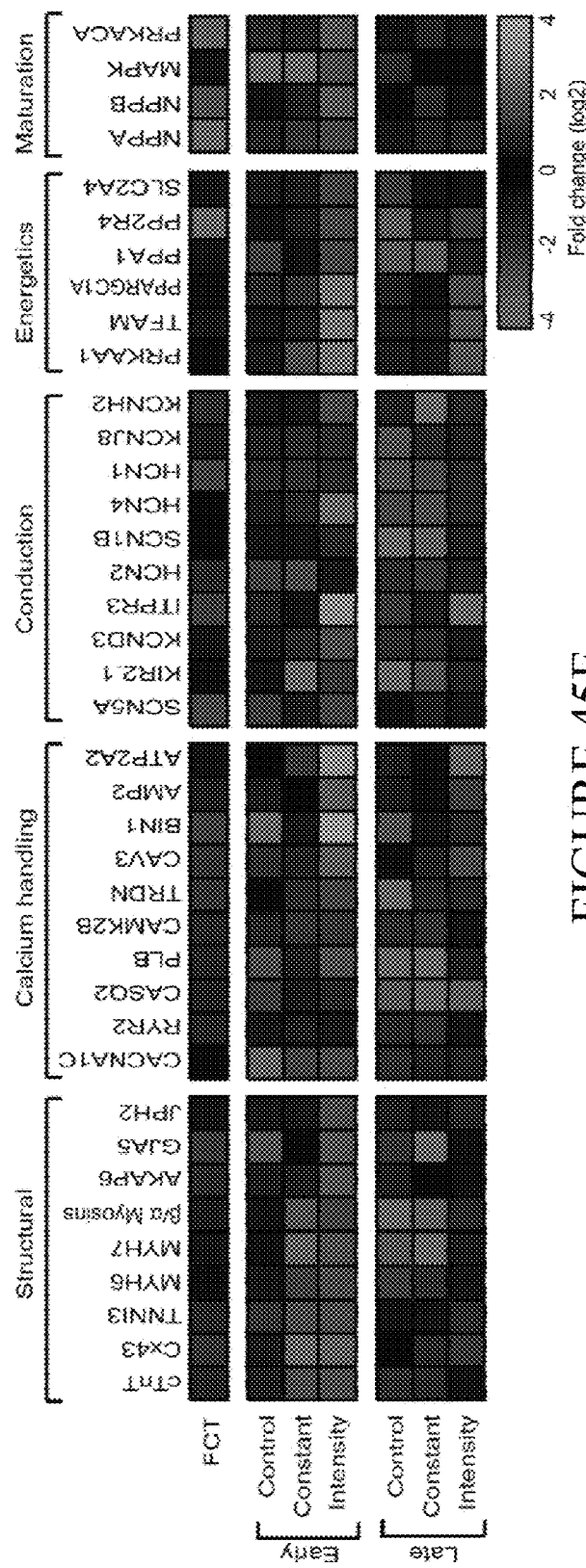

Referring to FIGS. 44A to 44C, data showing enhanced maturation and synchronicity of organoids in response to training regimen as a function of time is shown for FCT (44A), early-stage organoids (44B) and late-state organoids 44(C) (C2A cell line) over time. FIGS. 45A-45E show adult-like contractile behavior and gene expression. Referring to FIG. 45A, an experimental design for early-stage or late-stage iPS-CMs and supporting fibroblasts is shown. As depicted the iPS-CMs and supporting fibroblasts were encapsulated in fibrin hydrogel to form organoids stretched between two elastic pillars and forced to contract by electrical stimulation. Gradual increase in frequency to supraphysiological levels (intensity regime) was compared to stimulation at constant frequency (constant regime), no stimulation (control), and strips of human fetal heart ventricles (FCT, 4.5 months old). FIG. 45B, Frequency of contractions and FIG. 45C, cell area in cardiac organoids over 4 weeks of culture. n≥12 per group, Mean±95% CI, *=p<0.05 compared to FCT group by ANOVA with Tukey's HSD test. Early-stage intensity training is significant against other training regimens by 2-way ANOVA with Tukey's HSD test. d, The force-frequency relationship of cardiac organoids grown from three iPS lines (C2A, WTC11, IMR90) after 4 weeks of culture. n≥12 per group, Mean±95% CI, -=p<0.05 within group by ANOVA. e, Gene expression data for cardiac organoids (C2A line, 4 weeks of culture, fold change relative to late-stage organoids at the start of stimulation) and FCTs.

Data are shown for early-stage organoids after 4 weeks of culture and 18-19 week FCTs in FIGS. 46A-46J. Referring to FIG. 46A, immunofluorescent images detailing ultrastructural proteins: (green: α-actinin, red: cardiac troponin-T (cTnT), blue: nuclei) for hiPS-CM organoids (C2A cell line) and FCTs (scale bar: 10 μm). FIG. 46B shows corresponding transmission electron micrographs (scale bar: 1 μm) and FIG. 46C, depicts registers of sarcomeres with A- and I-bands, and M- and Z-lines, sarcoplasmic reticulum and t-tubules in the intensity trained organoids (scale bar: 1 μm).

Referring to FIG. 46D, the density of mitochondria (% area) in organoids and FCTs; shaded area: adult human heart; n≥6 per group, Mean±95% CI, and *=p<0.05 by ANOVA with Tukey's HSD test compared to FCT are shown. FIG. 46E indicates lipid droplets (red asterisk, scale bar: 1 μm). (FIGS. 46F-46H) show ultrastructure of intensity trained organoids. FIG. 46F, a brightfield image with planes denoting sections taken to evaluate t-tubules (scale bar: 100 μm). Immunostains of t-tubule system: g, longitudinal section and h, axial cross-section (green: wheat germ agglutinin (WGA); red: cTnT; blue: nuclei; scale bar: 10 μm). FIG. 46I shows immunofluorescent images of calcium handling ultrastructure: WGA; di-8-anepps; bridging integrator 1 (BIN1); Ryranodine 2 (RyR2); L-type calcium channels (Cav1.2) (scale bar: 15 μm). FIG. 46J, Regular spacing of calcium handling proteins correlate with each other as shown by the intensity profiles color-coded to match the corresponding boxes in FIG. 46I.

Figure 47A:
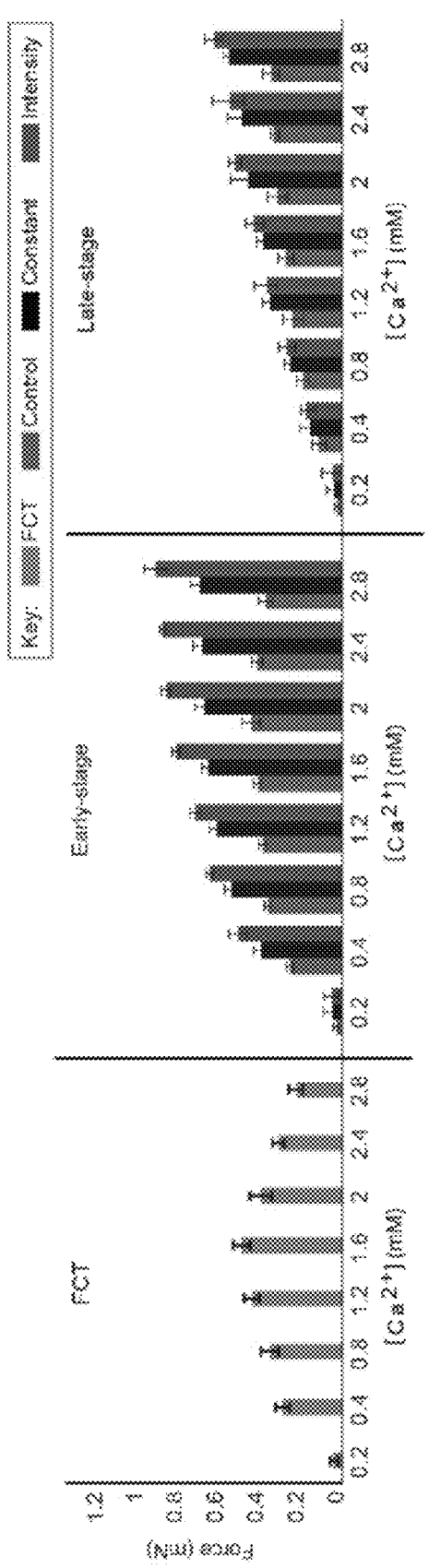
Figure 47B:
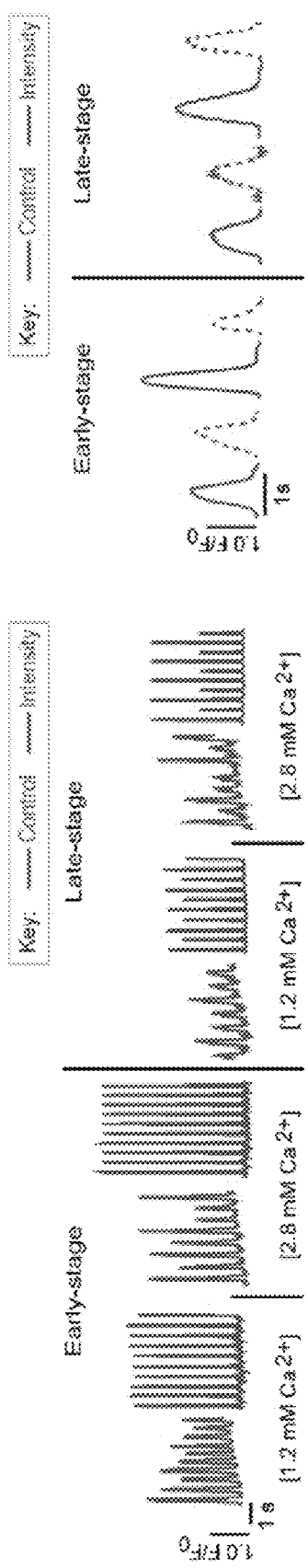
Figure 47C:
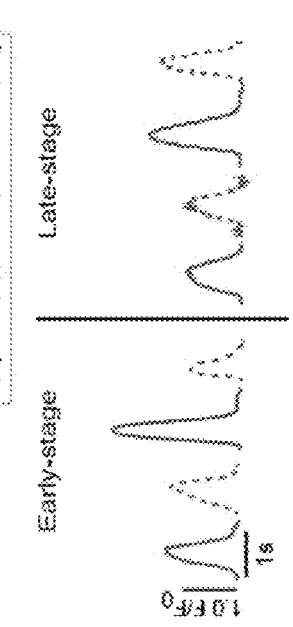
Figure 47J:
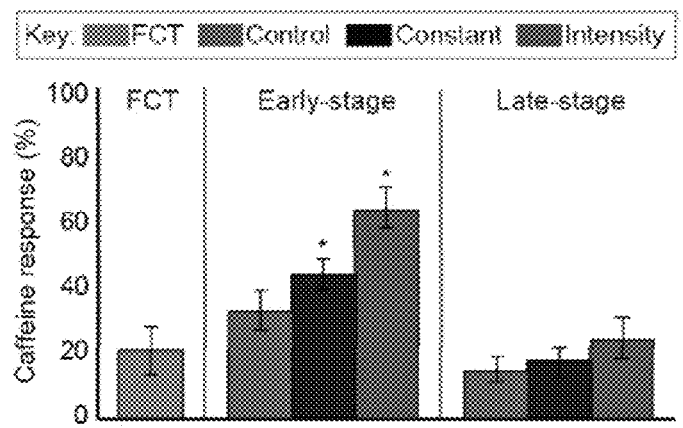
Figure 47K:
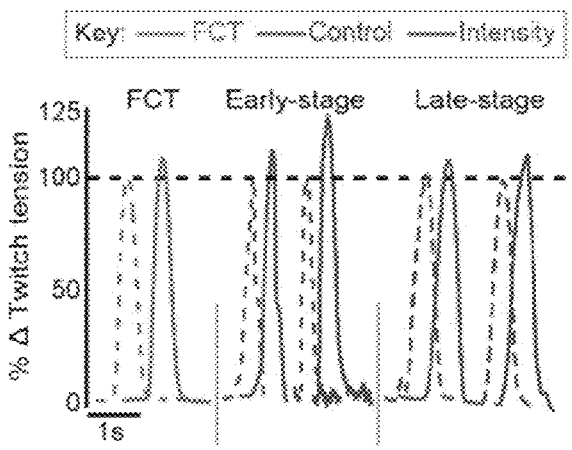
Figure 47L:
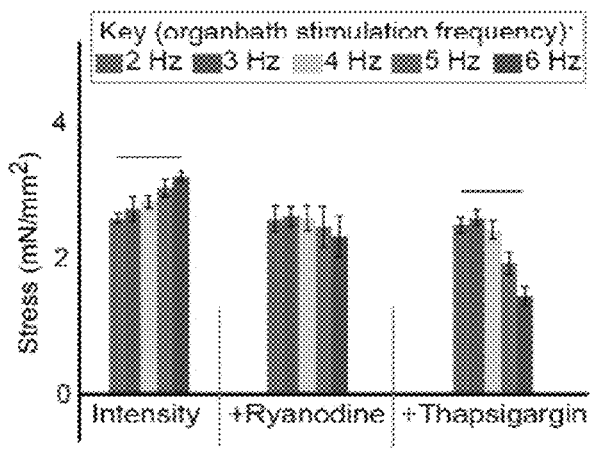

According to FIGS. 47A-47C, calcium handling, data are shown for organoids after 4 weeks of culture and 18-19 week FCTs. FIG. 47A shows a force of contraction in response to changes in extracellular calcium concentration [Ca2+]. n≥6 per group, Mean±95% CI. Early-stage intensity training is significant against other training regimens and FCT by 2-way ANOVA with Tukey's HSD test. In FIG. 47B, calcium spikes (by immunofluorescent calcium dyes) in early-stage and late stage intensity trained organoids (blue) and unstimulated controls (red) at two [Ca2+] levels are depicted. FIG. 47C shows that intensity trained early-stage but not late-stage organoids respond to ryanodine (1 μmol/L). Referring to FIGS. 47D-47E, early-stage intensity trained organoids demonstrate frequency-dependent acceleration of relaxation, as shown for each stimulation frequency by FIG. 47D, traces of calcium and FIG. 47E, individual peaks. FIG. 47F shows immunofluorescence images of calcium handling proteins within early-stage intensity trained organoids (scale bar: 20 μm). FIGS. 47G and 47H are representative traces of calcium release after stimulation with 5 mM caffeine in early-stage organoids and FCTs treated with FIG. 47G, 2 μM thapsigargin or FIG. 47H, 1 mM verapamil. FIG. 47I, representative traces of calcium release after stimulation with 5 mM caffeine for early-stage organoids and FCTs. In FIG. 47J, calcium release after stimulation with 5 mM caffeine in organoids and FCTs, shown as the change in the fluorescent calcium trace relative to the pre-stimulus magnitude. n≥3 per group, Mean±95% CI, *=p<0.05 by ANOVA with Tukey's HSD test compared to FCT. FIG. 47K shows representative traces during post-rest potentiation tests corresponding to the amount of stored calcium during 10 seconds of rest within organoids (4 weeks of culture) and FCTs. 1, The force-frequency relationship of early-stage intensity trained cardiac organoids (C2A line) after 4 weeks of culture treated with the serca2a blocker thapsigargin (1 μM) or the ryranodine blocker ryanodine (1 μM). n≥3 per group, Mean±95% CI, -=p<0.05 within group by ANOVA.

Referring now to FIGS. 48A and 48B, data of gene expression within cardiac organoids over time is represented. FIG. 48A shows quantitative gene expression of FCTs and C2A hiPS-CM organoids as determined by qPCR after 2 weeks of culture, fold change relative to late-stage organoids at the start of stimulation. FIG. 48 b shows quantitative gene expression of early-stage hiPS-CM organoids, normalized to GAPDH, from 3 different lines as determined by qPCR after 4 weeks of culture. n≥12 per group, Mean±95% CI, no significance at p<0.05 between different cell lines by 2-way ANOVA.

FIGS. 49A and 49B show cardiac maturation over time in response to intensity training. FIG. 49A shows representative immunofluorescent images detailing various ultrastructural proteins (WGA/wheat germ agglutinin (green), α-actinin (red), mitochondria (blue), oxidative phosphorylation (yellow)) for early-stage hiPS-CM organoids (C2A cell line) at different culture times during exposure to the intensity training electromechanical conditioning regimen (scale bar=20 μm). FIG. 49B shows representative immunofluorescent images detailing various ultrastructural proteins (WGA/wheat germ agglutinin (green), α-actinin (red), mitochondria (blue), oxidative phosphorylation (yellow)) of organoids cultured under intensity training for 4 weeks from early-stage hiPS-CMs (C2A cell line), late-stage hiPS-CMs (C2A cell line), and 19 week old fetal cardiac tissue (FCT) (scale bar=20 μm).

In FIGS. 50A and 50B the data indicates that intensity training of early-stage hiPS-CMs is required to enhance mitochondrial development. Representative TEM images for early-stage (FIG. 50A) and late-stage hiPS-CM organoids (C2A cell line) (FIG. 50B) after 2 weeks of exposure to the intensity training electromechanical conditioning regimen (scale bar=1 μm).

Referring to FIG. 51, data show physiological responses of the engineered tissues grown under the intensity training regimen to the drug isoproterenol. As seen in patients, the drug has a dose-dependent effect on three functional properties: beating frequency (chronotropic response), force generation (ionotropic response) and calcium handling (lusitropic response). The table shows that the intensity trained group, but not the other groups, shows physiological responses (i.e., comparable to those measured in patients) for a number of representative drugs. Finally, the matured, intensity trained cardiac tissues had capability to predict specific, differential effects of a drug (Cisapride, a gastrointestinal drug pulled off market) on patients with inherited cardiac myopathy (Timothy syndrome, characterized by a calcium channel defect).

FIG. 52 shows adult-like contractile behavior on the organoids described herein. The force frequency relationship of cardiac organoids, calcium handling, contractility and cell size data is shown. The force frequency relationship of cardiac organoids, calcium handling, contractility and cell size data is shown. In response to a pathological hypertrophy agent, the cell size increases, the calcium responses deviate from normal, and the positive force-frequency relationship reverses into a negative relationship.

Figure 53F:
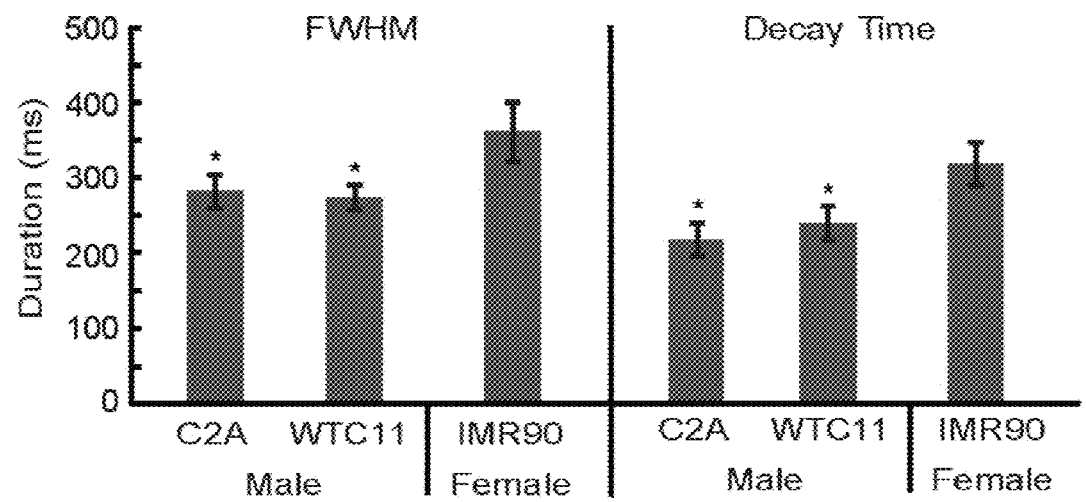
Figure 53G:
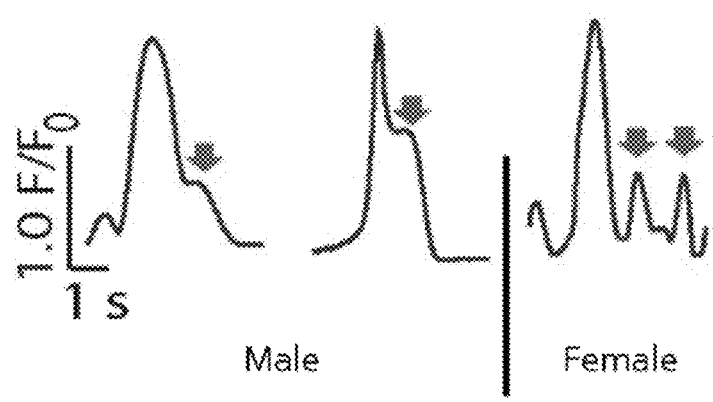

FIGS. 53A-53G show preliminary cardiac tissue data. As shown, bone tissue is grown from mesenchymal stem cells. FIG. 53A provides an experimental design: early-stage iPS-CMs and supporting fibroblasts were encapsulated in fibrin hydrogel to form organoids stretched between two elastic pillars and forced to contract by electrical stimulation at a frequency that gradually increases to supra-physiological levels (intensity regime). Referring to FIG. 53B, a schematic depiction of the tissue pillar in accordance with the bioreactor to make the organoids described herein is illustrated. As shown the tissue is disposed on the pillars. FIG. 53C is a photograph of the cardiac organoids cultured within the bioreactor. Referring to FIG. 53C, a Brightfield image with planes denoting sections taken to evaluate t-tubules (scale bar: 100 μm) is shown. Immunostains of t-tubule system: (FIG. 53D) longitudinal section and (FIG. 53E) axial cross-section (green: wheat germ agglutinin (WGA); red: cTnT; blue: nuclei; scale bar: 10 μm). FIG. 53F shows relaxation times within male and female cardiac organoids as characterized by the Full-Width Half-Max (FWHM) values and the Decay Time (90% of the time from the maximal peak of the calcium transient). n≥6 per group, Mean±95% CI, *=p<0.05 versus female group by ANOVA with Tukey's HSD. FIG. 53G indicates that high concentrations of Cisapride (1 μM) reveal increased proarrythmic Early After Depolarizations (depicted by red arrows) in female cardiac organoids.

In another embodiment, FIG. 55 shows a personalized, patient-derived design in which early-stage iPS-CMs and supporting fibroblasts were encapsulated in fibrin hydrogel to form organoids stretched between two elastic pillars forced to contract by electrical stimulation, at a gradually increasing frequency (intensity regime).

FIG. 56 shows various electromechanical conditioning regimes in which the use of varying electromechanical stimulation regimens can be investigated in a manner that mimics current "heart healthy" workout regimens. Specifically, the use of "interval training" involved short durations of high frequency electrical stimulation delivered via a customized Arduino based voltage stimulator. The stimulation baseline frequencies of 1 Hz, 2 Hz, and 3 Hz were chosen to mimic bradycardic, eucardic, and tachycardic human heart rates, respectively. Within each of these baseline groups, interval training regimens were designed to mimic moderate (M) intensities (60% increase in beat frequency for 1 hour), prolonged moderate (ML) intensities (60% increase in beat frequency for 2 hours), and high (H) intensities (90% increase in beat frequency for 1 hour) as detailed in tabular form in FIG. 56. Electromechanical stimulation at high rates is expected to mature CMs in the shortest time possible. However, high stimulation frequencies lead to the buildup of toxic byproducts near the electrode surface and thus, are harmful to the cells. Thus, the use of high intensity interval training regimens can maximize the positive effects of stimulation at high frequencies while negating the negative effects arising from constant stimulation at high frequencies.

As depicted in FIG. 57, changes in energy supplies enable more physiologically relevant resources for proper EC coupling, as was demonstrated within the higher intensity interval stimulation regimens. Mitochondrial content occurred as a result of increased intensity within the various exercise regimens. Overall, the coupling of metabolically active mitochondria and functional uptake and storage of Ca2+ within the SR are critical in facilitating proper EC coupling. The energetically demanding functions associated with proper calcium handling can therefore be matured through the use of high intensity interval stimulation regimens. This enables the upregulation of mitochondrial biogenesis to ensure adequate ATP transport of Ca2+ into the SR, thereby increasing SR storage and function simultaneously. The use of high intensity interval regimens enables these beneficial effects while minimizing the negative effects associated with ROS generation at prolonged intervals of stimulation at high frequencies.

The embodied method and systems described above show that using cells at an earlier time point was important to their successful tissue formation and maturation as such tissues are more responsive to electrical stimulation. This helped to switch their mitochondrial functionality and calcium handling/storage to more mature mechanisms.

It has been shown that the use of engineered human tissues for in vitro drug testing and disease modeling has vast potential for tackling the burden of heart disease, however, this potential has yet to be realized. The main limitation of currently used in vitro systems is that the hiPS-CMs have not been cultured in a manner that promotes maturation. To overcome this barrier, a biomimetic system that incorporates biophysical cues critical for heart development and function: supporting cells, electrical stimulation, and mechanical loading is provided. The approach described herein implements dynamic anisotropic loading of cell-hydrogel constructs that are driven to maturity by working against physiological forces at a gradually increasing intensity. Remarkably, organoids, the only group cultured under intensity training, displayed two ultimate hallmarks of tissue maturity: a positive force-frequency response (FIG. 20D) and networks of T-tubules (FIG. 22 B-D, F; FIG. 22A, FIG. 41 images C-F). These benchmarks have been a major goal of cardiac tissue engineering.

Figure 26D:
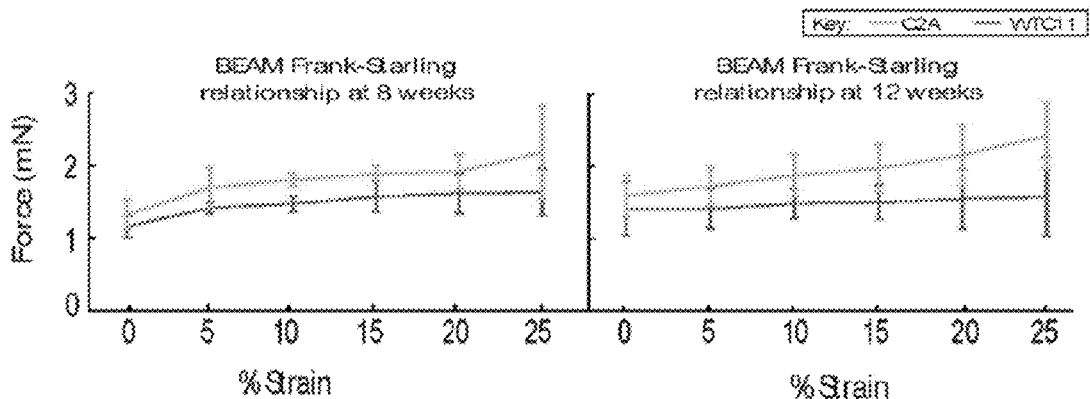
Figure 26E:
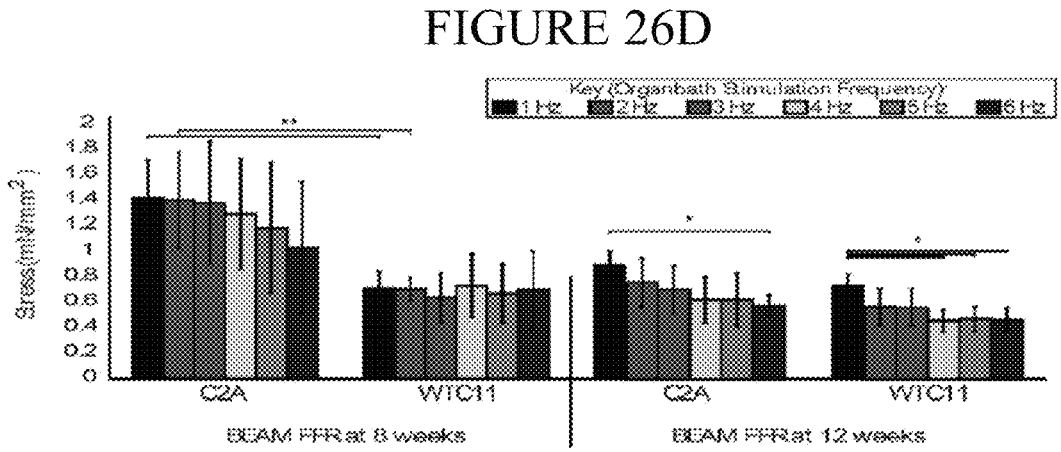

The examples described supra demonstrates the importance of electromechanical loading for establishing and maintaining healthy heart muscle. ORGANOIDs under intensity training greatly exceed the maturity of ~4.5 month old fetal tissue across a wide variety of parameters. When electrical stimulus was discontinued and ORGANOIDs were maintained in culture for 3 months, they appeared to developmentally regress, as demonstrated by the loss of T-tubules (FIG. 32E) and the return of a flat FFR (FIG. 26E), despite maintaining a positive Frank-Starling response (FIG. 26D). Also, studies using surgically removed samples during repair of congenital heart defects have demonstrated the presence of a positive FFR in infants (3-14 months) but not in newborns (<2 weeks), suggesting that the tissues described herein are not equivalent, developmentally, to fetal myocardium.

The unprecedented maturity of the organoids allowed development of physiologically relevant platforms for evaluating drugs and modeling disease, with the ability to measure force and frequency of contractions in real time. Importantly, different functional properties are achieved at different times. The studies indicate that that physiological responses were established sooner for chronotropic drugs (frequency response, by 2 weeks) than for ionotropic drugs (force response, by 4 weeks) or for modeling TS, a complex disease that affects multiple functions of the heart.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What we claim is:

1. An engineered three dimensional micro-tissue comprising a cell-hydrogel construct comprising electromechanically conditioned mature cardiomyocytes and dermal fibroblasts encapsulated in a fibrin hydrogel, and wherein the electromechanical conditioning comprises subjecting said construct to electrical stimulation that increases in intensity over a time period, wherein said electrical stimulation results in the micro-tissue comprising sarcomeres and a network of T-tubules.

2. The engineered three dimensional micro-tissue of claim 1, wherein the micro-tissue further comprises mitochondria or sarcoplasmic reticulum.

3. The engineered three dimensional micro-tissue of claim 1, wherein the micro-tissue exhibits a positive force-frequency relationship.

4. The engineered three dimensional micro-tissue of claim 3, wherein the positive force-frequency relationship comprises a force of about 1 to about 2 mN/mm2 at a frequency of about 0 to 6 Hz.

5. The engineered three dimensional micro-tissue of claim 1, wherein the micro-tissue exhibits a physiological response to beta-adrenergic stimulation.

6. The engineered three dimensional micro-tissue of claim 5, wherein the micro-tissue is useful for predictive drug screening, and further wherein the micro-tissue is capable of exhibiting a drug response.

7. The engineered three dimensional micro-tissue of claim 1, wherein the micro-tissue comprises sarcomeres, a network of T-tubules, mitochondria and sarcoplasmic reticulum.

8. The engineered three dimensional micro-tissue of claim 1, wherein the electromechanical stimulation comprises a frequency that increases gradually from 2 Hz at the end of week 1 to 6 Hz over a 2-week time period, and at 6 Hz for one more week.

9. The engineered three dimensional micro-tissue of claim 1, wherein the electromechanical stimulation comprises subjecting the engineered tissue to tension.

10. The engineered three dimensional micro-tissue of claim 1, wherein the sarcomeres are registers of sarcomeres having A- and I bands, and M- and Z-lines.

11. The engineered three dimensional micro-tissue of claim 1, wherein the network of T-tubules are disposed in both the longitudinal and axial orientations.

12. An engineered three dimensional micro-tissue, comprising: a cell-hydrogel construct containing electromechanically conditioned dermal fibroblasts and mature cardiomyocytes, and wherein the electromechanical conditioning comprises subjecting said construct to electrical stimulation that increases in intensity over a time period, wherein said electrical stimulation results in the micro-tissue comprising a network of transverse-tubules, and further wherein the micro-tissue exhibits a positive force-frequency response.

13. The engineered three dimensional micro-tissue of claim 12, wherein the electromechanically conditioned micro-tissue comprises a sarcoplasmic reticulum and the micro-tissue exhibits calcium homeostasis.

14. The engineered three dimensional micro-tissue of claim 12, wherein the network of transverse tubules are disposed in both the longitudinal and axial orientations.

15. The engineered three dimensional micro-tissue of claim 12, wherein the micro-tissue exhibits expression of calcium-induced calcium release modulators.

16. The engineered three dimensional micro-tissue of claim 15, wherein the calcium release modulators are selected from the group consisting of: ryranodine receptor 2, junctophillin-2 or a combination thereof.

17. An engineered three dimensional micro-tissue, comprising: a cell-hydrogel construct comprising electromechanically conditioned dermal fibroblasts and mature cardiomyocytes, wherein the electromechanically conditioning comprises stretching the construct between first and second pillars and subjecting said construct to electrical stimulation, said electrical stimulation including exposure to a frequency that gradually increase from 2 Hz to 6 Hz over a time period, and wherein said electrical stimulation results in the micro-tissue comprising sarcomeres and a network of transverse-tubules.

18. The engineered three-dimensional micro-tissue of claim 17, wherein the micro-tissue exhibits a positive force-frequency response.

19. The engineered three-dimensional tissue of claim 17, wherein the micro-tissue further comprises mitochondria or a sarcoplasmic reticulum.

20. The engineered three-dimensional tissue of claim 17, wherein the tissue exhibits a positive force-frequency relationship.

21. The engineered three-dimensional tissue of claim 20, wherein the positive force-frequency relationship comprises a force of about 1 to about 2 mN/mm2 at a frequency of about 0 to 6 Hz.

22. The engineered three-dimensional tissue of claim 17, wherein the micro-tissue exhibits a physiological response to beta-adrenergic stimulation.

23. The engineered three-dimensional tissue of claim 22, wherein the micro-tissue is useful for predictive drug screening, and further wherein the micro-tissue is capable of exhibiting a drug response.

24. The engineered three-dimensional micro-tissue of claim 17, wherein the mature cardiomyocytes are derived from induced pluripotent stem (iPS) cells from a patient having a disease, and further wherein the micro-tissue is used as a personalized disease model for the patient with the disease.

25. The engineered three-dimensional micro-tissue of claim 24, wherein the disease model is for a genetic disease.

26. The engineered three-dimensional micro-tissue of claim 25, wherein the genetic disease is Timothy syndrome.

27. The engineered three-dimensional micro-tissue of claim 24, wherein the disease model is for inflammation or hypoxia.

* * * * *